(12) United States Patent
Vicent Docón et al.

(10) Patent No.: US 10,155,050 B2
(45) Date of Patent: Dec. 18, 2018

(54) CROSS-LINKED STAR-SHAPED SELF-ASSEMBLED POLYPEPTIDES AND ITS USE AS CARRIERS IN BIOMEDICAL APPLICATIONS

(71) Applicant: CENTRO DE INVESTIGACION PRINCIPE FELIPE, Valencia (ES)

(72) Inventors: María Jesús Vicent Docón, Valencia (ES); Aroa Duro Castaño, Valencia (ES); Vicent Josep Nebot Carda, Valencia (EP)

(73) Assignee: CENTRO DE INVESTIGACION PRINCIPE FELIPE, Valencia (ES)

( * ) Notice: Subject to any disclaimer, the term of this patent is extended or adjusted under 35 U.S.C. 154(b) by 0 days.

(21) Appl. No.: 15/751,137

(22) PCT Filed: Jul. 22, 2016

(86) PCT No.: PCT/EP2016/067554
§ 371 (c)(1),
(2) Date: Feb. 7, 2018

(87) PCT Pub. No.: WO2017/025298
PCT Pub. Date: Feb. 16, 2017

(65) Prior Publication Data
US 2018/0228911 A1 Aug. 16, 2018

(30) Foreign Application Priority Data

Aug. 7, 2015 (EP) .................................. 15382422

(51) Int. Cl.
| | |
|---|---|
| *A61K 47/64* | (2017.01) |
| *A61K 31/35* | (2006.01) |
| *A61K 31/47* | (2006.01) |
| *A61K 31/437* | (2006.01) |
| *C08G 69/10* | (2006.01) |
| *C08G 69/36* | (2006.01) |
| *C08L 77/04* | (2006.01) |

(52) U.S. Cl.
CPC ............ *A61K 47/645* (2017.08); *C08G 69/10* (2013.01); *C08G 69/36* (2013.01); *C08L 77/04* (2013.01); *A61K 31/35* (2013.01); *A61K 31/437* (2013.01); *A61K 31/47* (2013.01); *A61K 2300/00* (2013.01); *C08L 2203/02* (2013.01)

(58) Field of Classification Search
CPC .. A61K 2300/00; A61K 31/35; A61K 31/437; A61K 31/47; A61K 47/645; C08G 69/10; C08G 69/36; C08L 2203/02; C08L 77/04
See application file for complete search history.

(56) References Cited

FOREIGN PATENT DOCUMENTS

WO    WO 03/055935 A1    7/2003

OTHER PUBLICATIONS

Crespo, L., et al., Peptide and Amide Bond-containing Dendrimers, Chem. Reviews, 35, vol. 105, No. 5, pp. 1663-1681 (2005) (Year: 2005).*
Chen, et al., "Emerging Synthetic Strategies for Core Cross-Linked Star (CCS) Polymers and Applications as Interfacial Stabilizers: Bridging Linear Polymers and Nanoparticles", vol. 34, Aug. 16, 2013, 1507-1517.
Crespo et al., "Peptide and Amide Bond-Containing Dendrimers", Chemical Reviews, vol. 105, Apr. 23, 2005, 1663-1682.
Duro-Castano, et al., "Well-Defined Star-Shaped Polyglutamates with Improved Pharmacokinetic Profiles as Excellent Candidates for Biomedical Applications", Molecular Pharmaceutics, vol. 12, Sep. 10, 2015, 3639-3649.
Extended European Search Report dated Aug. 1, 2016, EP Application No. 15382422.2.
Falk, et al., "Photoactivated Cationic Frontal Polymerization", Macromolecular Symposia, vol. 226, Jun. 20, 2005, 2005 97-107.
Inoue, et al., "Synthesis and Conformation of Star-Shaped Poly(γ-benzyl-L-glutamate)s on a Cyclotriphosphazene Core", Macromolecular Bioscience, vol. 3, Feb. 17, 2003, 26-33.
International Search Report dated Sep. 26, 2016, for PCT application No. EP2016/067554.
Isidro-Llobet et al., "Amino Acid-Protecting Groups", Chemical Reviews, vol. 109, Apr. 13, 2009, 2455-2504.
Karatzas, et al., "Synthesis of well-defined functional macromolecular chimeras based on poly(ethylene oxide) or poly(N-vinyl pyrrolidone)", Reactive & Functional Polymers, vol. 69, Jul. 2009, 435-440.
Klok, et al., "Star-Shaped Fluorescent Polypeptides", Journal of Polymer Science, Part A, vol. 39, Mar. 27, 2001, 1572-1583.
Ranganathan et al., "Design and synthesis of AB3-type (A=1,3,5-benzenetricarbonyl unit; B=Glu diOME or Glu₇ octa OMe) peptide dendrimers: Crystal structure of the first generation", Biopolymers, vol. 54, No. 4, Jan. 1, 2000, pp. 289-295.
Sulistio, et al., "Star polymers composed entirely of amino acid building blocks: a route towards stereospecific, biodegradable and hierarchically functionalized stars", Chemical Communications, vol. 47, Dec. 13, 2010, 1151-1153.
Written Opinion of the International Searching Authority dated Sep. 26, 2016, for PCT application No. EP2016/067554.
Aliferis, et al., "Synthesis of 3- and 4-Arm Star-Block Copolypeptides using Multifunctional Amino Initiators and High Vacuum Techniques", Macromolecular Symposia, vol. 240, Jul. 12, 2006, pp. 12-17.

* cited by examiner

*Primary Examiner* — Erich A Leeser
(74) *Attorney, Agent, or Firm* — Womble Bond Dickinson (US) LLP

(57) ABSTRACT

The invention relates to 3-arms star-shaped polypeptides derivatives which are able to self-assemble to form bioresponsive nanometric globular structures with controllable size and shape. These multivalent constructs also present the ability of disassemble under specific physiological conditions and of linking to at least one active agent so that they can be used as carries in biomedical applications.

22 Claims, 48 Drawing Sheets a)

b)

c)

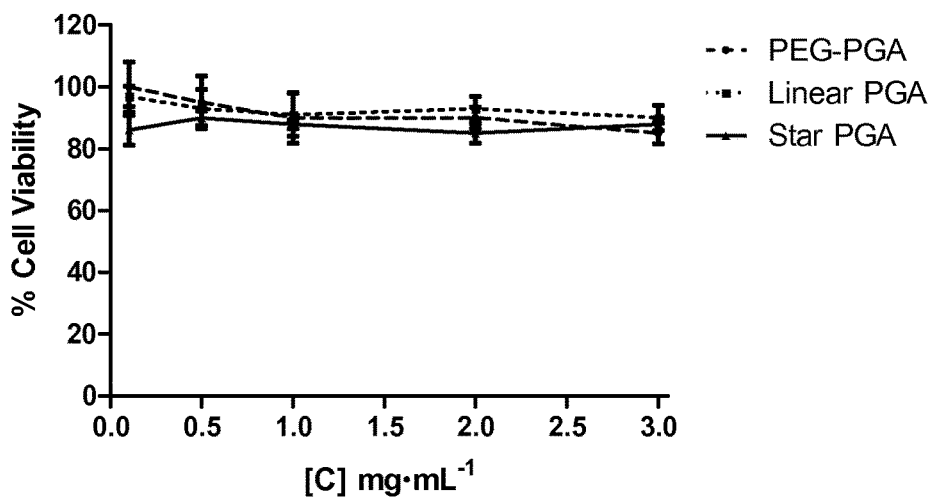
FIG. 25 cont.
a)
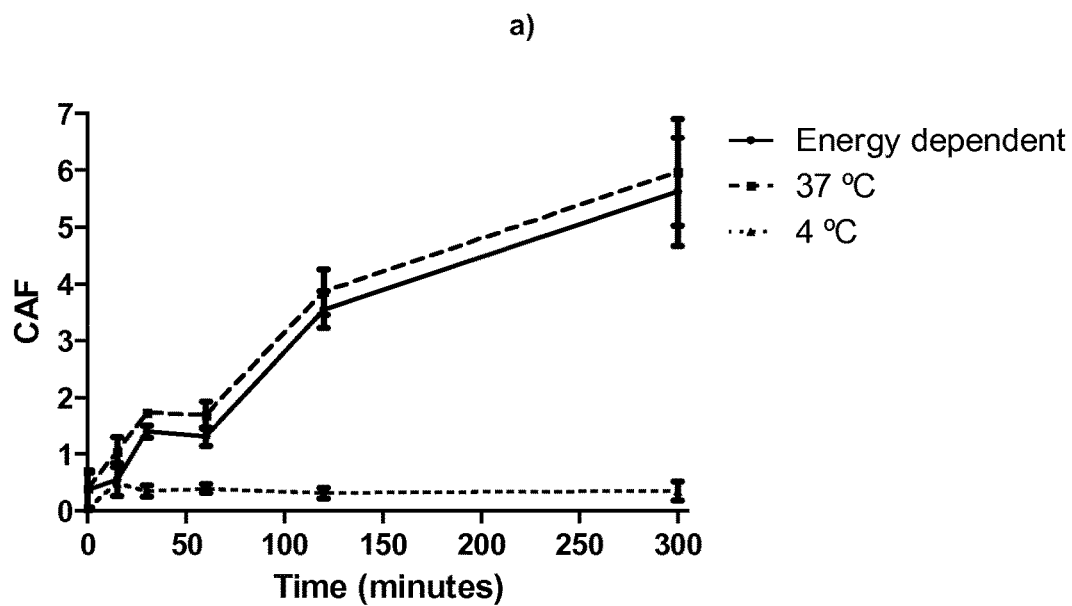

a)

CROSS-LINKED STAR-SHAPED SELF-ASSEMBLED POLYPEPTIDES AND ITS USE AS CARRIERS IN BIOMEDICAL APPLICATIONS

CROSS-REFERENCE TO RELATED APPLICATIONS

The present patent application is a national phase application of International Application No. PCT/EP2016/067554, filed Jul. 22, 2016, which claims priority to European Application No. 15382422.2, filed Aug. 7, 2015, the disclosures of which are incorporated herein by reference.

The invention relates to 3-arm star-shaped polypeptides derivatives which are able to self-assemble to form bioresponsive nanometric globular structures with controllable size and shape. These multivalent constructs also present the ability of disassemble under specific physiological conditions and of linking to at least one active agent so that they can be used as carries in biomedical applications.

BACKGROUND ART

There has been a considerable effort devoted to the development of new and more versatile polymeric architectures with specific and predictable properties to be used as targeted drug delivery systems. Such desirable features in these materials include: adjustable molecular weights (higher molecular weight (MW), to enhance passive targeting by the Enhanced Permeability and Retention (EPR) effect), predictable structure and conformation in solution, lower heterogeneity, and greater possibility for multivalency. Nevertheless, the design and synthesis of new polymeric constructs of relevant MW, together with their physicochemical characterization, conformational studies, and especially their potential for biological applications still remain to be fully exploited in this area. To this aim, polypeptide-based architectures can be considered suitable aspirants.

Star polypeptides are branched polymers, which consist of various linear chains linked to a central core. There are two main synthetic strategies described: the core-first approach (or multifunctional initiators or divergent approach) and the arm-first approach (or the use of multifunctional linking agents, or convergent approach). Various polypeptide-based star polymers have been synthesized over the years. For example, Klok et al. (*Journal of Polymer Science Part A: Polymer Chemistry* 2001, 39, (10), 1572-1583) used perylene derivatives with four primary amine groups as initiators to lead 4-arm poly(gamma-benzyl-L-glutamate) (PBLG) and poly(epsilon-benzyloxy-carbonyl-L-lysine) (PZLL) and Inoue et al. (*Macromolecular Bioscience* 2003, 3, (1), 26-33) used hexafunctional initiators for the synthesis of 6-arm PBLG star polymers both taking profit of the Ring Opening Polymerization (ROP) of N-Carboxyanhydrides (NCAs) techniques. Other examples are provided from the work of Aliferis et al. (*Macromolecular Symposia* 2006, 240, (1), 12-17) who used 2-(aminomethyl)-2-methyl-1,3-propanediamine as a trifunctional initiator for the synthesis of Poly(epsilon-carbobenzoxy-L-lysine-block-γ-benzyl-L-glutamate), P(BLL-b-BLG)$_3$ 3-arm star-block co-polypeptides; or the studies of Karatzas et al. (*Reactive and Functional Polymers* 2009, 69, (7), 435-440) in the synthesis of 4-arm poly(ethylene oxide)-block-poly(γ-benzyl-L-glutamate) (PEO-b-PBLG) hybrid star block co-polymers using 4-arm PEO stars end-functionalized with primary amines as initiators for the polymerization of gamma-Benzyl-L-Glutamate NCA (BLG-NCA) among others. Besides these two widely used approaches, a latest classification takes into account a new synthetic strategy. This approach consists on the reaction of living macroinitiators (MI) (also named macromonomers) with multifunctional molecules acting as cross-linkers giving rise to star-shaped architectures known as core cross-linked star (CCS) polymers (Chen et al. *Macromolecular Rapid Communications*, 2013, 34, 1507)

One of the most appealing properties, apart from their rheological characteristics and thermoplastic character, is their self-assembly behavior that can be promoted in solution by the presence of functional moieties along the chain arms (in the case of homopolymers) or by using selective solvents (in the case of star-blocks or miktoarm stars). Micellar structural parameters such as critical micellar concentration (CMC), aggregation number, core and shell dimensions, overall micelle concentration as well as thermodynamics and kinetics of micellization of complex structures, such as star-block copolymers and miktoarm stars, have been poorly investigated if compared to linear analogues. In general basis, star structures have higher CMC values and consequently, lower aggregation numbers than their linear block copolymers counterparts.

Overall, it is well-known that macromolecular architecture is a key parameter for the tuning of micellar behavior and properties, and thus, it must be well-considered for the design of new materials and their potential biological applications, in particular as drug delivery systems.

Moreover, despite the growing interest in the development of hybrid and peptide-based star polymers as prospective advanced materials for biological applications, only recently, they have been explored as drug delivery systems. For instance, Sulistio et al. (*Chem. Commun*, 2011, 47, 1151-1153), synthesized highly functionalized water soluble core cross-linked star (CCS) polymers having degradable cores synthesized entirely from amino acid building blocks which are capable of encapsulating water-insoluble drugs. These types of stars were able to entrap hydrophobic drugs, such as the anti-cancer drug pirarubicin, through physical interactions with pyrene moieties of the core. Moreover, due to the presence of disulfide bonds at the core, the stars could also be cleaved by reducing agents such as dithiothreitol, yielding redox-sensitive polymers.

DESCRIPTION OF THE INVENTION

The present invention relates to a family of 3-arms star shaped polypeptide derivatives consisting of a 1,3,5-Benzenetricarboxamide related central core employed as the initiator for the ring opening polymerization of N-carboxyanhydride monomers and 3 polypeptide backbone arms. These systems undergo a self-assembly process yielding structures in the nanometer range (4-300 nm in radius). Post-polymerization modifications of the polypeptide residues leads to the introduction of cross-linking groups convenient for the stabilization of the resulting self-assembled nanostructures which can be further functionalized with the introduction of one or more active agents for multiple applications in biomedicine.

A first aspect of the present invention is related to a compound of formula (I) below, comprising homo-polypeptides or random or block co-polypeptides:

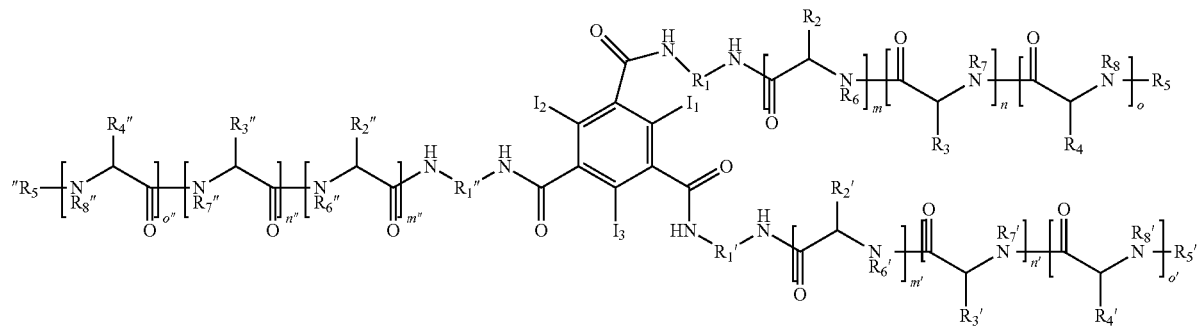
(I)

or its salts, solvates or isomers, wherein:

m, m', m", n, n', n", o, o' and o" are integers independently selected from 0 to 500, wherein at least one of them is ≥1;

$R_6$ to $R_8$, $R_{6'}$ to $R_{8'}$ and $R_{6''}$ to $R_{8''}$ are independently selected from H and methyl;

$I_1$ to $I_3$ are independently selected from the group consisting of H; halogen; Deuterium; and $(C_1-C_{20})$-alkyl;

each $R_2$ to $R_4$, $R_{2'}$ to $R_{4'}$, and $R_{2''}$ to $R_{4''}$ represents the side residues of amino acids in the polypeptidic backbone obtained by means of the ROP of NCAs, being either block or random copolypeptides, and each of them is independently selected from the group consisting of:

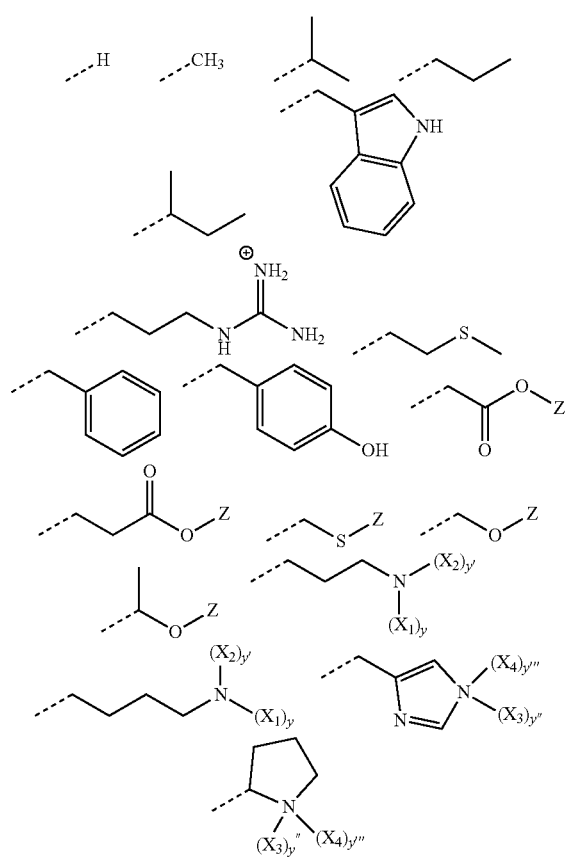

$X_1$ and $X_2$ are independently selected from the group consisting of H; N; $NH_2$; and Z;

$X_3$ and $X_4$ are independently selected from the group consisting of H; and Z;

y and y' are integers between 0 and 3; and y+y'=2 or 3;

y" and y"' are integers between 0 and 2; and y+y'=1 or 2

Z is selected from the group consisting of H; metallic counterion; inorganic counterion; and an amino acid protecting group. In the present invention, the expression "amino acid protecting group" refers to any chemical functional group which can be introduced to the amino acid of the molecule by chemical modification to obtain chemoselectivity in a subsequent chemical reaction. It plays an important role in multistep organic synthesis. The person skilled in the art knows the amino acid protecting groups, some of them are detailed in *Chem Rev* 2009, 109, 2455-2504, incorporated here by reference.

$R_1$, $R_{1'}$ and $R_{1''}$ are radicals independently selected from the group consisting of:

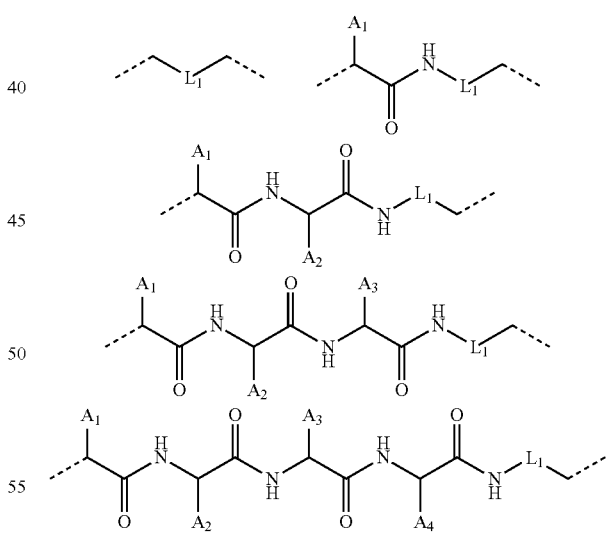

$A_1$, $A_2$, $A_3$ and $A_4$ denote the side residues of amino acids, and are independently selected from the group as defined for $R_2$ to $R_4$, $R_{2'}$ to $R_{4'}$, and $R_{2''}$ to $R_{4''}$;

$L_1$ is a radical selected from the group consisting of $(C_1-C_{500})$-alkyl, wherein one or more H is optionally substituted by: (1) $(C_3-C_{30})$-cycloalkyl, (2) a C-radical derived from a ring system with 1-6 rings, each ring being independently saturated, partially unsaturated or aromatic, the rings being isolated or fused and having 3-20 members each member independently selected from the group consisting of C, CH, CH$_2$, CO, N and NH, (3) OH, (4) NR$_a$R$_b$, (5) ONR$_c$R$_d$, (6) CN, (7) halide, (8) SH$_2$, (9) SR$_e$R$_f$, (10) N(H)NH$_2$, (11) R$_g$COR$_h$, (12) COOR$_i$, (13) CON(R$_j$)(R$_k$), (14) R$_l$N(R$_m$)CON(R$_n$)$_2$, (15) (C$_1$-C$_{30}$)-alkene, (16) (C$_1$-C$_{30}$)-alkyne, (17) N$_3$, (18) R$_o$CH(OR$_p$)(OR$_q$), (19) R$_r$CH(SR$_s$)(SR$_t$), (20) R$_u$Boron(OR$_v$)(OR$_w$), (21) COR$_x$; and wherein one of more C are independently replaced by (C$_3$-C$_{30}$)-cycloalkyl, aryl, aryl-(C$_1$-C$_{30}$)-alkyl, NR$_y$R$_z$, CO, O, S, Boron, halide, P and (O—CH$_2$—CH$_2$)$_B$;

B is an integer between 1 and 500;

R$_a$, R$_b$, R$_c$, R$_d$, R$_e$, R$_f$, R$_h$, R$_i$, R$_j$, R$_k$, R$_m$, R$_n$, R$_p$, R$_q$, R$_s$, R$_t$, R$_v$, R$_w$, R$_x$, R$_y$ and R$_z$ are radicals independently selected from the group consisting of H; (C$_1$-C$_{30}$)-alkyl; (C$_1$-C$_{30}$)-alkylphenyl; phenyl (C$_1$-C$_{30}$)-alkyl; and (C$_3$-C$_8$)-cycloalkyl, wherein one or more carbons are optionally substituted by an heteroatom selected from the group consisting of O; S; F; N; NH; P; and CO;

R$_g$, R$_l$, R$_o$, R$_r$ and R$_u$ are radicals independently selected from the group consisting of (C$_1$-C$_{30}$)-alkyl; (C$_1$-C$_{30}$)-alkylphenyl; phenyl; (C$_1$-C$_{30}$)-alkyl; and (C$_3$-C$_8$)-cycloalkyl, wherein one or more carbons are optionally substituted by an heteroatom selected from the group consisting of O; S; F; N; NH; P; and CO;

R$_5$, R$_{5'}$, and R$_{5''}$ represent end-capping motif at the N-terminal position. R$_5$, R$_{5'}$ and R$_{5''}$ are radicals independently selected from the group consisting of H; and (C$_1$-C$_{500}$)-alkyl, wherein one or more H is optionally substituted by: (1) (C$_3$-C$_{30}$)-cycloalkyl, (2) a C-radical derived from a ring system with 1-6 rings, each ring being independently saturated, partially unsaturated or aromatic, the rings being isolated or fused and having 3-20 members each member independently selected from the group consisting of C, CH, CH$_2$, CO, N and NH, (3) OH, (4) NR$_a$R$_b$, (5) ONR$_c$R$_d$, (6) CN, (7) halide, (8) SH$_2$, (9) SR$_e$R$_f$, (10) N(H)NH$_2$, (11) R$_g$COR$_h$, (12) COOR$_i$, (13) CON(R$_j$)(R$_k$), (14) R$_l$N(R$_m$)CON(R$_n$)$_2$, (15) (C$_1$-C$_{30}$)-alkene, (16) (C$_1$-C$_{30}$)-alkyne, (17) N$_3$, (18) R$_o$CH(OR$_p$)(OR$_q$), (19) R$_r$CH(SR$_s$)(SR$_t$), (20) R$_u$Boron(OR$_v$)(OR$_w$), (21) COR$_x$; and wherein one of more C are independently replaced by (C$_3$-C$_{30}$)-cycloalkyl, aryl, aryl-(C$_1$-C$_{30}$)-alkyl, NR$_y$R$_z$, CO, O, S, Boron, halide, P and (O—CH$_2$—CH$_2$)$_B$;

B is an integer between 1 and 500;

R$_a$, R$_b$, R$_c$, R$_d$, R$_e$, R$_f$, R$_h$, R$_i$, R$_j$, R$_k$, R$_m$, R$_n$, R$_p$, R$_q$, R$_s$, R$_t$, R$_v$, R$_w$, R$_x$, R$_y$ and R$_z$ are radicals independently selected from the group consisting of H; (C$_1$-C$_{30}$)-alkyl; (C$_1$-C$_{30}$)-alkylphenyl; phenyl (C$_1$-C$_{30}$)-alkyl; and (C$_3$-C$_8$)-cycloalkyl, wherein one or more carbons are optionally substituted by an heteroatom selected from the group consisting of O; S; F; N; NH; P; and CO;

R$_g$, R$_l$, R$_o$, R$_r$ and R$_u$ are radicals independently selected from the group consisting of (C$_1$-C$_{30}$)-alkyl; (C$_1$-C$_{30}$)-alkylphenyl; phenyl; (C$_1$-C$_{30}$)-alkyl; and (C$_3$-C$_8$)-cycloalkyl, wherein one or more carbons are optionally substituted by an heteroatom selected from the group consisting of O; S; F; N; NH; P; and CO.

In the present invention, the term "alkyl" refers to linear or branched hydrocarbonated chain radicals, saturated, partially saturated or insaturated. In the present invention the term "cycloalkyl" refers to a cyclic hydrocarbonated radical, saturated, unsaturated or partially saturated or aromatic.

In an alternative embodiment, the present invention relates to the compound of formula (I), wherein:
I$_1$, I$_2$ and I$_3$, are radicals independently selected from the group consisting of H; Deuterium; and F;

R$_5$, R$_{5'}$ and R$_{5''}$ are identical between them, and selected from the group consisting of H; CO—(C$_1$-C$_{20}$)-alkyl; CONH—(C$_1$-C$_{20}$)-alkyl; and pyroglutamate.

In an alternative embodiment, the present invention also relates to the compound of formula (I) as defined in any of the above embodiments, wherein:

R$_2$=R$_{2'}$=R$_{2''}$, R$_3$=R$_{3'}$=R$_{3''}$, and R$_4$=R$_{4'}$=R$_{4''}$, and each of them is independently selected from the group consisting of:

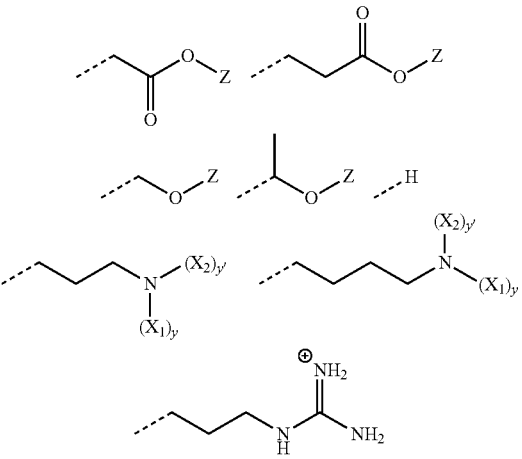

X$_1$ and X$_2$ are independently selected from the group consisting of H; N; —NH$_2$; and Z;

y and y' are integers between 0 and 3; and y+y'=2 or 3;

R$_1$=R$_{1'}$=R$_{1''}$ is selected from the following groups:

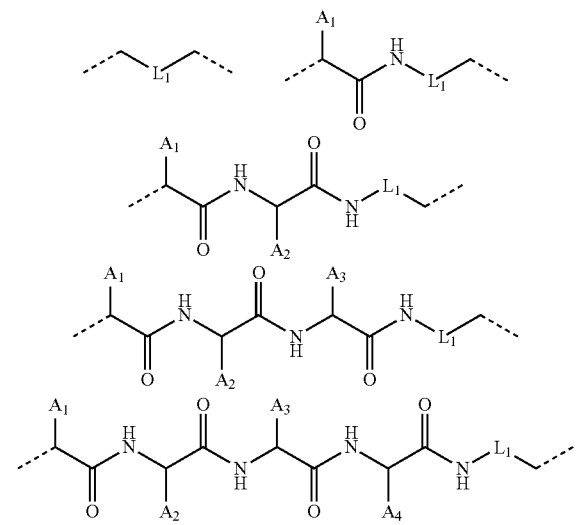

A$_1$, A$_2$, A$_3$ and A$_4$ denote the side residues of hydrophobic amino acids and they are selected from the following groups or combinations thereof:

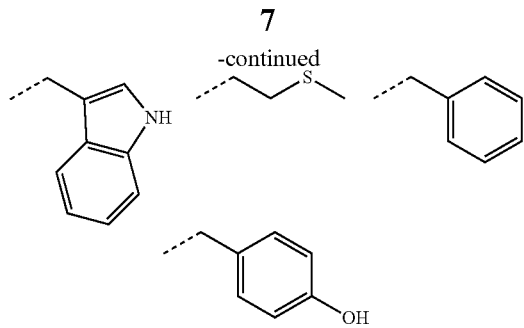

$L_1$ is defined as in any of the above embodiments.

In a particular embodiment of any of the previous embodiments, m, m', m'', n, n', n'', o, o' and o'' are integers independently selected from 0 to 500, wherein at least one of them is ≥1.

In a particular embodiment of any of the above embodiments, the polypeptidic backbone of the compound of formula (I) of the first aspect of the invention is selected from the group consisting of: arginine, ornithine, lysine, sarcosine, and serine.

In another particular embodiment of any of the above embodiments, the polypeptidic backbone of the compound of formula (I) of the first aspect of the invention is a di-block polypeptide selected from the group consisting of: serine-sarcosine, serine-lysine, glutamic-serine, serine-ornithine, serine-arginine, lysine-sarcosine, sarcosine-ornithine, sarcosine-arginine, ornithine-arginine, glutamic-ornithine, glutamic-arginine, glutamic-lysine, glutamic-sarcosine, phenylalanine-glutamic, and phenylalanine-lysine, phenylalanine-ornithine, phenylalanine-arginine, phenylalanine-sarcosine, and serine-phenylalanine.

In a particular embodiment, the polypeptidic backbone of the compound of formula (I) of the first aspect of the invention is polyglutamate as depicted below:

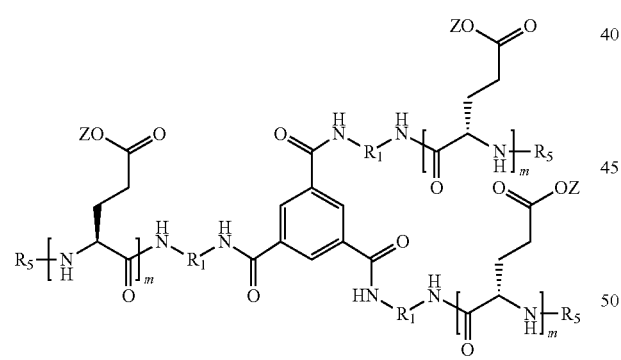

or its salts, solvates or isomers, wherein:
m is an integer selected from 1 to 500;
Z is selected from the group consisting of H; metallic counterion; inorganic counterion; and an amino acid protecting group;
$R_1$ is selected from the following groups:

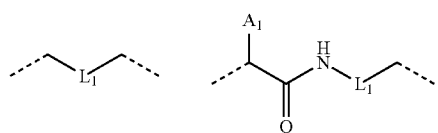

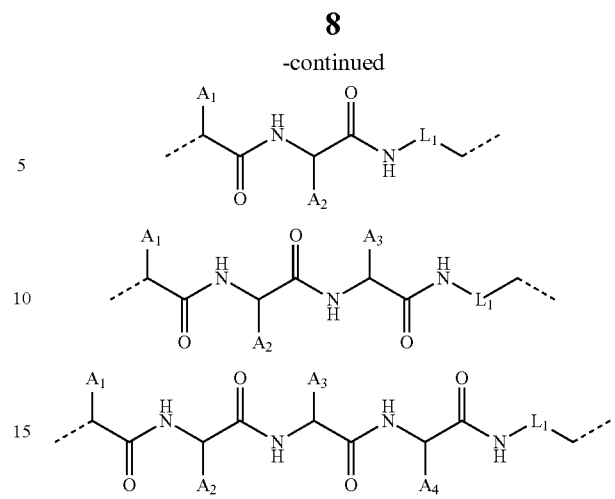

$A_1$, $A_2$, $A_3$ and $A_4$ denote the side residues of hydrophobic amino acids and they are selected from the following groups or combinations thereof:

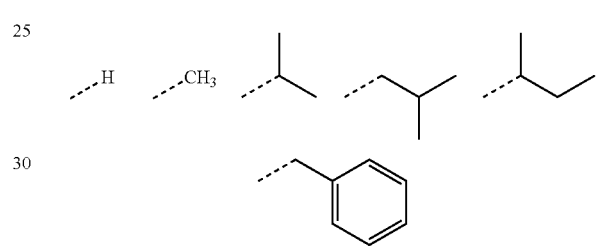

$L_1$ represents a spacer selected from the following groups:

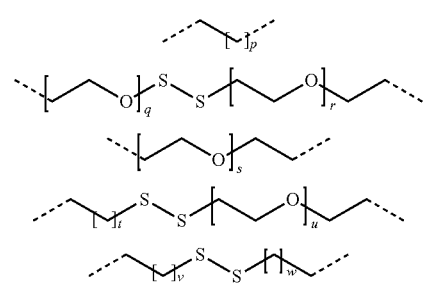

p, q, r, s, t, u, v, and w, are integers selected from and 1 to 300 respectively;

and, ----- the bond which links these groups to the rest of the molecule.

In a particular embodiment, the $R_1$ radical of the compound of the previous particular embodiment is selected from the following groups:

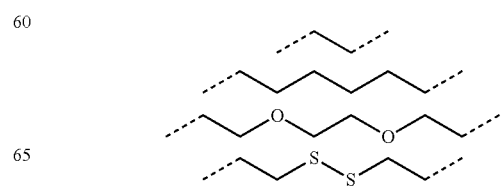

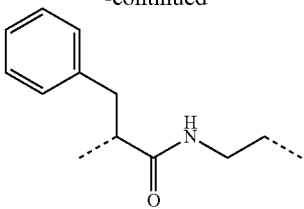

The second aspect of the invention relates a compound comprising homopolypeptides or random or block co-polypeptides of formula (II) below:

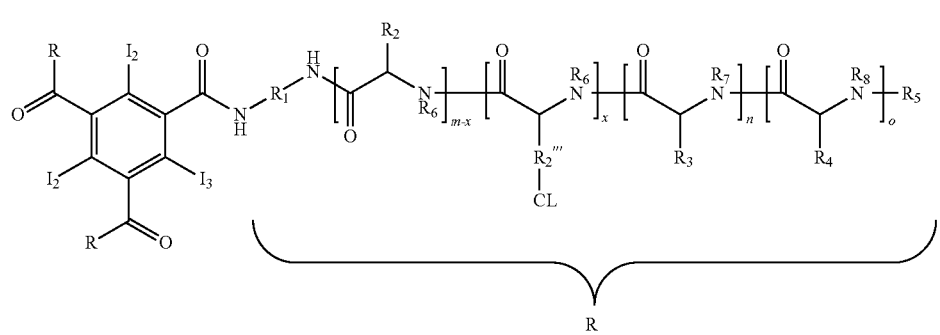

or its salts, solvates or isomers wherein:
$R_1$ to $R_8$, $I_1$ to $I_3$, n, and o, are defined in the first embodiment;
m is an integer number between 2-500;
x is a number from 0.01*m to 0.5*m;
$R_{2'''}$ is a radical selected from the group consisting of:

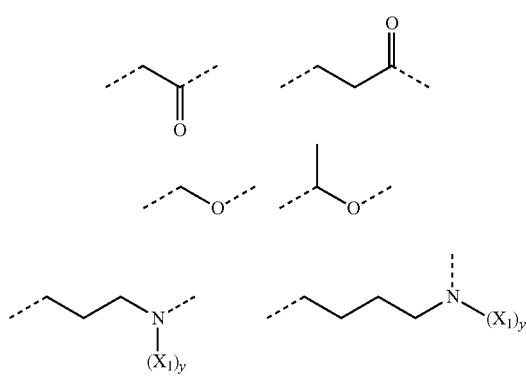

$X_1$ is H;
y is 0 or 1;
CL is a radical selected from the group consisting of an ($C_1$-$C_{500}$)-alkyl, wherein one or more H is optionally substituted by: (1) ($C_3$-$C_{30}$)-cycloalkyl, (2) a C-radical derived from a ring system with 1-6 rings, each ring being independently saturated, partially unsaturated or aromatic, the rings being isolated or fused and having 3-20 members each member independently selected from the group consisting of C, CH, $CH_2$, CO, N and NH, (3) OH, (4) $NR_aR_b$, (5) $ONR_cR_d$, (6) CN, (7) halide, (8) $SH_2$, (9) $SR_eR_f$, (10) $N(H)NH_2$, (11) $R_gCOR_h$, (12) $COOR_i$, (13) $CON(R_j)(R_k)$,

(14) $R_jN(R_m)CON(R_n)_2$, (15) ($C_1$-$C_{30}$)-alkene, (16) ($C_1$-$C_{30}$)-alkyne, (17) $N_3$, (18) $R_oCH(OR_p)(OR_q)$, (19) $R_rCH(SR_s)(SR_t)$, (20) $R_uBoron(OR_v)(OR_w)$, (21) $COR_x$; and wherein one of more C are independently replaced by ($C_3$-$C_{30}$)-cycloalkyl, aryl, aryl-($C_1$-$C_{30}$)-alkyl, $NR_yR_z$, CO, O, S, Boron, halide, P and (O—$CH_2$—$CH_2$)$_B$;
B is an integer between 1 and 500;
$R_a$, $R_b$, $R_c$, $R_d$, $R_e$, $R_f$, $R_h$, $R_i$, $R_j$, $R_k$, $R_m$, $R_n$, $R_p$, $R_q$, $R_s$, $R_t$, $R_v$, $R_w$, $R_x$, $R_y$ and $R_z$ are radicals independently selected from the group consisting of H; ($C_1$-$C_{30}$)-alkyl; ($C_1$-$C_{30}$)-alkylphenyl; phenyl ($C_1$-$C_{30}$)-alkyl; and ($C_3$-$C_8$)-cycloalkyl, wherein one or more carbons are optionally substituted by an heteroatom selected from the group consisting of O; S; F; N; NH; P; and CO;
$R_g$, $R_l$, $R_o$, $R_r$ and $R_u$ are radicals independently selected from the group consisting of ($C_1$-$C_{30}$)-alkyl; ($C_1$-$C_{30}$)-alkylphenyl; phenyl; ($C_1$-$C_{30}$)-alkyl; and ($C_3$-$C_8$)-cycloalkyl, wherein one or more carbons are optionally substituted by an heteroatom selected from the group consisting of O; S; F; N; NH; P; and CO.

In a particular embodiment, the present invention relates to the compound of formula (II) as defined in the second aspect of the invention, wherein:
$I_1$, $I_2$ and $I_3$, are radicals independently selected from the group consisting of H; Deuterium; and F;
$R_5$ is selected from the group consisting of H; CO—($C_1$-$C_{20}$)-alkyl; CONH—($C_1$-$C_{20}$)-alkyl; and pyroglutamate.

In a particular embodiment the present invention relates to the compound of formula (II) as defined in the second aspect of the invention or in the previous embodiment, wherein:
$R_{2'''}$ is selected from the group consisting of:

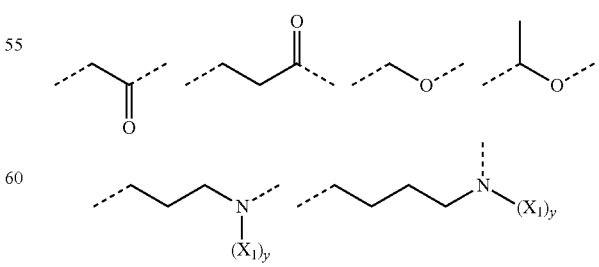

$X_1$ is H;
y is 0 or 1;

CL is selected from the group consisting of:

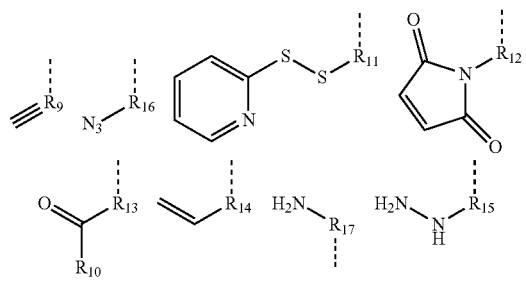

$R_9$, and $R_{11}$ to $R_{17}$ are independently selected from the group consisting of:

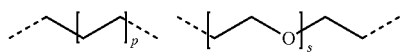

p and s are integers independently selected from 0 to 500;
$R_{10}$ is selected from H and $(C_1$-$C_4)$-alkyl.

In particular embodiment of any of the embodiments of the second aspect of the invention, m is an integer between 2 and 50. In another particular embodiment of any of the embodiments of the second aspect of the invention, p and s are independent integers selected from 0 to 50.

In a particular embodiment, the polypeptidic backbone of the compound of formula (II) of the second aspect of the invention is selected from the group consisting of: arginine, ornithine, lysine, sarcosine, and serine.

In another particular embodiment, the polypeptidic backbone of the compound of formula (II) of the second aspect of the invention is a di-block polypeptide selected from the group consisting of: serine-sarcosine, serine-lysine, glutamic-serine, serine-ornithine, serine-arginine, lysine-sarcosine, sarcosine-ornithine, sarcosine-arginine, ornithine-arginine, glutamic-ornithine, glutamic-arginine, glutamic-lysine, glutamic-sarcosine, phenylalanine-glutamic, and phenylalanine-lysine, phenylalanine-ornithine, phenylalanine-arginine, phenylalanine-sarcosine, and serine-phenylalanine.

In a particular embodiment, the polypeptidic backbone of the compound of formula (II) of the second aspect of the invention is polyglutamate, as depicted below:

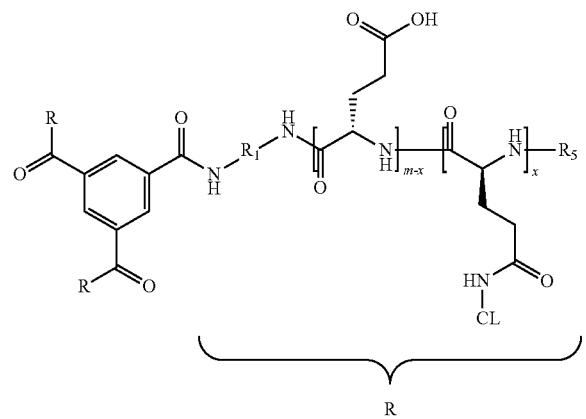

or its salts, solvates or isomers wherein:

m and $R_1$ are defined as in the particular embodiment of the first aspect of the invention;
$R_5$ is defined as in the first aspect of the invention, and CL is selected from the following groups:

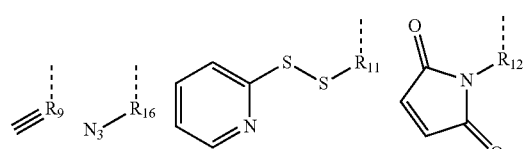

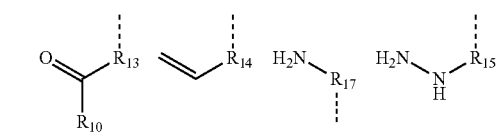

$R_9$, and $R_{11}$ to $R_{17}$ are independently selected from the group consisting of:

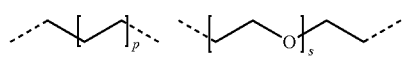

p and s are integers independently selected from 0 to 500;
$R_{10}$ is selected from H and $(C_1$-$C_4)$-alkyl.

In a particular embodiment of the previous particular embodiment, $R_1$ is selected from the following groups:

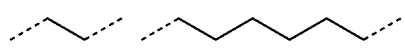

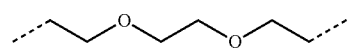

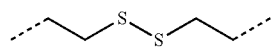

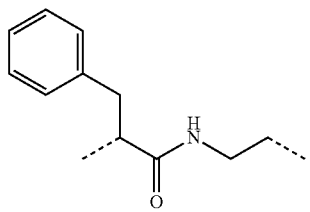

The third aspect of the present invention relates to a cross-linked self-assembled star polymer comprising a recurring unit of formula (III) below:

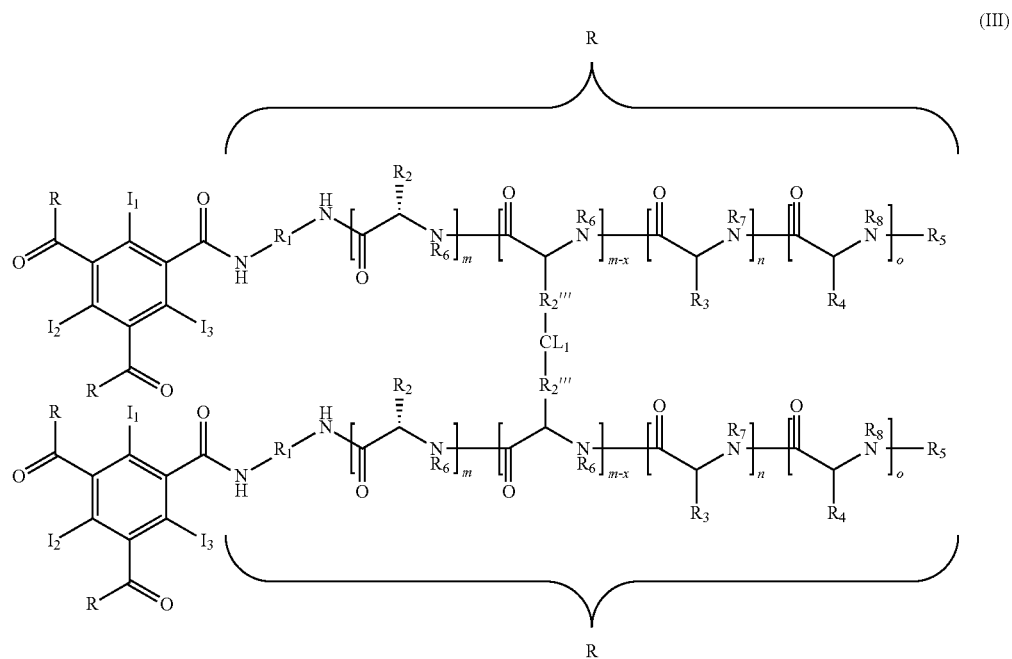

(III)

or its salts, solvates or isomers wherein:

$R_1$ to $R_8$, $I_1$, to $I_3$, m, n and o are defined as in the first aspect of the invention;

x is defined as in the second aspect of the invention;

$R_{2'''}$ is selected from the group consisting of:

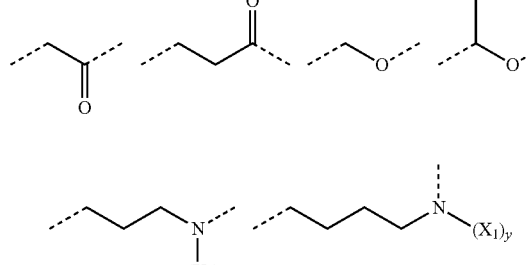

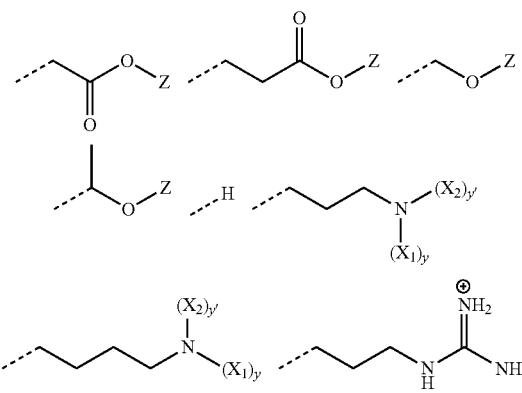

$X_1$ and y are defined as in the second aspect of the invention;

$CL_1$ is defined as CL the second aspect of the invention.

In a particular embodiment, the present invention relates to the cross-linked self-assembled star polymer of formula (III), as defined in the third aspect of the invention wherein:

$I_1$, $I_2$, and $I_3$, are radicals independently selected from the group consisting of H; Deuterium; and F;

$R_5$ is selected from the group consisting of H; CO—($C_1$-$C_{20}$)-alkyl; CON(H)—($C_1$-$C_{20}$)-alkyl; and pyroglutamate.

In another particular embodiment, the present invention relates to the cross-linked self-assembled star polymer according to the third aspect of the invention or to the previous preferred embodiment, wherein:

each $R_2$, $R_3$, and $R_4$ is independently selected from the group consisting of:

$X_1$ and $X_2$ are defined as in the first aspect of the invention;

y and y' are defined as in the first aspect of the invention;

$R_1$ is selected from the following groups:

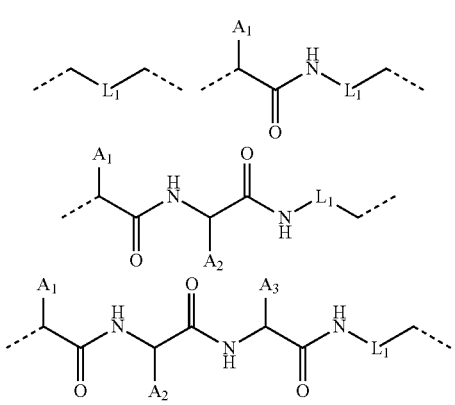

-continued

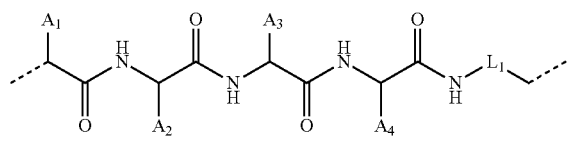

$A_1$, $A_2$, $A_3$ and $A_4$ denote the side residues of hydrophobic amino acids and they are selected from the following groups or combinations thereof:

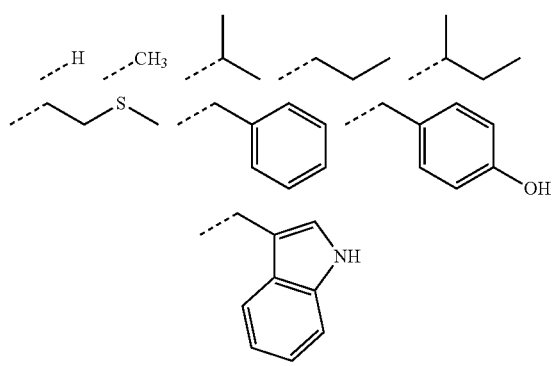

$L_1$ represents a spacer selected from the following groups:

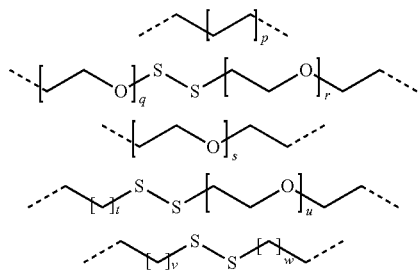

p, q, r, s, t, u, v, and w, are integers selected from and 1 to 300 respectively;
and, ----- the bond which links these groups to the rest of the molecule.

In another particular embodiment, the present invention relates to the self-assembled star polymer according to the third embodiment of the invention or any of the two previous embodiments, wherein:
$R_{2'''}$ is selected from the group consisting of:

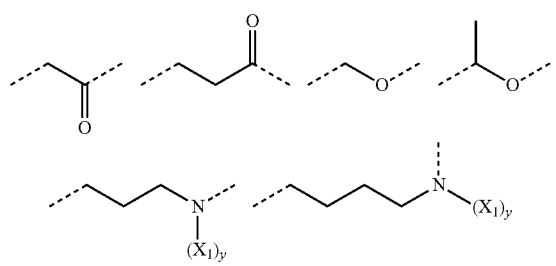

$CL_1$ is selected from the group consisting of:

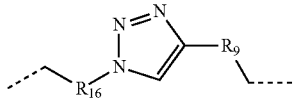

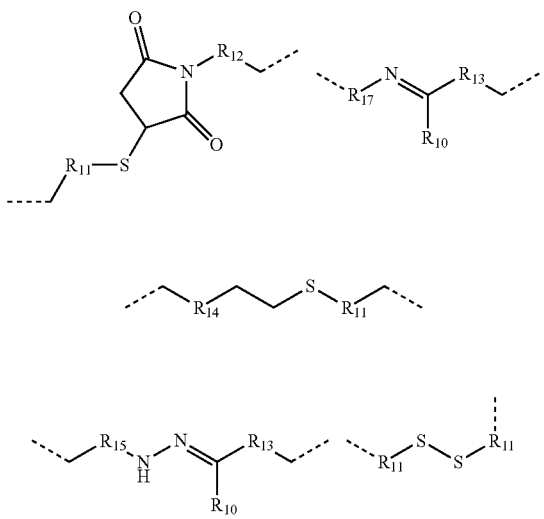

$R_9$, and $R_{11}$ to $R_{17}$ are selected from the group consisting of:

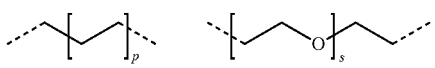

p and s are integers independently selected from 0 to 500;
$R_{10}$ is selected from H and $(C_1$-$C_4)$-alkyl.

In a particular embodiment, the polypeptidic backbone of the cross-linked self-assembled star polymer comprising a recurring unit of formula (III) is selected from the group consisting of: arginine, ornithine, lysine, sarcosine and serine.

In another particular embodiment, the polypeptidic backbone of the cross-linked self-assembled star polymer comprising a recurring unit of formula (III) is a di-block polypeptide selected from the group consisting of: serine-sarcosine, serine-lysine, glutamic-serine, serine-ornithine, serine-arginine, lysine-sarcosine, sarcosine-ornithine, sarcosine-arginine, ornithine-arginine, glutamic-ornithine, glutamic-arginine, glutamic-lysine, glutamic-sarcosine, phenylalanine-glutamic, and phenylalanine-lysine, phenylalanine-ornithine, phenylalanine-arginine, phenylalanine-sarcosine, and serine-phenylalanine.

In a particular embodiment, the polypeptidic backbone of the cross-linked self-assembled star polymer comprising a recurring unit of formula (III) is polyglutamate as depicted below:

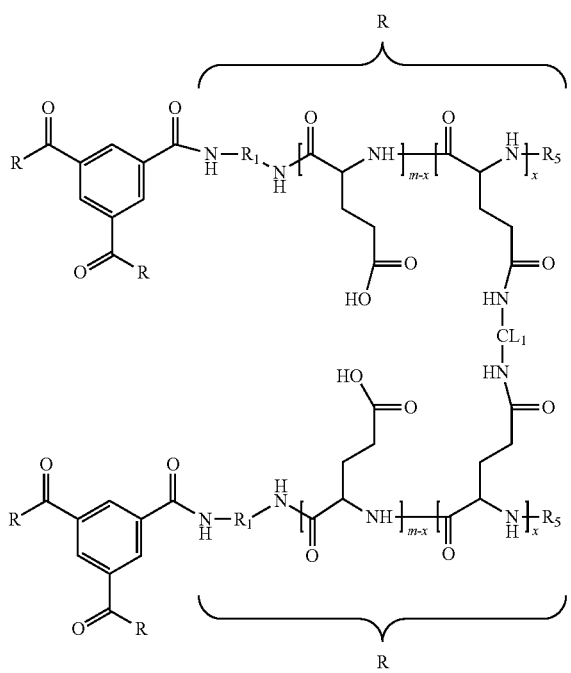

wherein:
$R_1$, $R_5$, m, and x are defined as in the second aspect of the invention where the polypeptidic backbone is polyglutamate;
$CL_1$ is selected from the following groups:

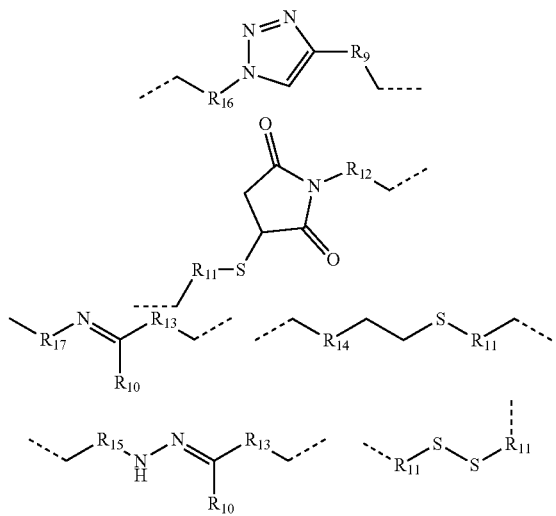

$R_9$ to $R_{17}$ are defined as in the first particular embodiment of the second aspect of the invention.

In another particular embodiment, the $R_1$ radical of the cross-linked self-assembled star polymer of the previous particular embodiment is selected from the following groups:

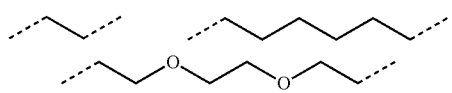

The compounds and the cross-linked self-assembled star polymer of the present invention as defined in any of the previous embodiments or aspects of the invention may include isomers, depending on the presence of multiple bonds (for example, Z, E), including optical isomers or enantiomers, depending on the presence of chiral centers. The individual isomers, enantiomers or diastereoisomers, and the mixtures thereof, fall within the scope of the present invention. The individual enantiomers or diastereoisomers, and the mixtures thereof, may be separated by means of any conventional technique well known to the person skilled in the art.

The compounds and the cross-linked self-assembled star polymer of the present invention may be in crystalline form as free ones or as solvates, and both forms are intended to be included within the scope of the present invention. In this regard, the term "solvate", as used herein, includes both pharmaceutically acceptable solvates, i.e. solvates of the compound with the formula (I), or (II) or the cross-linked self-assembled star polymer (III) that may be used in the preparation of a medicament, and pharmaceutically unacceptable solvates, which may be useful in the preparation of pharmaceutically acceptable solvates or salts. The nature of the pharmaceutically acceptable solvate is not critical, provided that it is pharmaceutically acceptable. In a particular embodiment, the solvate is a hydrate. The solvates may be obtained by conventional solvation methods that are well-known to persons skilled in the art. Except as otherwise specified, the compounds of the present invention also include compounds that differ only in the presence of one or more isotope-enriched atoms. Examples of isotope-enriched atoms, without limitation, are deuterium, tritium, $^{13}C$ or $^{14}C$, or a nitrogen atom enriched in $^{15}N$.

A fourth aspect of the invention relates to a conjugate comprising the compounds of formula (I) or (II) as previously defined, or the self-assembled star polymer of formula (III) as previously defined, and at least an active agent linked to the compound or the self-assembled star polymer. The at least active agent(s) can be covalently bound directly or by one or more linkers, or alternatively the at least active agent(s) can be non-covalently bound to the compound or the self-assembled star polymer. In a preferred embodiment, the at least active agent is (are) covalently linked to the polypeptidic backbone through the amino acid side residue via amide, ester, anhydride bonding or through a linker that include one or more functional groups, including without limitation, alkynes, azides, reactive disulfides, maleimides, hydrazide, hydrazones, Schiff bases, acetal, aldehydes, carbamates, and reactive esters. In an alternative embodiment the covalent link is a bioresponsive one. The expression "bioresponsive one" refers to a chemical link cleavable under specific physiological or external triggers (for example, and without limitation, pH, reactive oxygen species, reductive environment, specific enzymes, glucose, light, temperature, etc.).

In the present invention the expression "active agent" refers to an active ingredient and an imaging agent.

Preferably, the active ingredient is selected from small agents (i.e. pharmaceutical active ingredients or drugs) to biomolecules (i.e. peptides, (apolipo)proteins, antibodies, Fab or fragment antigen-binding, and nucleic acids). Examples of active ingredient include, without limitation, antibody, antigen, (arginine-glycine-aspartate (RGD)) peptide, oligosaccharide, bisphosphonate, aptamer, polysaccharide, hyaluronic, chondroitin sulphate, double stranded oligonucleotide (DNA), siRNA, fibronectin, and folate.

In preferred embodiment, the active ingredient is selected from the group consisting of anticancer agent, antimetastatic, agent anti-inflammatory agent, antioxidant, neuroprotective agent, immunostimulant agent, agent capable to trigger tissue repair and/or regeneration, antioxidants, anti-apoptotic, proapoptotic, anti-amyloidotic agent, and plaque/protein aggregates disrupting agents.

In a still preferred embodiment, the active ingredient is selected from the group consisting of: vincristine, vinblastine, amiloride, chloroquine, blafiomycyn, fasudil, bisphosphonate, primaquine, meclofenamate, tonabersat, disulfiram, cyclophosphamide, paclitaxel, dendrotoxin, doxorubicine, methotrexate, epirubicine, dinaciclib, buparlisib, palbociclib, veliparib, megestrol, examestane, goserelin, tamoxifen, fulvestrant, trastuzumab, lapatinib, pertuzumab, selegiline, rasagiline, ladostigilM30, curcumin, demethoxycurcumin, and bisdemethoxycurcumin.

In the present invention the expression, "imaging agent" refers to any substance that is used as a label, or that enhances specific structures in any imaging technique. An imaging agent, hence, includes optical imaging agent, magnetic resonance imaging agent, radioisotope, and contrast agent. Examples, without limitation, of optical imaging agent are acridine dye, a coumarin dye, a rhodamine dye, a xanthene dye, a cyanine dye, and a pyrene dye, Texas Red, Alexa Fluor® dye, BODIPY® dye, Fluorescein, Oregon Green® dye, and Rhodamine Green™ dye, which are commercially available or readily prepared by methods known to those skilled in the art. Examples of imaging agents appropriate for the present invention include, but are not limited to, transition metals and radioactive transition metals chelated to chelating agents, for instance DTPA (diethylene triamine pentaacetic acid), DOTA (1,4,7,10-Tetraazacyclododecane-1,4,7,10-tetraacetic acid) and NOTA (1,4,7-Triazacyclononane-1,4,7-triacetic acid).

In an alternative embodiment, the conjugate defined in the fourth aspect of the invention or any embodiment thereto, comprises an amount of the at least an active agent in the range of 1 to 70% w/w based on the mass ratio of the active agent to the conjugate. In a preferred embodiment, the range is of 1 to 50% w/w. In a still more preferred embodiment, the conjugate comprises an amount of the agent in the range of 1 to 25% w/w.

A fifth aspect of the invention relates to a pharmaceutical, diagnostic or theranostic composition comprising at least one conjugate as defined in the fourth aspect of the invention, or any embodiment together with one or more appropriate pharmaceutical or diagnostically acceptable excipients.

A sixth aspect of the invention relates the conjugate for use as a medicament, in diagnostics or a combination of both (theranostics).

This aspect could also be formulated as a method for the prophylaxis and/or treatment of a disease which comprises administering to mammals in need of such treatment or diagnostic, an effective amount of any of the conjugates of the present invention, together with one or more appropriate pharmaceutically acceptable excipients and/or carriers. This aspect could also be formulated as a method for the diagnosis of a disease in an isolated sample of a subject, the method comprises administering to said subject an effective amount of the any of the conjugate having one or more imaging agents as defined above to the isolated sample of the subject. The detection of these imaging agents can be carried out by well-known techniques such as imaging diagnostic techniques. Examples of imaging diagnostic techniques suitable for the present invention include, but not limited to, are magnetic resonance imaging (MRI), X-ray, positron emission tomography (PET), single-photon emission computed tomography (SPECT), fluorescence microscopy, and in vivo fluorescence.

In a particular embodiment of this aspect, the conjugate for use in the prevention and/or treatment of neurodegenerative disorder, neurological disease, cancer, infectious disease, disorder related to aging, neuro-inflammation, demyelinating disorder, multiple sclerosis, ischemic disorder, ischemia-reperfusion damage, amyloydotic disease, cardiomyopathy, spinal cord injury, immune disorder, inflammatory disorders, rare disease, wound healing and lysosomal storage disease.

The neurodegenerative diseases may be selected from the list that comprises, without being limited thereto, Alzheimer's disease, Parkinson's disease, amyotrophic lateral sclerosis, cerebral ischaemia, post-encephalitic Parkinsonisms, dystonias, Tourette syndrome, periodic limb movement pathologies, restless legs syndrome, attention deficit hyperactivity disorders, Huntington's disease, progressive supranuclear palsy, Pick's disease, fronto-temporal dementia and neuromuscular diseases.

The compounds described in the present invention, their pharmaceutically acceptable salts and solvates, and the pharmaceutical compositions containing them may be used jointly with other, additional drugs, to provide combined therapy. Said additional drugs may be a part of the same pharmaceutical composition or, alternatively, may be provided in the form of a separate composition for simultaneous or non-simultaneous administration with the pharmaceutical composition comprising a compound with the formula (I) or the formula (II), or the cross-linked self-assembled star polymer a pharmaceutically acceptable salt, stereoisomer or solvate thereof.

The compounds with the formula (I), formula (II) or cross-linked self-assembled star polymer of formula (III) designed for therapeutic use are prepared in solid form or aqueous suspension, in a pharmaceutically acceptable diluent. These preparations may be administered by any appropriate administration route, for which reason said preparation will be formulated in the adequate pharmaceutical form for the selected administration route. In a particular embodiment, administration of the compound of formula (I) or (II), or cross-linked self-assembled star polymer with the formula (III) provided by this invention is performed by oral, topical, rectal or parenteral route (including subcutaneous, intraperitoneal, intradermal, intramuscular, intravenous route, etc.). A review of the different pharmaceutical forms for the administration of medicaments and the necessary excipients to obtain them may be found, for example, in "Tratado de Farmacia Galénica", C. Faulí i Trillo, 1993, Luzán 5, S. A. Ediciones, Madrid, or other habitual or similar ones in the Spanish Pharmacopeia and in the United States.

In an eight aspect, the present invention relates to a process for the synthesis of the compound of formula (I) of the first aspect of the invention or any embodiment thereto, the process comprising:

(1) reacting an amine or tetrafluoroborate or trifluoroacetate ammonium salt form of initiator of formula (IV) below

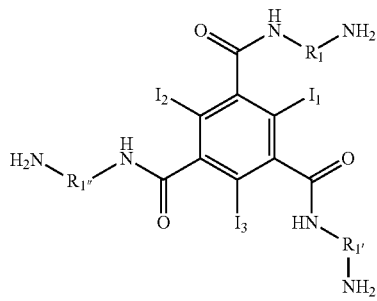

with an appropriate N-carboxyanhydride (NCA); alternatively, reacting the amine or tetrafluoroborate or trifluoroacetate ammonium salt form of initiator of step (1) with an appropriate N-carboxyanhydrides in a sequential manner to obtain a block co-polymer; alternatively, reacting the amine or tetrafluoroborate or trifluoroacetate ammonium salt form of initiator of step (1) with an appropriate NCA mixture in a statistical manner to obtain random co-polymers;

(2) optionally, reacting the amine group at the N-terminal position with an amine reactive group to introduce $R_5$, $R_{5'}$ and/or $R_{5''}$;

(3) optionally, orthogonally removing amino acid side chain protecting groups;

(4) purifying the product obtained in step (1), (2) or (3), optionally by fractionation, precipitation, ultrafiltration, dialysis, size-exclusion chromatography or tangential flow filtration.

Step (1) above may include: a) ring opening polymerization of amino acids N-carboxyanydride (NCA) monomer by reacting the amine or tetrafluoroborate or trifluoroacetate ammonium salt form of initiator of formula (IV) above with the selected NCA, wherein the ratio monomer/initiator allow to control the degree of polymerization (DP); b) a sequential polymerization, wherein block co-polypeptides are prepared following the polymerization reaction a) in a sequential manner, allowing the first NCA monomer to be consumed before adding the monomer to build the following polypeptidic block; or c) a statistical polymerization a) wherein random copolypeptides are prepared following the polymerization reaction a) in a statistical manner, mixing all the NCA monomers before starting the polymerization by the addition of an amine or tetrafluoroborate or trifluoroacetate ammonium salt form of initiator.

Step (2) above corresponds to the end-capping, wherein the amine group at the N-terminal position is reacted with an amine reactive group to introduce $R_5$, $R_{5'}$ or $R_{5''}$.

Step (3) above corresponds to the deprotection, wherein amino acid side chains are removed orthogonally depending on the protecting group present at Z.

The process for the synthesis of the compound of formula (II) of the second aspect of the invention or any embodiment thereto, the process further comprising:

(5) introducing the CL groups at reactive amino acid side chain, at the appropriate molar ratio;

(6) purifying the product obtained in step (5), optionally by fractionation, precipitation, ultrafiltration, dialysis, size exclusion chromatography or tangential flow filtration.

Step (5) above corresponds to the postpolymerization modification of amino acid side chain, wherein the required modification is introduced at the reactive amino acid side chain at the desired molar ratio to introduce CL groups.

The process for the synthesis of the cross-linked self-assembled star polymer of formula (III) of the third aspect of the invention or any embodiment thereto, the process further comprising:

(7) reacting the CL groups of the self-assembled compounds of formula (II) forming nanometric assemblies, to covalently cross-link the self-assembled star polymers;

(8) purifying the product obtained in step (7) optionally by fractionation, precipitation, ultrafiltration, dialysis, size exclusion chromatography or tangential flow filtration.

Step (7) above corresponds to the self-assembly and covalent cross-linking step, wherein compounds of formula (II) are self-assembled under the appropriate conditions depending on their nature to form nanometric assemblies. Then CL groups are reacted to covalently cross-link the self-assembled star polymers.

In another particular embodiment, the compound of formula (I) is a compound of formula (IA):

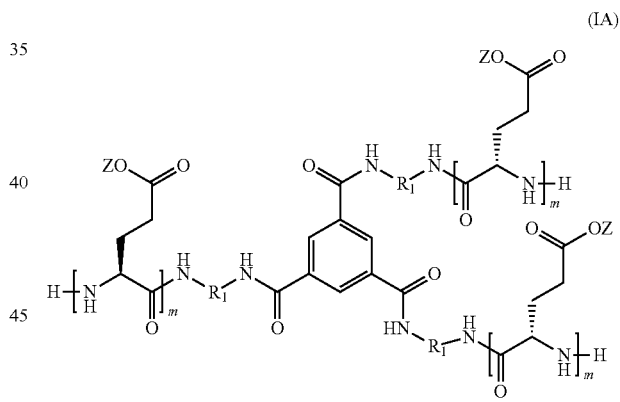

or its salts, solvates or isomers, wherein m is an integer selected from 1 to 500, Z is selected from H, lineal or chain alkyl $C_1$-$C_{10}$, aryl or SiRR' being R and R' alkyl $C_1$-$C_6$ or a metallic or organic cation, $R_1$ is selected from the following groups:

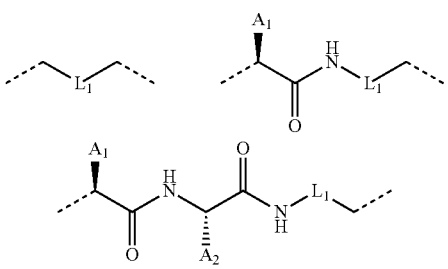

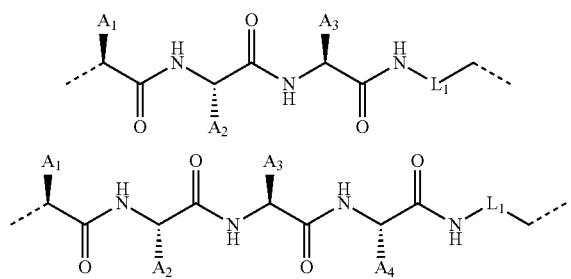

wherein $A_1$, $A_2$, $A_3$ and $A_4$ denotes the side residues of hydrophobic amino acids and they are selected from the following groups or combinations thereof:

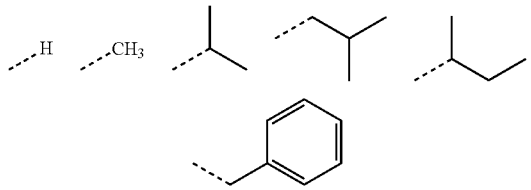

and $L_1$ represents a spacer selected from the following groups:

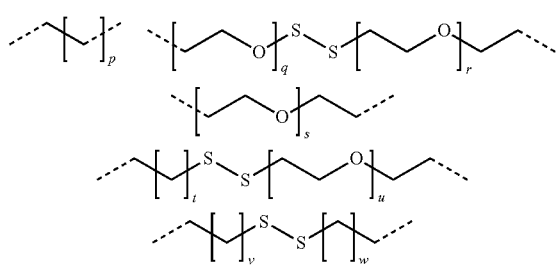

being p, q, r, s, t, u, v and w integers selected from 0 to 10 and 1 to 300 respectively, and ------- the bond which links these groups to the rest of the molecule.

In a preferred embodiment, $R_1$ of formula (IA) is selected from the following groups:

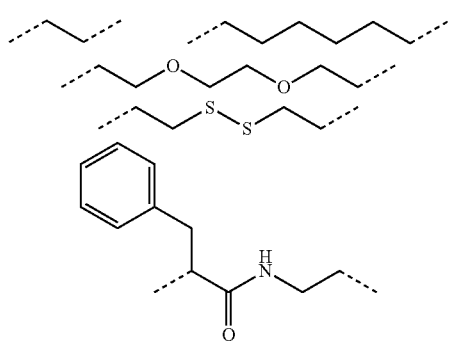

In another embodiment, the compound of formula (IA) is a compound of formula (IIA):

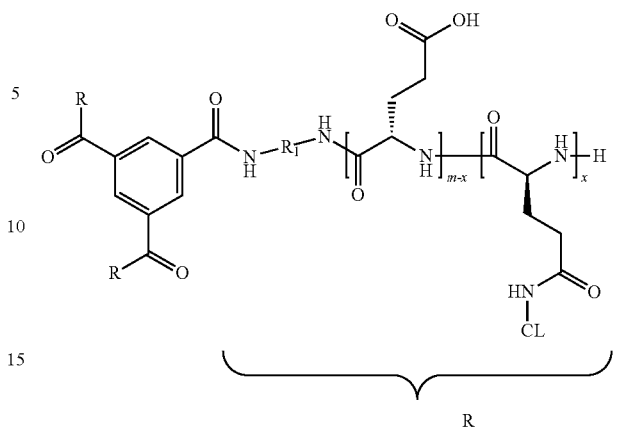

or its salts, solvates or isomers wherein m and $R_1$ are defined as in the particular embodiment of the invention corresponding to a compound of formula (IA) as defined for the first time above, x is and CL is selected from the following groups:

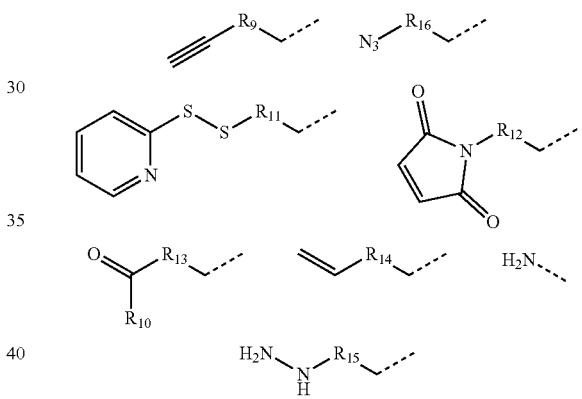

wherein $R_9$ to $R_{17}$ are selected from the following groups:

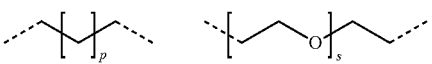

being p an integer selected from 0 to 10 and s an integer selected from 1 to 300 respectively, and $R_{10}$ is selected from a hydrogen or an alkyl $C_1$-$C_4$, and wherein the described substituent is also present in the positions marked with R.

In a preferred embodiment of the compound of formula (IIA), $R_1$ is selected from the following groups:

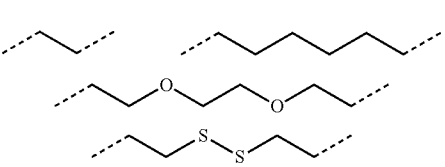

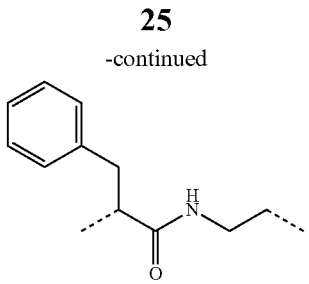

Another aspect of the invention is referred to a polymer comprising a recurring unit of formula (IIIA):

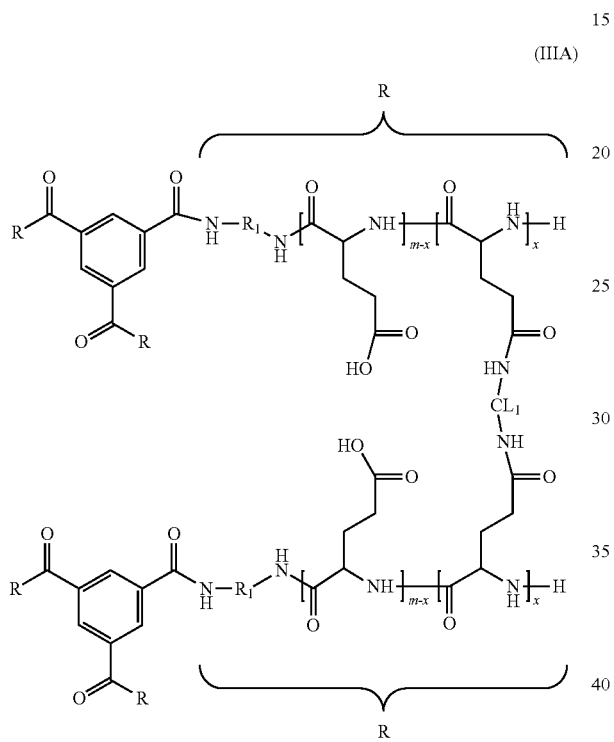

wherein $R_1$, m and x are defined as in the particular embodiment of the invention corresponding to a compound of formula (IA) as defined for the first time above and $CL_1$ is selected from the following groups:

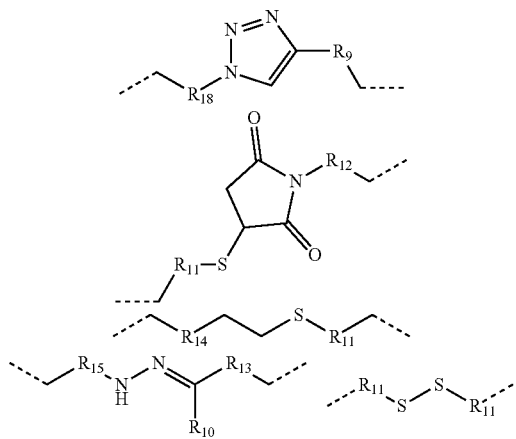

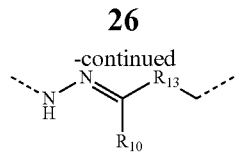

wherein $R_9$ to $R_{17}$ are defined as above.

In a preferred embodiment of the compound of formula (IIIA), $R_1$ is selected from the following groups:

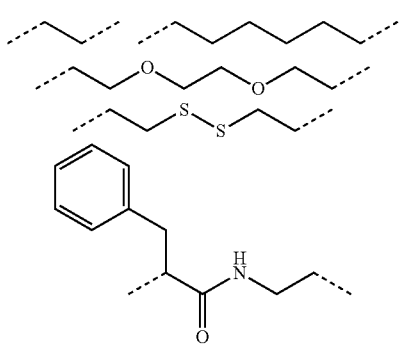

Another aspect of the invention, is a conjugate comprising the compound of formula (IIA) or the compound of formula (IIIA) and at least an agent which is covalently linked to the compound through the COOH surface groups of the compound of formula (IIIA) or through a spacer, preferably the agent is selected from the group consisting of a drug, a targeting agent, an optical imaging agent, a magnetic resonance imaging agent and a stabilizing agent, more preferably the conjugate of previous claim wherein the agent is a drug selected from selegiline, rasagiline, ladostigilM30, curcumin, demethoxycurcumin, bisdemethoxycurcumin.

Preferably, in the conjugate described above the conjugate comprises an amount of the agent in the range of 1% to 50% (weight/weight) based on the mass ratio of the agent to the conjugate.

Another aspect refers to a pharmaceutical composition comprising at least one conjugate as described above and at least a pharmaceutical excipient.

Another aspect refers to the conjugate described above for use as a medicament.

Another aspect refers to the conjugate as described above for use in the prevention or treatment of a neurodegenerative or neurological disease or cancer.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings are provided by way of illustration and are not intended to be limiting of the present invention.

EXAMPLES

Figure 1:
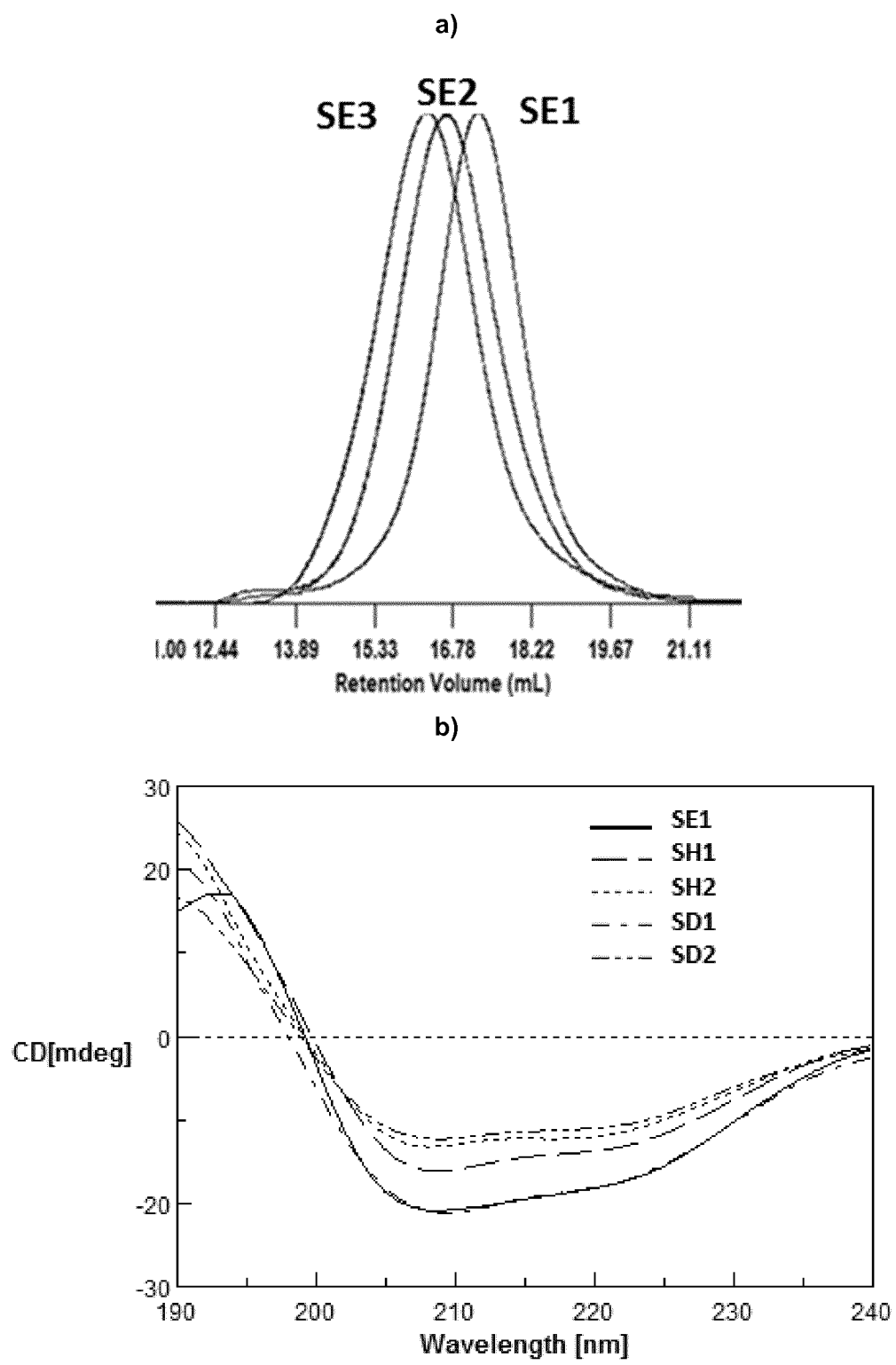
FIG. 1. a) Selected GPCs from St-Poly-(gamma-benzyl-L-glutamate) (PBLG) (compounds of formula (I)) of different molecular weights in DMF (1% LiBr) at 8 mg·mL$^{-1}$. b) CD of St-PBLG (compounds of formula (I)) at 20° C. in HFIP at 0.1 mg·mL$^{-1}$.

Example 1: Synthesis of Compounds of Formula (I)

To synthesize compounds of formula I, first, the 3-arm star initiator was obtained in 2-4 steps. Such initiator was used to polymerize gamma-benzyl L-glutamate N-carboxyanhydride monomer, to yield the star polymer benzyl protected (St-PBLG). The benzyl groups were removed to yield St-PGA.

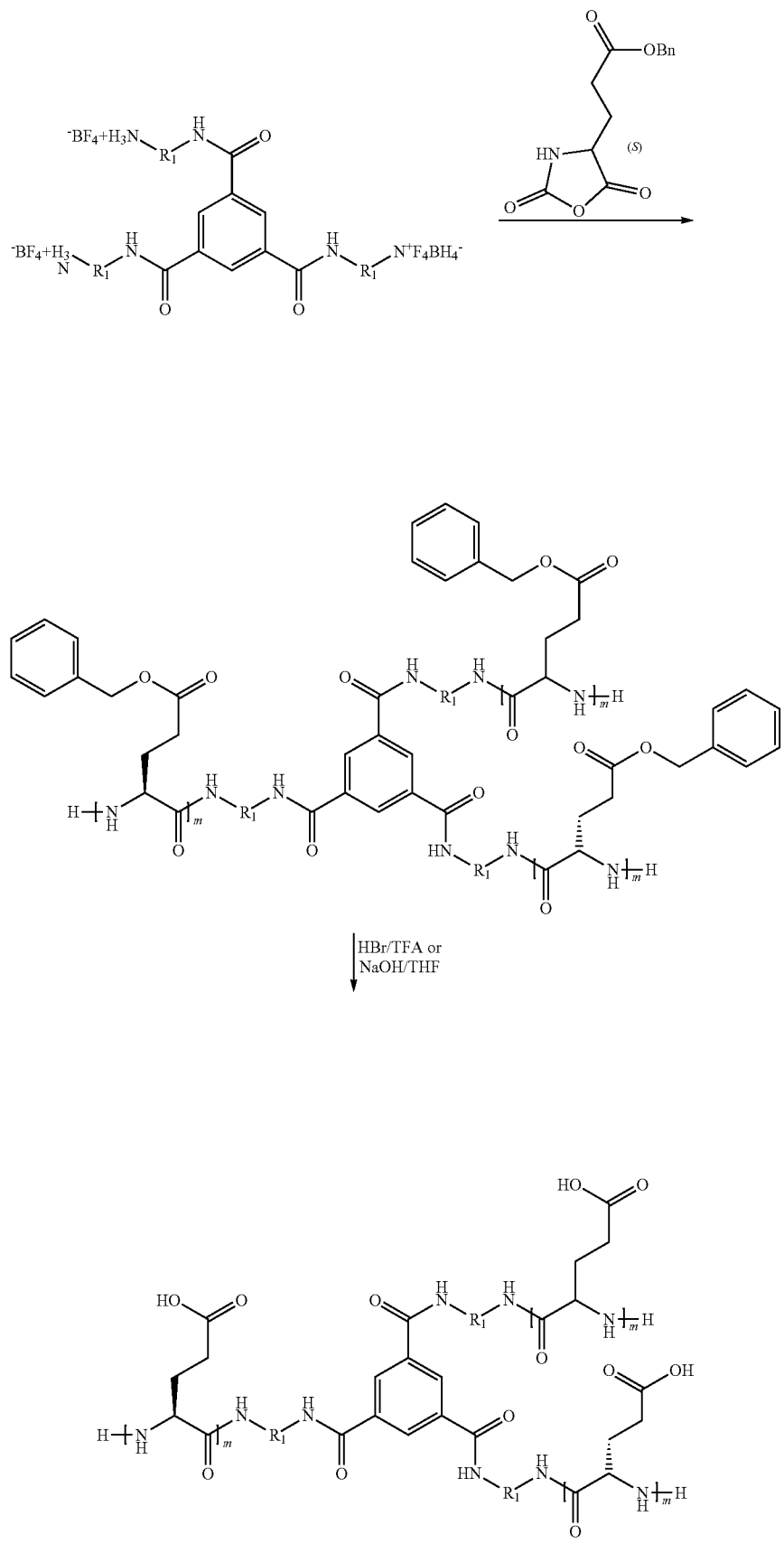

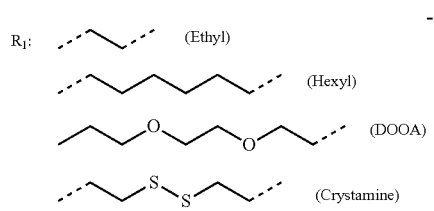

-continued

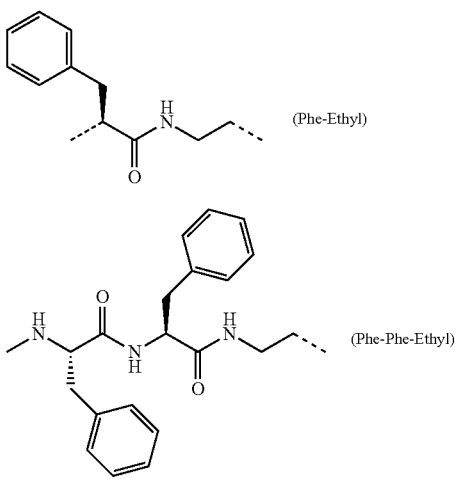

1.1. Example of Synthesis of 3-Arm Star Initiators a) Synthesis of 1,3,5-tri-tert-butyl ((benzenetricarbonyltris(azanediyl)) tris(ethane-2,1-diyl))tricarbamate

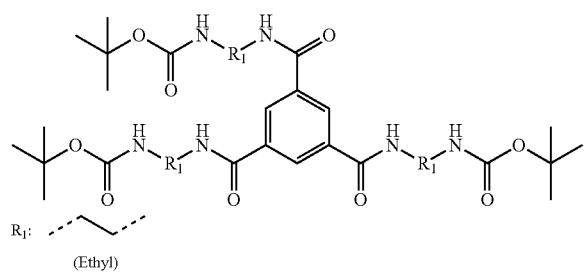

In a two-neck round bottom flask fitted with a stirrer bar, and a $N_2$ inlet and outlet, 500 mg of 1,3,5-benzenetricarbonyl trichloride (1.88 mmol, 1 equivalent (eq.)) was dissolved in 12 mL of anhydrous THF. N,N',N''-diisopropylethylendiamine (DIEA) (803.31 mg, 6.22 mmol, 3.3 eq.) was added to the reaction mixture followed by drop-wise addition of N-tert-Butoxycarbonyl-ethylendiamine (N-Boc-ethylenediamine) (1.34 g, 6.22 mmol, 3.3 eq.) over a period of 10 min. The reaction was then left to proceed for 2 hours. After that time, the solvent was completely removed under vacuum. The product was re-dissolved in chloroform and washed 3 times with deionized water ($ddH_2O$), and 3 times with acidic water (pH-3). Finally, the organic phase was isolated under vacuum and the product was recrystallized 3 times from THF/Methanol/Hexane yielding a white crystalline solid. The product was then dried under high vacuum and stored at −20° C.

Yield: 82%. $^1$H NMR (300 MHz, DMSO) δ 8.68-8.65 (m, 3H), 8.41 (s, 3H), 6.92-6.88 (m, 3H), 3.34-3.31 (m, 6H), 3.16-3.13 (m, 6H), 1.37 (s, 27H). $^{13}$C NMR (75 MHz, $CDCl_3$) δ 166.80 (C=O), 156.84 (C=O), 134.58 ($C_{Ar}$ quaternary), 128.47 ($C_{Ar}$), 79.57 (C quaternary), 40.93 ($CH_2$), 40.43 ($CH_2$), 28.45 ($CH_3$).

b) Synthesis of 1,3,5-(benzenetricarbonyltris(azanediyl))triethanamonium $BF_4$ Salt

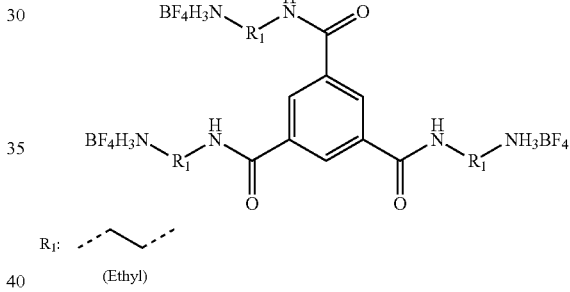

In a round bottom flask fitted with a stirrer bar and a stopper, 200 mg of 1,3,5-Tri-tert-butyl ((benzenetricarbonyltris(azanediyl)) tris(ethane-2,1-diyl))tricarbamate (0.33 mmol, 1 eq.) was dissolved in dichloromethane. Afterwards, 3.3 eq. of tetrafluoroboric acid diethyl ether complex, $HBF_4 \cdot Et_2O$, (179 mg, 150 µL), was added to the solution leading to the instantaneous formation of a white solid. The precipitate was filtered off and recrystallized three times from THF/methanol/hexane. The product was then dried under high vacuum and stored at −20° C.

Yield: 98%. $^1$H NMR (300 MHz, $D_2O$) δ 8.32 (s, 3H), 3.72-3.68 (m, 6H) 3.25-3.21 (m, 6H). $^{13}$C NMR (75 MHz, $D_2O$) δ 169.45 (C=O), 134.38 ($C_{Ar}$ quaternary), 129.36 ($C_{Ar}$), 39.23 ($CH_2$), 37.52 ($CH_2$). 19F-NMR: −150.48 ($BF_4$). MALDI-TOF: 337.1709 [$M^{+1}$]

Initiators used for the preparation of polypeptides in table 1 are synthesized following analogous procedures as the ones described above. For L-phenylalanine containing initiators the synthetic route and their $^1$H NMR signals are summarized below. For clarity only one of the three substituents at the 1,3,5-benzenetricarboxamide motif is shown:

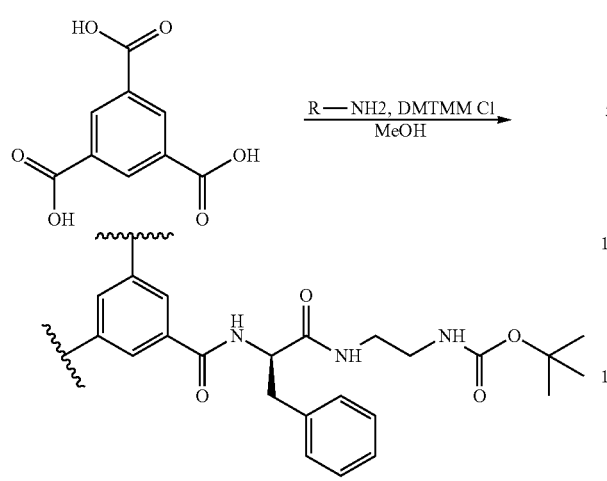

Procedure: 1,3,5-benzenetricarboxylic acid (1 eq.) was dissolved in methanol and DMTMM chloride was added (3.9 eq.). After 10 minutes solution of N-Boc-N'-(L-phenylalaninyl) ehhylenediamine (3.9 eq.) in methanol was added. Reaction allowed to proceed for 48 h. Product was precipitated in water, filtered and washed with water. The product was freeze-dried.

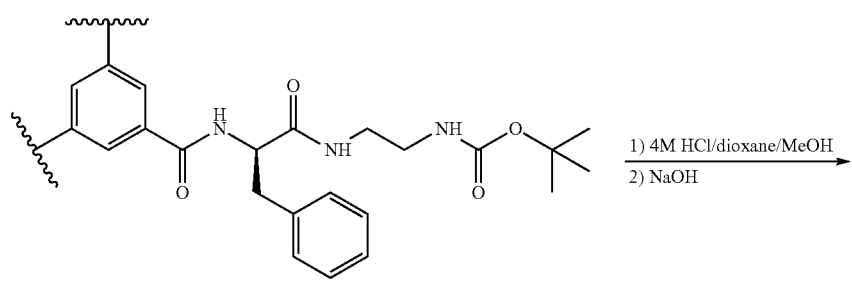

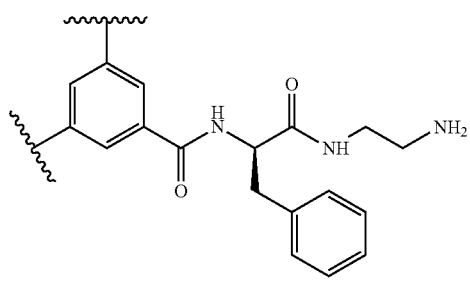

Procedure: In a round-bottom flask fitted with a stirrer compound (1 eq.) was suspended in 1 ml of methanol. 4M HCl solution in dioxane was added (9 eq.). Reaction allowed to proceed for 2 hours. Mixture was precipitated in diethyl ether, washed and redissolved and treated with NaOH (till pH 10). Precipitate was filtered, washed with water and freeze-dried.

1H-NMR (DMSO-d6): 2.54 (dt, 1H), 2.94-3.14 (m, 7H), 4.72 (dt, 1H), 7.12-7.35 (m, 5H), 8.07 (t, 1H), 8.23 (s, 1H), 8.75 (d, 1H).

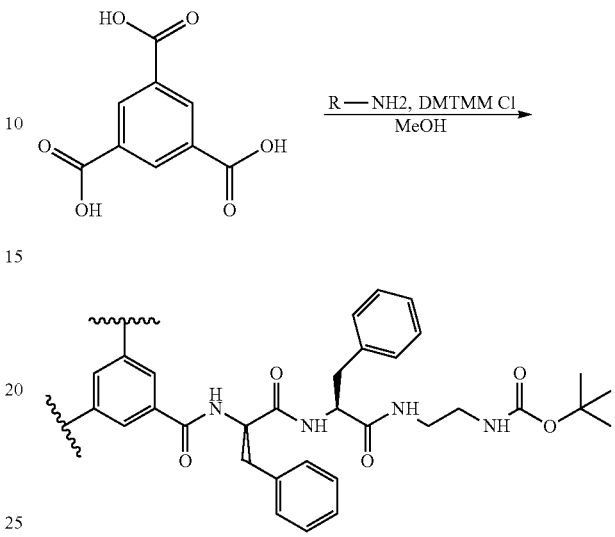

Procedure: 1,3,5-benzenetricarboxylic acid (1 eq.) was dissolved in methanol and DMTMM chloride was added (3.9 eq.). After 10 minutes solution of N-Boc-N'-(L-phenylaninephenylaninyl) ehhylenediamine (3.9 eq.) in methanol was added. Reaction allowed to proceed for 48 h. was precipitated in water, filtered and washed with water. The product was freeze-dried.

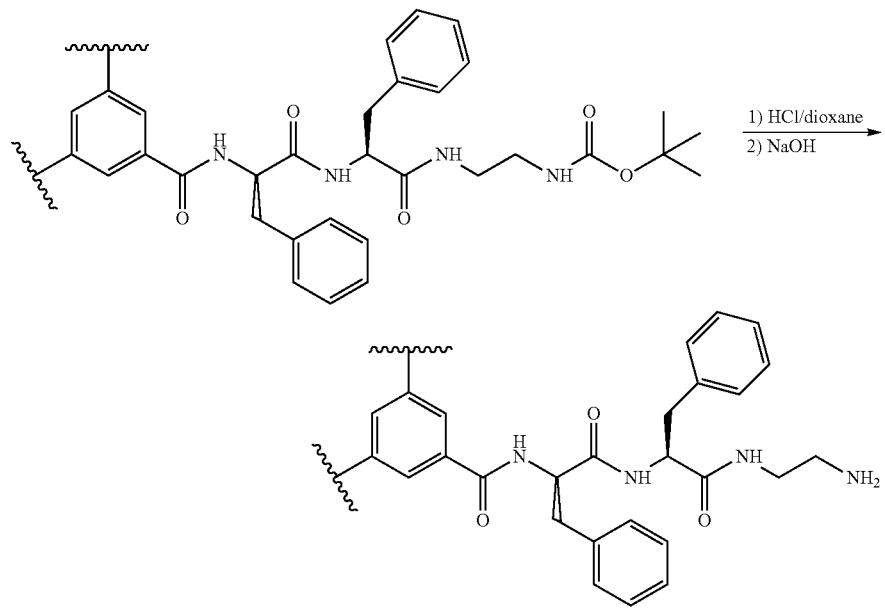

Procedure: In a round-bottom flask fitted with a stirrer compound (1 eq.) was suspended in 1 ml of methanol. 4M HCl solution in dioxane was added (9 eq.). Reaction allowed to proceed for 2 hours. Mixture was precipitated in diethyl ether, washed and redissolved and treated with NaOH (till pH 10). Precipitate was filtered, washed with water and freeze-dried.

1H NMR (DMSO-d6): 2.47 (dd, 1H), 2.8-3.1 (m, 7H), 4.49 (dt, 1H), 4.74 (ddd, 1H), 7.08-7.31 (m, 10H), 7.81 (t, 1H), 8.2 (t, 1H), 8.23 (s, 1H), 8.77 (d, 1H).

1.2. St-PBLG Polymer Synthesis

Briefly, γ-Benzyl L-glutamate N-carboxyanhydrides (0.5 g, 1.9 mmol) was added to a Schlenk tube fitted with a stirrer bar, a stopper and purged with 3 cycles of vacuum/Ar, and dissolved in 5 mL of the freshly purified solvent. The 3-arm initiator was added and the mixture was left stirring at 4° C. for 3 days under inert atmosphere. Finally, the reaction mixture was poured into a large excess of cold diethyl ether leading to a white polymer after isolation.

Yield: 70-90%. $^1$H-NMR (300 MHz, DMF, δ) 8.58 (s, xH), 7.42 (s, 5H), 5.19 (s, 2H), 4.21 (s, 1H), 2.81 (s, 2H), 2.45 (s, 2H). $^{13}$C-NMR (300 MHz, DMF, δ) 175.94 (s), 172.26 (s), 162.77-162.18 (m), 161.98 (s), 136.76 (s), 128.87-127.75 (m), 66.05 (s), 57.13 (s), 35.41-34.17 (m), 32.48 (s), 30.84, 30.30-29.04 (m), 27.28 (s), 25.99 (s). x: DP obtained/3 arms.

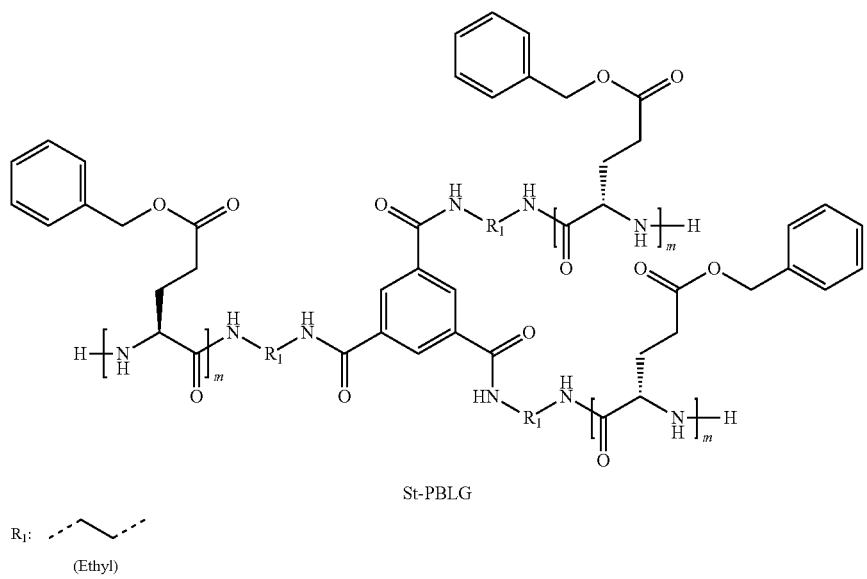

TABLE 1

Variety of initiators used in the polymerization processes and different DPs obtained for St-PBLGs, demonstrating the versatility of the technique.

| Star | $R_1$ | $DP_{theo}$ | $Mn^a$ (kDa) | $Mn^b$ (kDa) | $DP^a$ | $DP^b$ | Ð |
|---|---|---|---|---|---|---|---|
| SE1 | Ethyl | 100 | 21.3 | 21.0 | 97 | 96 | 1.26 |
| SE2 | 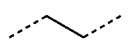 | 150 | 24.0 | 27.6 | 110 | 126 | 1.22 |
| SE3 |  | 250 | 50.3 | 51.5 | 229 | 235 | 1.09 |
| SH1 | Hexyl | 75 | 16.4 | n.d. | 75 | n.d. | 1.25 |
| SH2 | 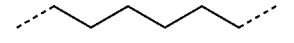 | 150 | 23.9 | 23.6 | 109 | 108 | 1.23 |
| SH3 |  | 250 | 51.5 | 52.7 | 235 | 240 | 1.17 |
| SD1 |  | 75 | 15.7 | 16.9 | 72 | 77 | 1.13 |
| SD2 | DOOA | 100 | 22.2 | 24.1 | 101 | 110 | 1.23 |
| SD3 | 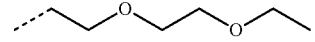 | 150 | 33.2 | 31.1 | 152 | 142 | 1.10 |
| SD4 |  | 200 | 40.4 | 41.6 | 185 | 190 | 1.12 |
| SS1 | Cysteamine 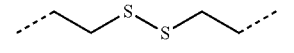 | 200 | 43.1 | n.d. | 196 | n.d. | 1.22 |
| SP1 | Phe-Ethyl 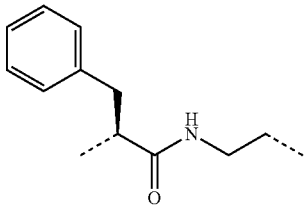 | 400 | 79.8 | 79.8 | 375 | 375 | 1.12 |
| SPP1 | Phe-Phe-Ethyl 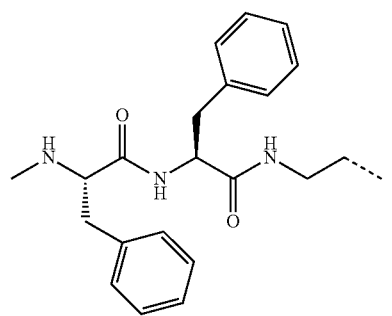 | 150 | 31.5 | 28.9 | 144 | 132 | 1.06 |

[a] Determined by NMR.
[b] Determined by GPC.
Mn and DP refer to number average molar mass and degree of polymerization respectively.
n.d. = not determined.

FIG. 1 shows routine characterization by GPC and CD of compounds of formula (I).

Following the general procedure for the polymerization described in section 1.2 for St-PBLG, and using the ethyl based initiator, a series of homopolypeptides and block or random copolypeptides have been synthesized using the respective amino acid N-carboxyanhydride; epsilon-trifluoroacetate-L-Lysine N-carboxyanhydride, Benzyl-L-Serine N-carboxyanhydride, Sarcosine NCA. For random copolymers NCAs were mixed in the reaction environment prior to the addition of the initiator. For block copolymer, gamma-Benzyl L-glutamate N-carboxyanhydride was first polymerized through the addition of initiator followed by the addition of the second monomer once the first monomer was consumed.

TABLE 2

Variety of star-shaped polymers (compounds of formula (I)) synthesized with other NCA monomers.

| Star | R₁ | $DP_{theo}$ | $Mn^a$ (kDa) | $Mn^b$ (kDa) | $DP^a$ | $DP^b$ | Ð |
|---|---|---|---|---|---|---|---|
| St-PTLL | | 60 | 13.2 | 10.7 | 59 | 48 | 1.13 |
| St-PTLL | | 25 | 5.0 | 3.6 | 22 | 16 | 1.03 |
| St-PBLS |  | 60 | n.d. | 9.7 | n.d. | 55 | n.d. |
| | | 25 | 4.0 | 3.4 | 23 | 20 | 1.10 |
| St-PSAR | | 60 | 5.0 | 4.3 | 70 | 61 | 1.18 |

*St-PTLL: Star-Poly(epsilon-trifluoroacetate-L-Lysine), St-PBLS: Star-Poly(Benzyl-L-Serine), St-PSAR: St-Poly(Sarcosine)
aObtained by GPC measurement in DMF/LiBr (0.1%).
bObtained by 1H-NMR in deuterated TFA.
n.d.: not determined.

TABLE 3

Star-shaped polymers (compounds of formula (I)) copolymers with BLG and SAR.

| Star | R₁ | $DP_t$ BLG | $DP_t$ SAR | $Mn^a$ (kDa) | $Mn^b$ (kDa) | $DP^b$ BLG | $DP^b$ SAR | Ð |
|---|---|---|---|---|---|---|---|---|
| St-P(BLG-co-LSAR) | Ethyl | 30 | 30 | 7.9 | 6.4 | 23 | 20 | 1.06 |
| St-P(BLG-b-LSAR) | | 30 | 30 | 8.5 | 6.6 | 24 | 20 | 1.05 |

*St-P(BLG-co-SAR): St-poly(gamma-benzyl-L-glutamate-co-sarcosine) random copolymer, St-P(BLG-b-SAR): St-poly(gamma-benzyl-L-glutamate-block-L-sarcosine) block copolymer.
aObtained by GPC measurement in DMF/LiBr (0.1%).
bObtained by ¹H-NMR in deuterated TFA.

Figure 2:
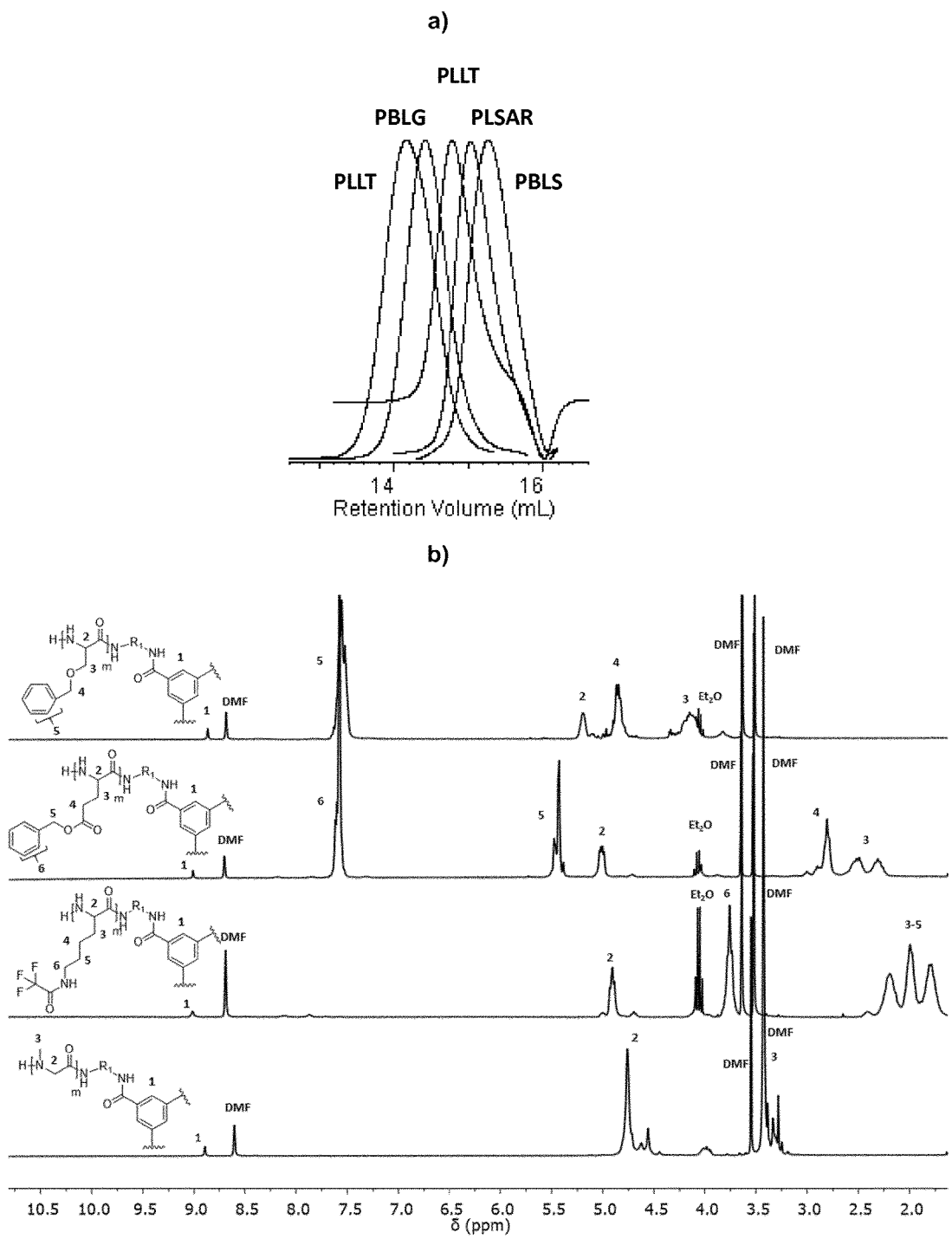
FIG. 2. a) Selected GPCs in DMF (1% LiBr) at 8 mg·mL$^{-1}$ and b) Selected $^1$H-NMR and respective signal assignment in deuterated TFA of St-PTLL: Star-Poly(epsilon-trifluoroacetate-L-Lysine), St-PBLS: Star-Poly(Benzyl-L-Serine), St-PSAR: St-Poly(Sarcosine), St-PBLG: St-Poly(gamma-benzyl-L-glutamate) (compounds of formula (I)). * R$_1$ is an ethyl.
Figure 3:
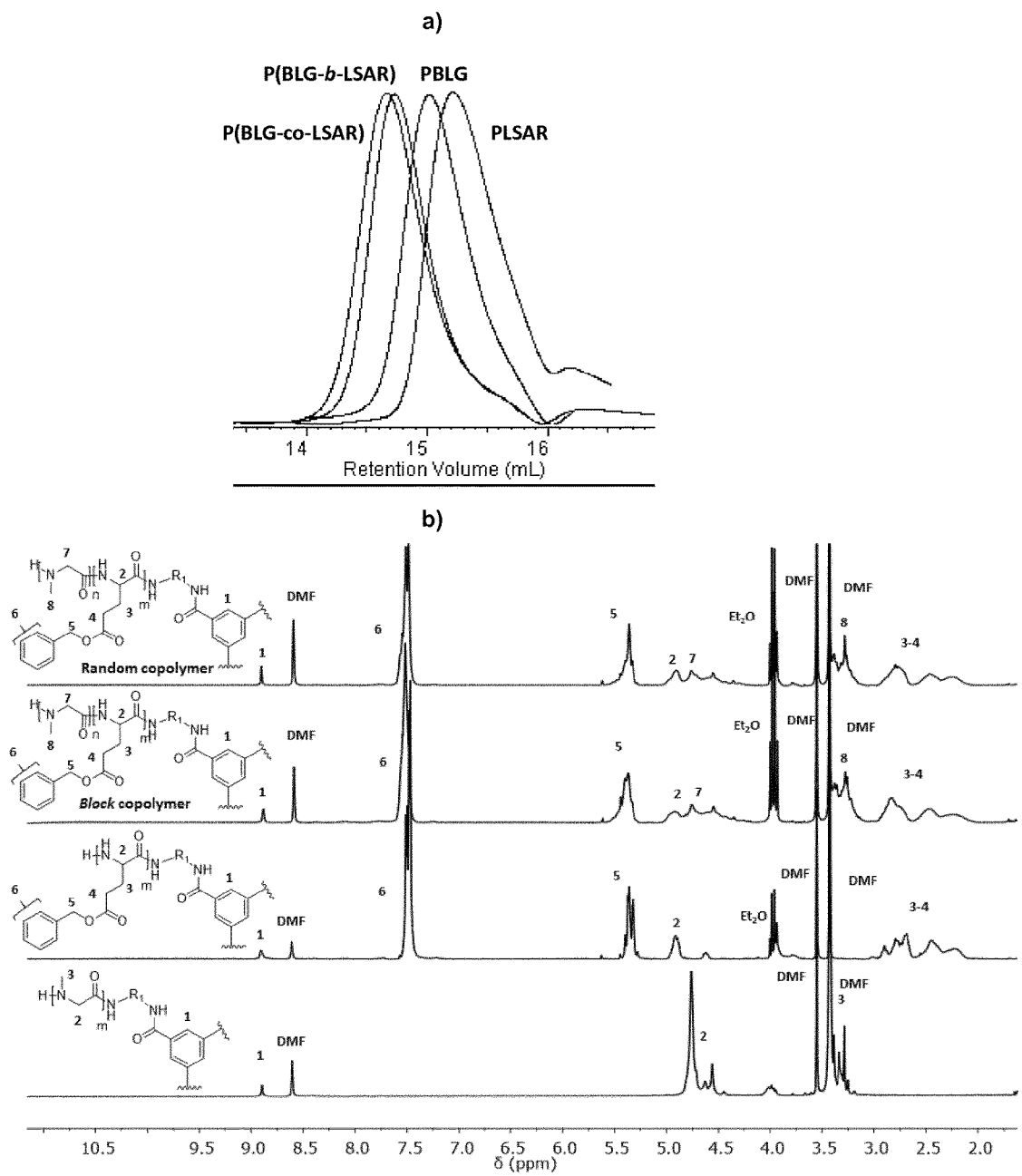
FIG. 3. a) Selected GPCs in DMF (1% LiBr) at 8 mg·mL$^{-1}$ and b) Selected $^1$H-NMR and respective signal assignment in deuterated TFA of St-PSAR: St-Poly(Sarcosine), St-PBLG: St-Poly-(gamma-benzyl-L-glutamate), St-P(BLG-co-SAR): St-poly(gamma-benzyl-L-glutamate-co-sarcosine) random copolymer, St-P(BLG-b-SAR): St-poly(gamma-benzyl-L-glutamate-block-sarcosine) block copolymer (compounds of formula (I)). * R$_1$ is an ethyl.

FIGS. 2 and 3 show routine characterization by GPC of compounds of formula (I).

1.3. Deprotection of St-PBLG:

Different methods were followed depending on the initiator used: acid conditions were applied when ethyl and hexyl based initiators were used (initiators including ethyl or hexyl spacers). On the other hand, basic conditions were applied for DOOA (3,6-dioxa-8-octaneamine), and cysteamine based initiators synthesis (inititiators including DOOA or cysteamine spacers). Briefly:

a) Deprotection of St-PBLG with HBr in Trifluoroacetic Acid (TFA): in a round bottom flask fitted with a glass stopper and a stirrer bar, 50 mg of St-PBLG (0.23 mmol, 1 eq. Glutamic Acid Unit, GAU) were dissolved in trifluoroacetic acid (TFA). Once dissolved, 2 eq. of HBr (48% v/v) per carboxyl group were added drop wise, and the mixture was stirred for five hours. For big scale deprotection of St-PBLG, 16 hours were applied for full deprotection. Then, the solution was poured into a large excess of cold diethyl ether leading to a white solid after isolation.

b) Deprotection of St-PBLG in basic conditions: in a round bottom flask, 40 mg of benzyl protected St-PBLG (0.183 mmol, 1 eq. GAU) was dissolved in 16 mL of THF. The solution was cooled down to 4° C. and 2 eq. of NaOH per carboxylic group of the polypeptide block (14.7 mg, 0.369 mmol) were added in 2 mL of ddH₂O. The mixture was stirred for 16 hours. Finally, THF was removed and the residue was diluted with ddH₂O, concentrated and purified by ultrafiltration (Vivaspin®, Molecular Weight Cut-off MWCO=3000 Da) or by size exclusion columns (G25).

Yields: 75-86%. ¹H-NMR (300 MHz, D₂O, δ) 8.2 (s, xH), 4.31-4.26 (m, 1H), 2.38-2.14 (m, 2H) 2.10-1.80 (m, 2H) 2.10-1.80 (m, 2H). x: DP obtained/3 arms. Depending on the initiator used, the corresponding signals of the ethyl, hexyl, or DOOA were also present.

The deprotection of St-PBLG leads to the compound of formula (I) denominated St-PGA:

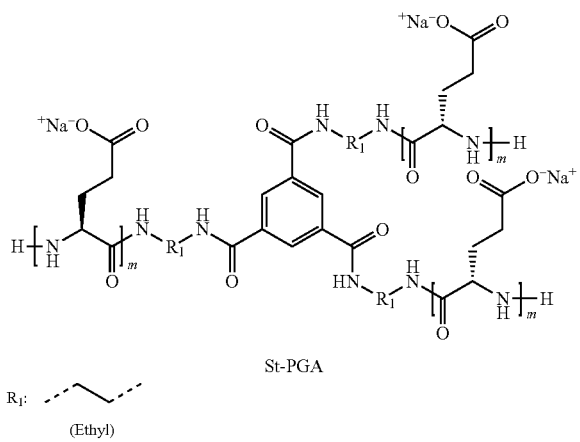

St-PGA

R₁: (Ethyl)

Figure 4:
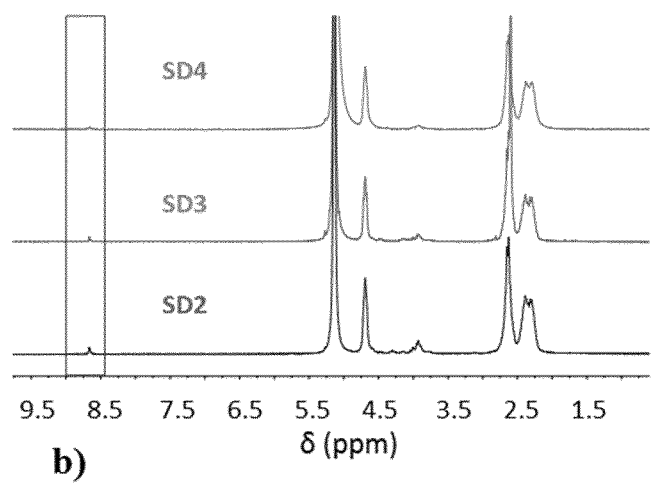
FIG. 4. a) $^1$H-NMR of St-PGAs (compounds formula (I)) of different molecular weights in D$_2$O. The small square is surrounding the benzyl core signals. b) CD of St-PGAs (compounds formula (I)) in PBS at 37° C. at 1 mg/mL showing typical random coil conformation of PGA chains.
Figure 4:
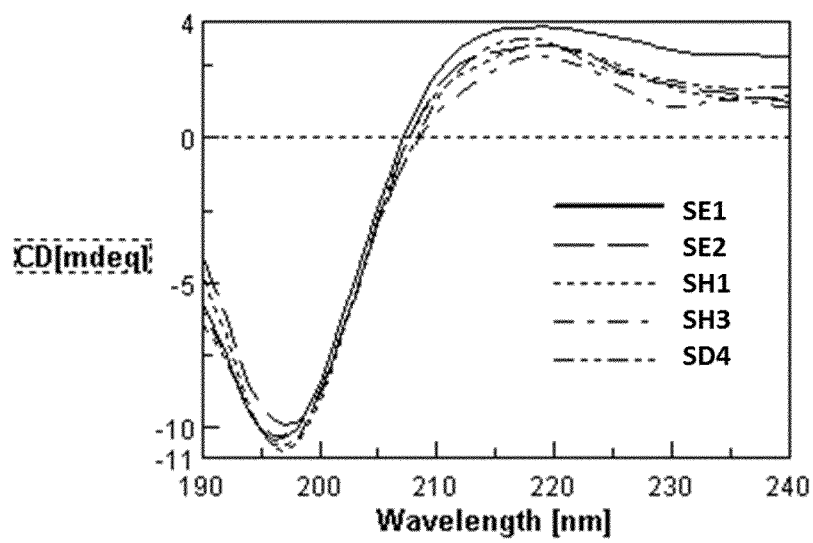

FIG. 4 shows routine characterization by ¹H-NMR and circular dichroism of compounds of formula (I)

Figure 5:
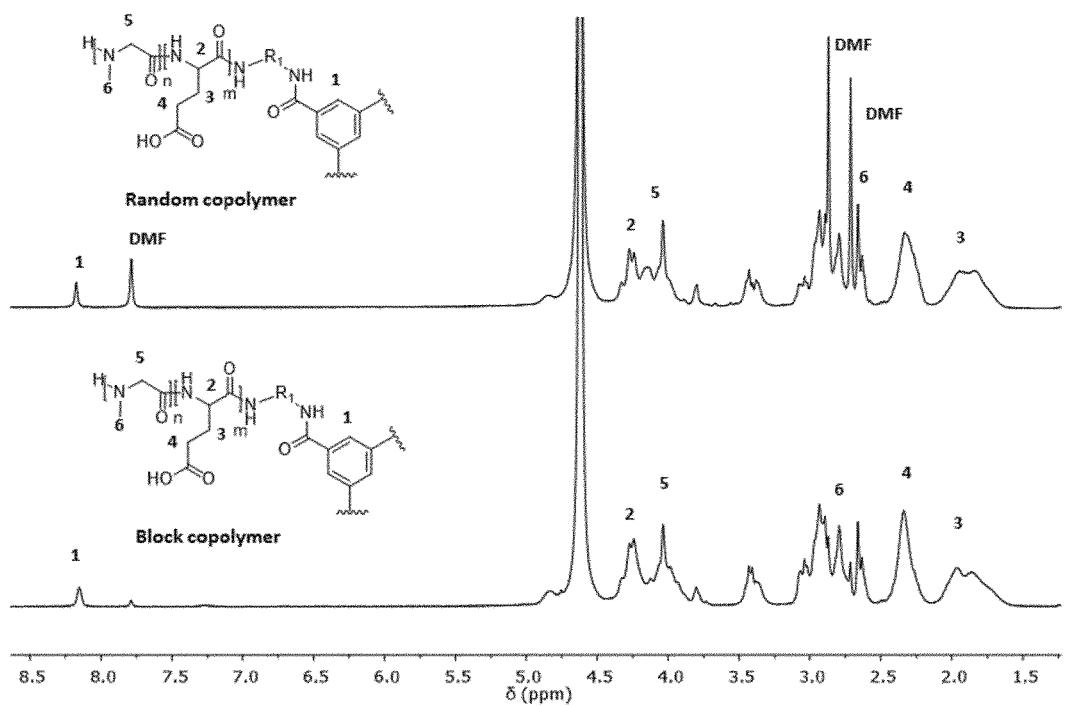
FIG. 5. a) $^1$H-NMR of (compounds formula (I)), St-P(BLG-co-SAR): St-poly(gamma-benzyl-L-glutamate-co-sarcosine) random copolymer, St-P(BLG-b-SAR): St-poly(gamma-benzyl-L-glutamate-block-sarcosine) block copolymer in D$_2$O. * R$_1$ is an ethyl.

Following the deprotection method a, the polypeptides synthesized in table 3 were deprotected and FIG. 5 shows the respective ¹H NMR in D₂O.

Example 2. Synthesis of Compounds of Formula (II)

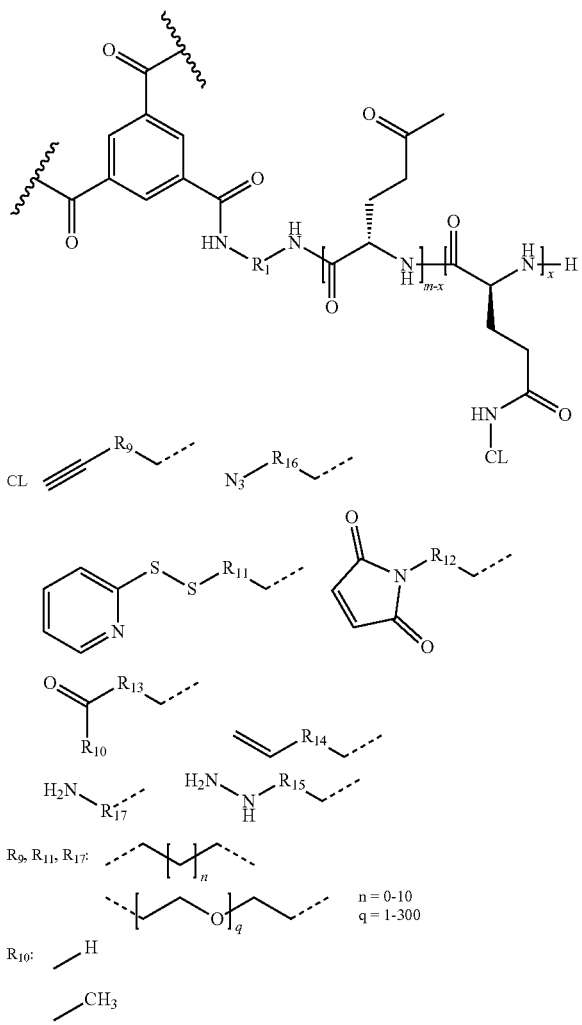

In a one neck round bottom flask fitted with a stir bar and a stopper, 200 mg of St-PGA (1.55 mol GAU, 1 eq.) were suspended in 10 mL of ddH$_2$O. Afterwards the eq. for the desired modification of 4-(4,6-Dimethoxy-1,3,5-triazin-2-yl)-4-methyl morpholinium (DMTMM) chloride (DMTMM-Cl) were added dissolved in 5 mL of ddH$_2$O (i.e. 128.7 mg, 0.465 mmol, 0.3 eq. for 30% modification). After 10 minutes (0.93 mmol 0.6 eq. for 30% modification) of the corresponding amine were added and the pH was adjusted to 8 by adding some drops of 1 M NaHCO$_3$ solution. Reaction was allowed to proceed overnight stirring at r.t. After this, as all by products were soluble in acid aqueous solution, either acid/base precipitation, dialysis (Vivaspin® MWCO 3000 Da), or size exclusion chromatography with Sephadex G25 columns, was done in order to purify the copolymer. A colorless amorphous solid was obtained after freeze-drying.

Yields: 80-90%. $^1$H-NMR $\delta_H$ (300 MHz, D$_2$O) and chemical structures:

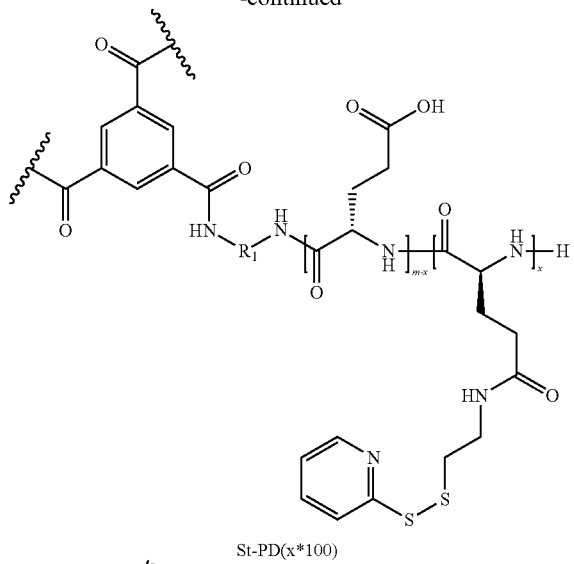

St-PD(x*100)

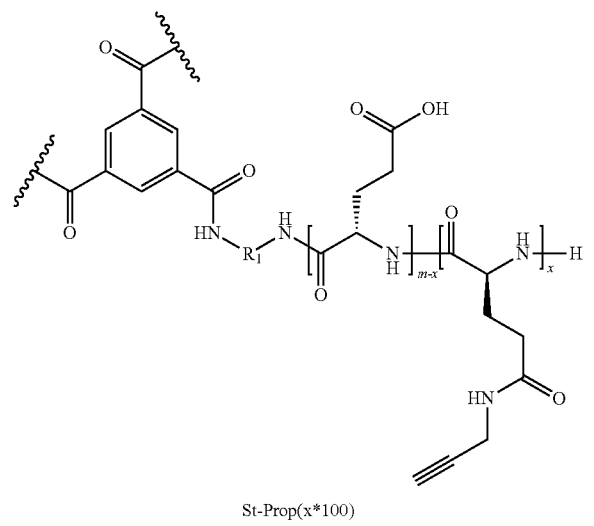

St-Prop(x*100)

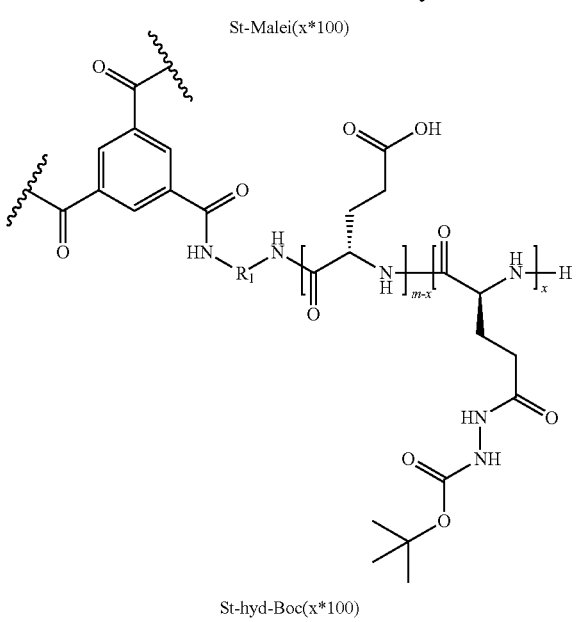

St-Malei(x*100)

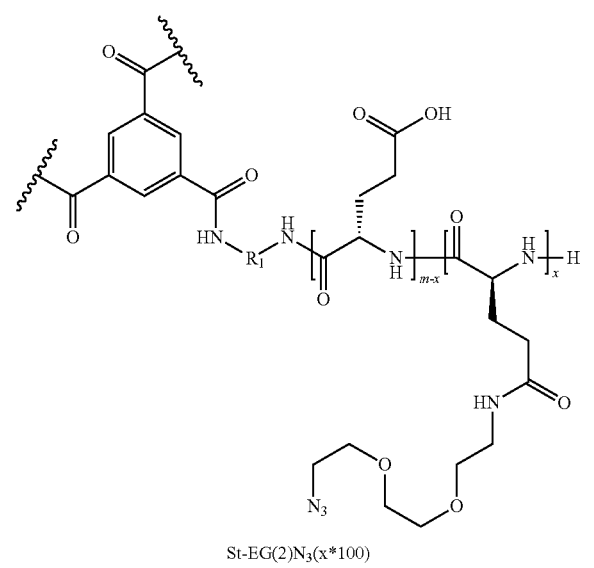

St-EG(2)N$_3$(x*100)

St-hyd-Boc(x*100)

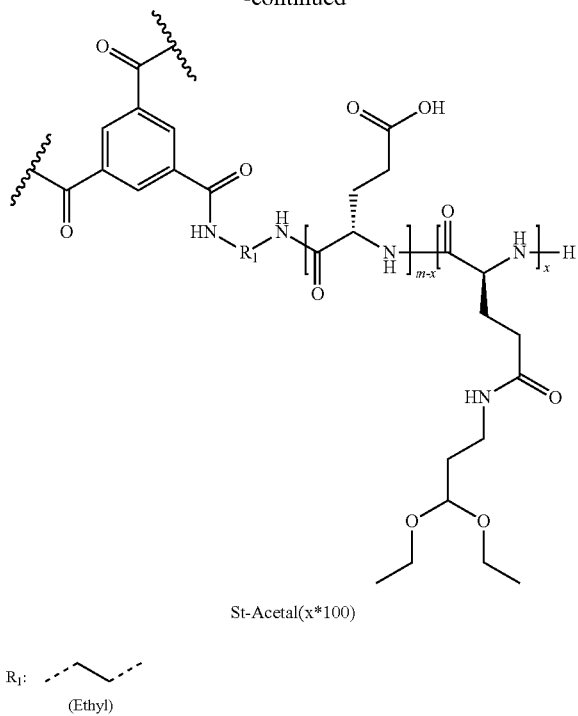

St-Acetal(x*100)

$R_1$: (Ethyl)

a) Star Poly(glutamic acid-co-propargyl glutamate), St-Prop (x): ¹H-NMR $\delta_H$ (300 MHz, D₂O): 8.2 (1H/(3DP),s), 4.30-4.02 (1H, m), 3.81 (2×H, s), 2.48 (1×H, s), 2.35-2.02 (2H, m), 2.01-1.65 (2H, m). x: molar percentage of modification.

b) Star Poly(glutamic acid-co-EG(n)N₃ glutamate), St-EG (2)N₃(x): ¹H-NMR $\delta_H$ (300 MHz, D₂O): 8.2 (1H/(3DP), 4.28-4.07 (1H, m), 3.65-3.51 (xH, m), 3.48 (2×H, t), 3.40-3.30 (2×H, m), 3.25 (2×H, d), 2.29-2.00 (2H, m), 1.98-1.65 (2H, m). *R: 8 for EG2, 20 for EG6, 32 for EG9. x: molar percentage of modification.

c) Star Poly(glutamic acid-co-pyridyl cysteamine), St-PD (x): ¹H-NMR $\delta_H$ (300 MHz, D₂O): 8.4 (xH+1H/(3DP), m), 7.84 (2×H, m), 7.28 (xH, m), 4.33 (1H, m), 3.48 (2×H, m), 2.95 (2×H, m), 2.3-1.9 (4H, m). x: molar percentage of modification. d) St-Poly(glutamic acid-co-amino-ethyl-maleimide glutamate), St-Malei(X): ¹H-NMR $\delta_H$ (300 MHz D₂O): 8.32 (1H/(3DP), s), 6.91 (2×H, s), 4.39 (1H, s), 3.80-3.16 (4×H, m), 2.18 (4H, m). x: molar percentage of modification.

e) St-Poly(glutamic acid-co-hydrazide-boc glutamate), St-hyd-boc(x): ¹H-NMR $\delta_H$ (300 MHz, D₂O): 8.34-8.25 (1H/(3DP), s), 4.33 (1H, s), 2.53-1.75 (4H, m), 1.45 (×1H, s). x: molar percentage of modification.

f) St-Poly(glutamic acid-co-acetaldehyde) St-acetal(x): ¹H-NMR $\delta_H$(300 MHz, D₂O): 8.29 (1H/(3DP), s), 4.32 (1H, s), 3.87-3.45 (×4H, m), 3.18 (×1H, m), 3.02 (×1H, m), 2.45-1.85 (4H, m), 1.77-1.47 (×4H, m), 1.19 (×6H, m). x: molar percentage of modification.

The synthesis were also carried out in organic solvents such as DMF, using the BF₄ salt of the DMTMM derivative.

Figure 6:
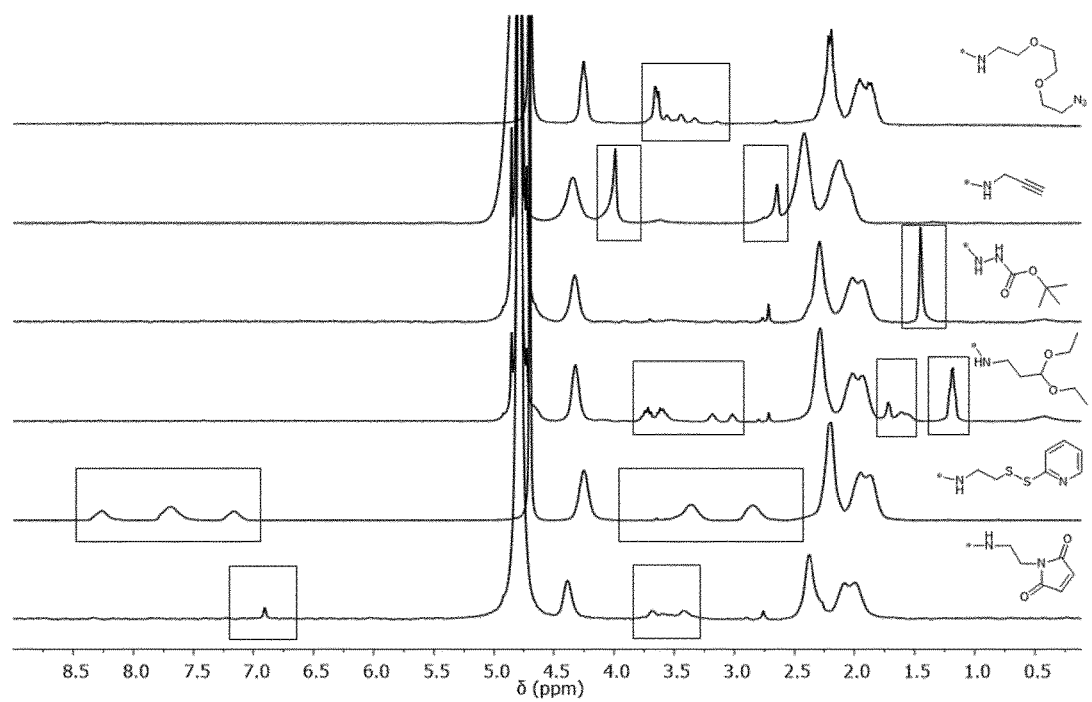
FIG. 6. a) $^1$H-NMR of (compounds formula (II)), St-PGAs with different functionalities in D$_2$O.

FIG. 6 shows selected ¹H-NMR as part of routine characterization of compounds of formula (II).

Example 3. Study of Self and Co-Assembly Behavior Through BTA Motifs of Compounds of Formula (I) and (II)

3.1. Self-Assembly of Compounds of Formula (I).
a) Physico-Chemical Evidences.

Figure 7:
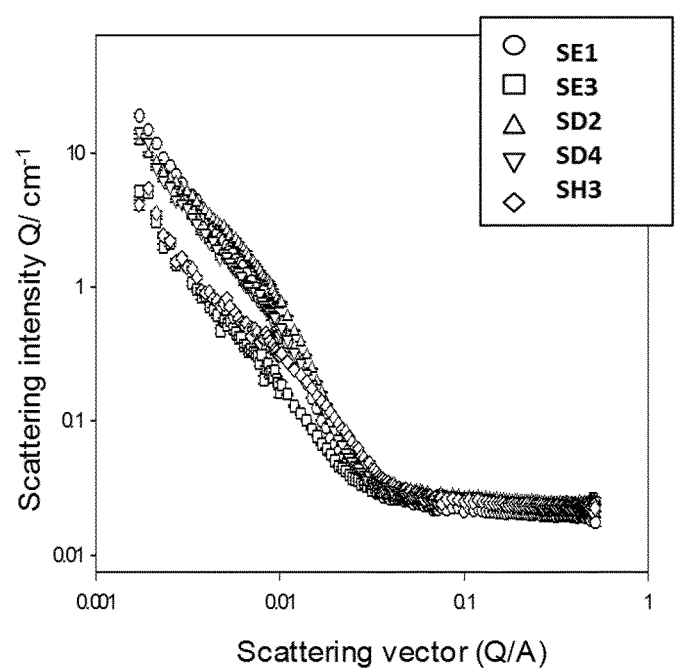
FIG. 7. SANS data plotting of various St-PGAs (compound of formula (I)) at 10 mg·mL$^{-1}$ in PBS buffer at pH=7.4.

When further characterization of our star-shaped systems was carried out, interesting data was found regarding compounds size. Small Angle Nuclear Scattering (SANS) experiments have been performed as routine technique in the lab in order to elucidate size and solution conformation of the compounds of the invention. When these architectures were analyzed by SANS and after adequate data treatment and fittings (FIG. 7), gyration radius were found in the range of 70-160 nm, much higher than the ones expected for single St-PGAs (between 5-10 nm). These experiments were carried out at relatively high concentration (10 mg·mL⁻¹) and therefore, self-assembly could be triggered. SANS fitting analysis correlated these structures with "hard spheres with branches pointing outside".

Figure 8:
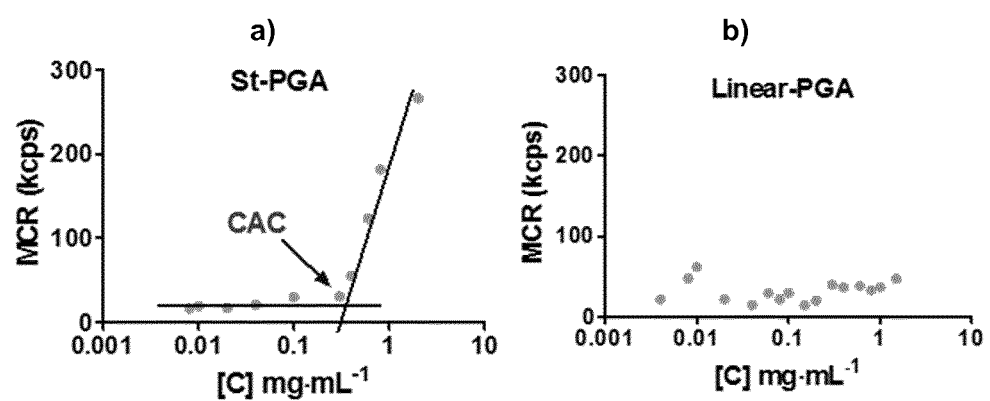
FIG. 8. Size-concentration dependence analysis by DLS in PBS buffer at pH 7.4. a) Mean Count Rate (MCR) vs. concentration of star-shaped polymer with ethyl-based initiator, DP 180 as example (compound of formula (I)). b) Mean Count Rate vs. concentration of linear PGA polymer DP 150 as example.

Moreover, when DLS measurements in PBS buffer pH 7.4 were performed, it was found out that those systems undergo a concentration dependent self-assembly process. At low concentrations "unimers" of 5-10 nm diameter size were identified, whereas bigger structures of around 100-200 nm diameter size were formed at high concentrations. This phenomenon occurred in all star-shaped systems independently on the spacer in BTA core from the initiator (ethyl, hexyl or DOOA, cystamine, Phe-Ethyl). Nevertheless it did not occur in linear PGA (FIG. 8). With increasing concentrations, it could be clearly observed the disappearance of the small structures and progressive appearance of the bigger ones, up to a point where only big structures of 100-200 nm size (diameter) were observed (2 mg·mL⁻¹). By plotting the scattered intensity, Mean Count Rate (MCR) in Kcps obtained against concentration, a value of critical aggregation concentration (CAC) can be obtained with the intersection of the two lineal curves (FIG. 8). This CAC value not only represented the concentration above which aggregation processes were taking place, but also represented the maximum concentration of free non-aggregated polymer species present in the sample under that specific conditions (temperature, ionic strength, pH).

Table 4 summarizes CAC values, hydrodynamic radius ($R_h$) and gyration radius ($R_g$) obtained by DLS and SANS respectively, for several St-PGAs with different initiators and chain lengths. Similar $R_h$ values were obtained for all of the measured stars, however, higher CAC values were observed with greater chain lengths, with the exception of the DOOA initiator. This could be due to the hydrophilicity of this spacer.

TABLE 4

Summary of CAC values, hydrodynamic radius ($R_h$) and gyration radius ($R_g$) obtained by DLS and SANS for different star polymers.

| Star | $R_1$ | GAU arm[a] | CAC.[b] | $R_h$[c] (nm) | $R_g$[d] (nm) |
|---|---|---|---|---|---|
| SD2 | Dooa | 34 | 0.30 | 53.0 | 69.1 |
| SD4 | Dooa | 62 | 0.30 | 47.7 | 91.1 |
| SH3 | Hexyl | 78 | 0.40 | 62.7 | 80.8 |
| SE1 | Ethyl | 33 | 0.20 | 60.1 | 160.7 |
| SE3 | Ethyl | 77 | 0.55 | 123.7 | 84.5 |

[a]GPC in DMF/LiBr at 8 mg·mL⁻¹.
[b]Critical Aggregation Concentration (CAC) measured by DLS (mean count rate vs. concentration) in PBS at 20° C.
[c]DLS data at 2 mg·mL⁻¹ in PBS buffer pH 7.4 at 20° C. expressed by intensity mean.
[d]SANS data (ILL, Grenoble, measured at 10 mg·mL⁻¹ in PBS buffer pH 7.4 at 20° C.

Figure 9:
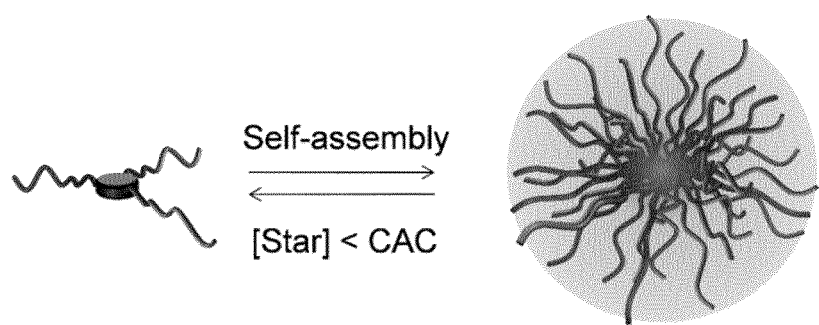
FIG. 9. Schematic representation of the self-assembly process followed by star shaped polyglutamates (compounds of formula (I) and (II)) studied according to DLS and SANS data interpretation.

Accordingly, a self-assembly process is proposed for these systems to lead bigger structures with hard sphere shapes bearing branching points outside directed (FIG. 9). It must be noticed, that self-assembly process of these St-PGAs represents a reversible and dynamic equilibrium between free non-aggregated species and large assemblies with broad size distributions. (FIG. 9.)

Figure 10:
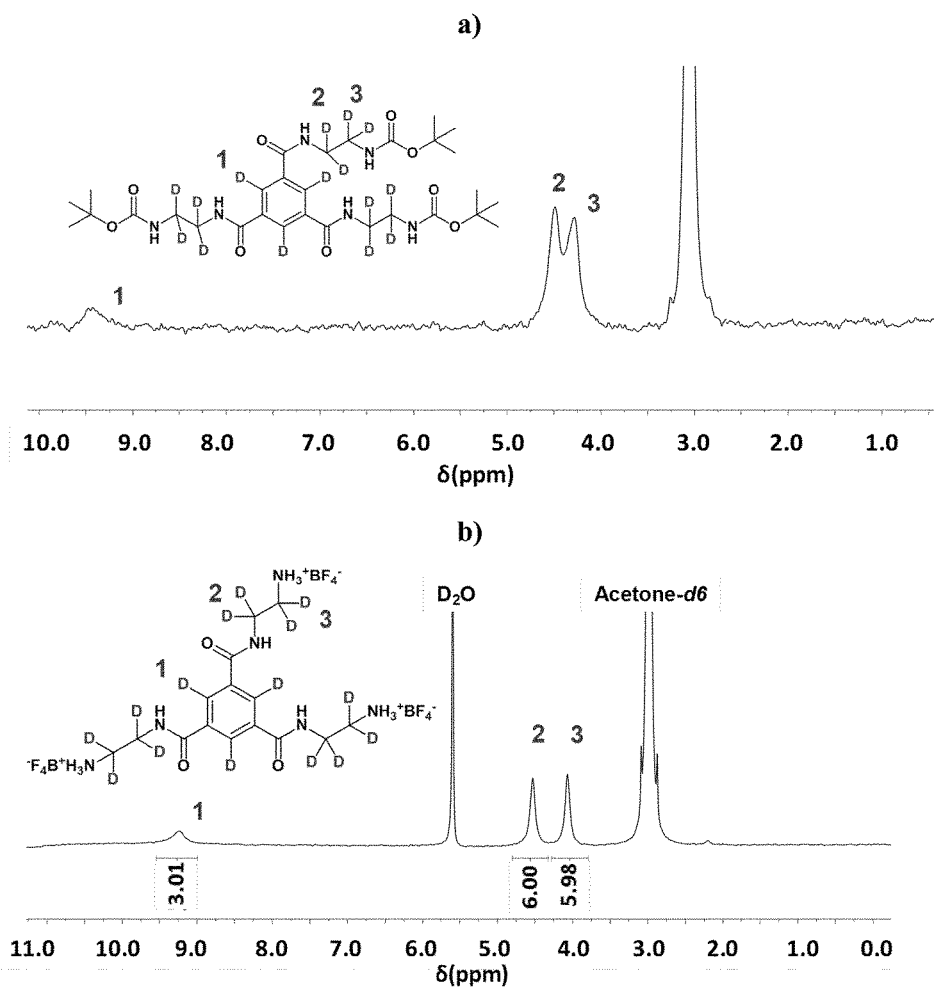
FIG. 10. $^2$H NMR spectra of the D-labeled initiator with corresponding peaks assignments. a) N-Boc-protected initiator in H$_2$O+3 µL Acetone-d6 at 300 MHz. b) BF$_4$ initiator in H$_2$O+3 µL Acetone at 500 MHz.

In order to unravel the molecular organization of BTA core within the assemblies, SANS contrast experiments were performed with D-labeled BTA architectures in LOQ SANS instrument at ISIS (UK). For that purpose, a Deuterium (D) labeled 3-arm initiator was synthesized in two steps using 1,3,5-benzene tricarboxilic acid and N-Boc ethylendiamine both fully deuterated (FIG. 10).

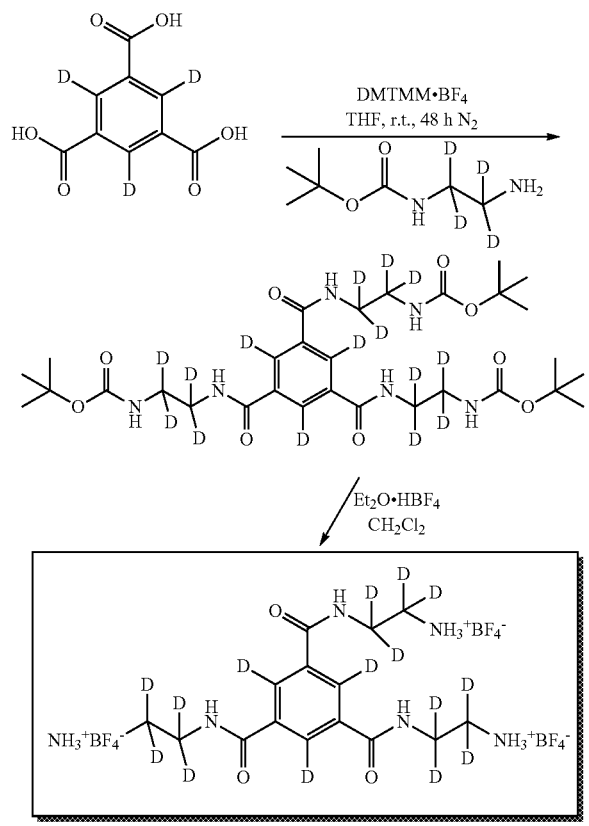

Figure 11:
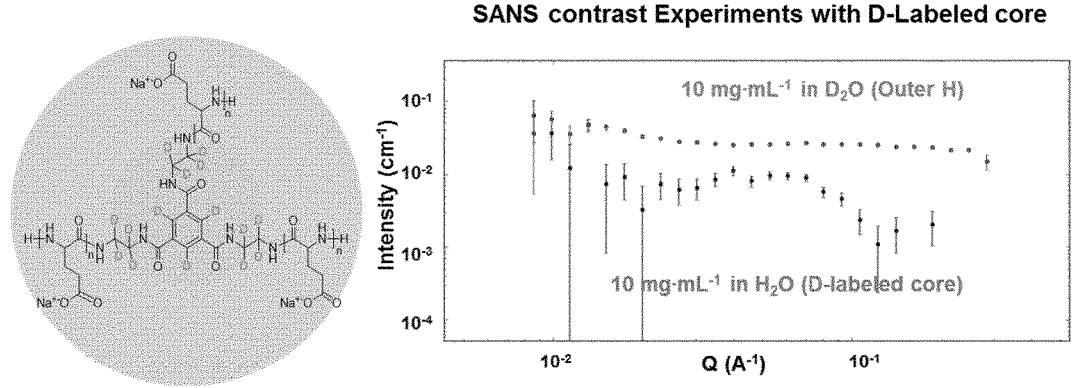
FIG. 11. SANS contrast experiments with D-labeled core in D$_2$O (outer H molecular organization determination) and H$_2$O (D-labeled core molecular organization determination), at 10 mg·mL$^{-1}$ and 20° C. of Deuterated St-PGA (Compound of formula (I)).

This system was studied through SANS contrast experiments both in H$_2$O and D$_2$O solvents. Qualitatively, the contrast experiment in H$_2$O showed a prominent bump compared to the sample in D$_2$O. Aggregation of the self-assembling BTA core resulted in differences on the scattering length density between the hydrophobic domain and the polymer backbone expressed in our system as a "bump" in I(Q) versus Q plot at high Q values (FIG. 11). This feature provided a direct indication of a characteristic 'short' dimension in the structure, suggesting the presence of BTA self-assembled domains. This pointed out the presence of BTA core domains in contrast to a random distribution of BTA moieties along the nanostructure, in agreement with previous reports in literature. This fact confirms that BTA central core is the driving motif for the assembly of these architectures rather than simply the star shape.

Figure 12:
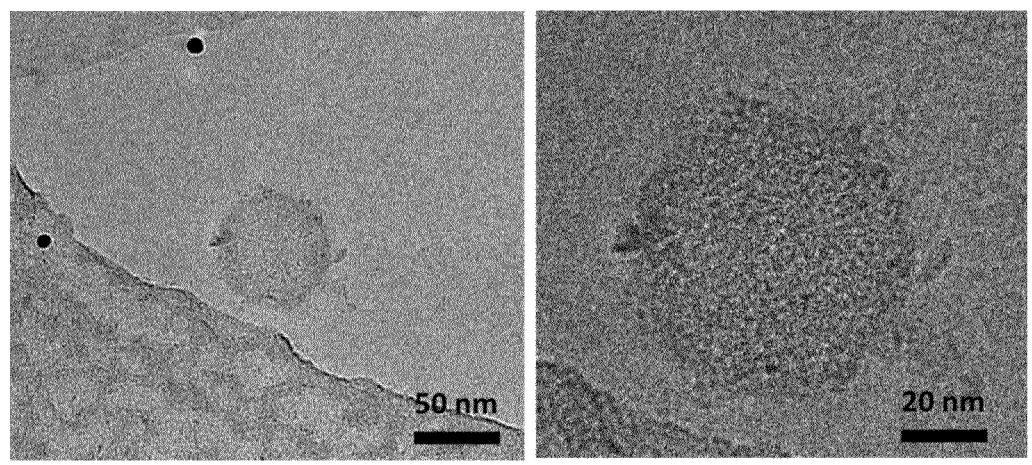
FIG. 12. Cryo-TEM micrographs from St-PGA of a sample (Compound of formula (I)) prepared in ddH$_2$O at 1 mg·mL$^{-1}$ FIG. 13. Ionic strength effect on size of St-PGA (Compound of formula (I)) at 2 mg·mL$^{-1}$ and at 37° C. represented by the changes suffered in scattered intensity (MCR) (left) and in R$_h$ by number (right) upon addition of increasing amount of different salts.

When observed under the microscope using Cryo-Transmission Electron Microscopy (TEM), the star-shaped polymer bearing BTA motifs at the core, exhibited homogenous globular shaped nanoparticles of about 80-100 nm diameter with relatively low dispersities, further confirming the findings obtained in the first SANS experiment and DLS analysis (FIG. 12).

b) Stimuli-Responsiveness.

With size-concentration dependence verified, the effect of different stimuli such as temperature and ionic strength were further investigated using St-PGA without any modification as a model system. Size dependence on ionic strength of media was investigated after the first evidences found (see Table 5) when measuring the same sample in ddH$_2$O or PBS buffer 0.1 M pH 7.4.

TABLE 5

Size determination of St-PGA (ethyl based initiated) by DLS (PBS and ddH$_2$O) and DOSY NMR.

| Compound | $R_h^a$ (nm) | $R_h^b$ (nm) | $R_h^c$ (nm) | $R_h^d$ (nm) | $R_h^e$ (nm) |
|---|---|---|---|---|---|
| St-PGA | 36.4 | 69.1 | 123.7 | 2.7 | 124.4 |

*Data obtained of a 2 mg · mL$^{-1}$ sample from
$^a$DOSY NMR in D$_2$O.
$^b$DLS number mean in ddH$_2$O.
$^c$DLS intensity mean in ddH$_2$O.
$^d$DLS number mean in PBS 7.4.
$^e$DLS intensity mean in PBS 7.4.

Figure 13:
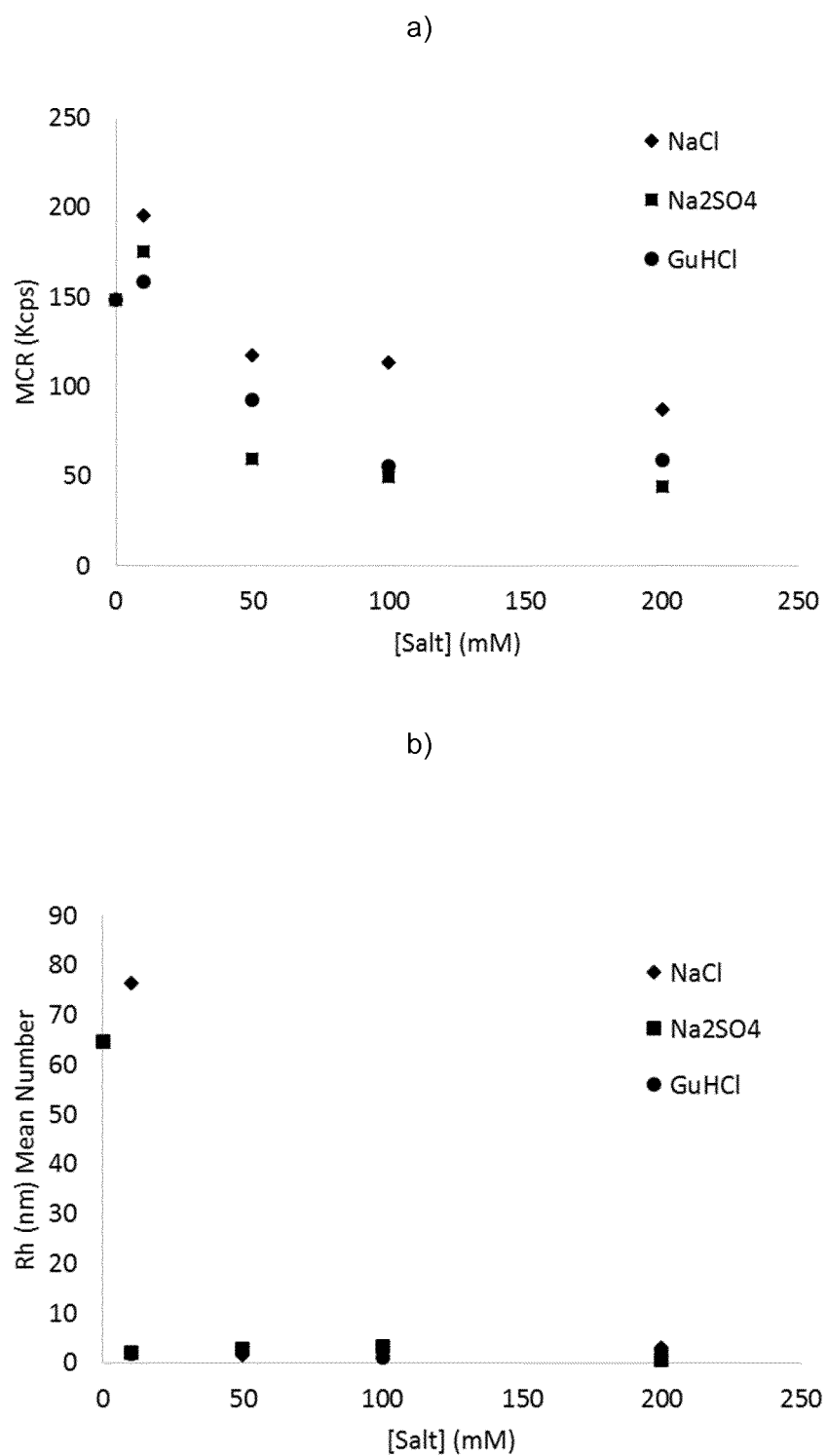

It can be concluded that presence of salt, and therefore, modulation of the ionic strength, highly affects the self-assembly equilibrium by shifting it towards unimer region. In the absence of salts, no unimers could be observed by DLS. Thereafter, ionic strength was further studied as we decided to investigate the influence of different salts on aggregate size (FIG. 13). Sodium chloride (NaCl), guanidinium hydrochloride (GuHCl), and sodium Sulphate (Na$_2$SO$_4$) were chosen due to their different nature. As can be observed in FIG. 13, the scattered intensity is progressively reduced with increasing salt content, being Na$_2$SO$_4$ the most disruptive. Furthermore, R$_h$ (mean number) dependence on salt content reveals disassembly of aggregates just by addition of 50 mM of any salt.

Figure 14:
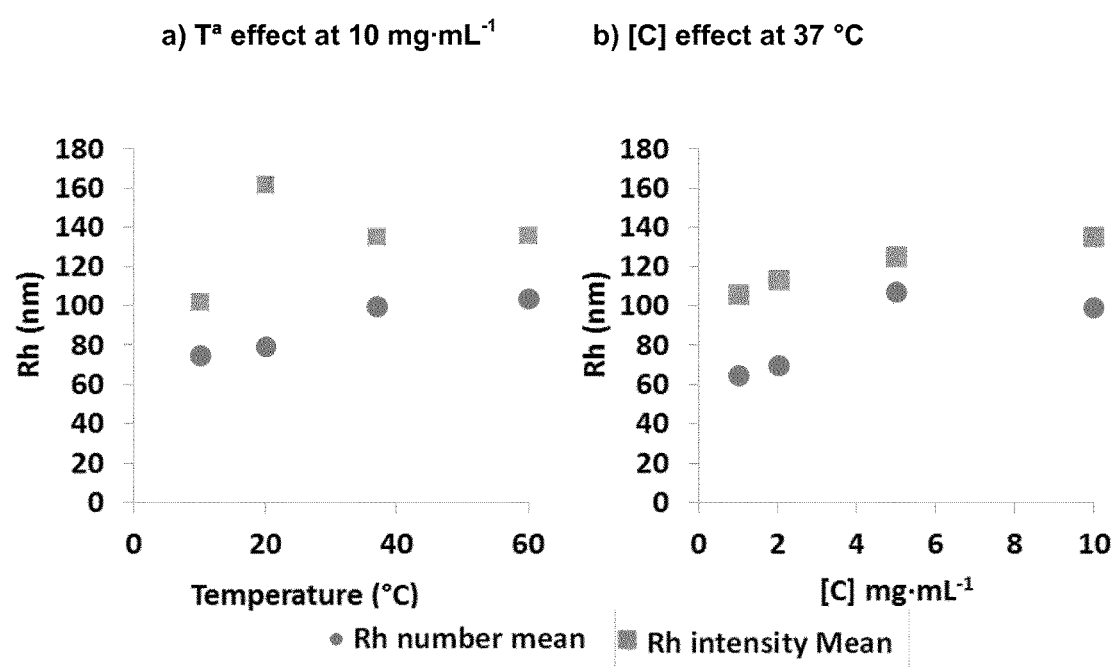
FIG. 14. a) Temperature effect on size of St-PGA (Compound of formula (I)) at 10 mg·mL$^{-1}$. b) Size-concentration dependence of St-PGA (Compound of formula (I)) at 37° C.

Size dependence on concentration was studied at 37° C. in the concentration range of 1 to 10 mg·mL$^{-1}$ St-PGA. As it can be observed in FIG. 14 a sudden increase in size was observed above 5 mg·mL$^{-1}$ from ~70 nm to ~100 nm. Size dependence on temperature was also found when the system was studied by DLS measurements at 10 mg·mL$^{-1}$ in the temperature range between 10 and 60° C.

3.2. Self-Assembly of Compounds of Formula (II).

Figure 15:
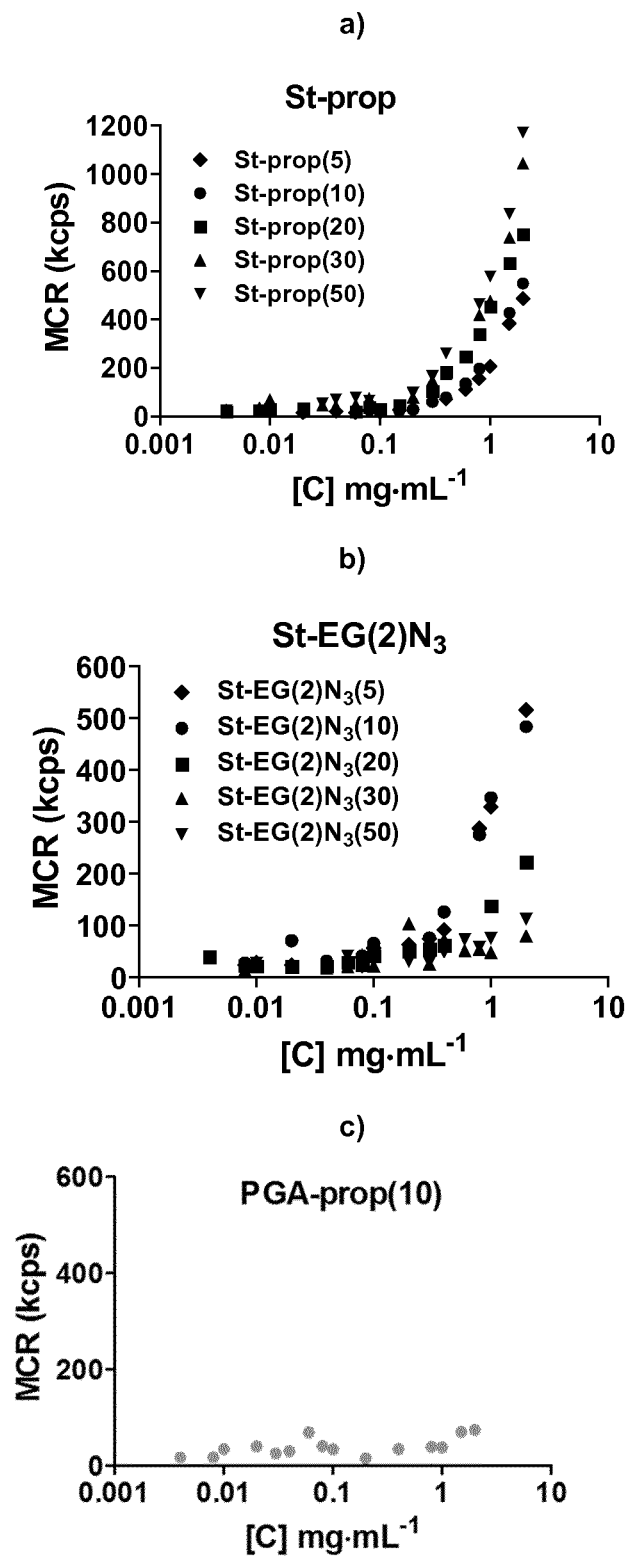
FIG. 15. Mean count rate (MCR) vs. increasing concentrations plotting of a) alkyne modified St-PGAs (Compound of formula (II)) with different degrees of functionalization; b) azide modified St-PGAs with different degrees of functionalization (Compound of formula (II)); c) linear PGA alkyne modified as negative control and d)

For that purpose, several star polymers based on ethyl-BTA initiator were modified with alkynes and azides using the optimized post-polymerization techniques either both in the same polymer chain or in different polymers to yield compounds of formula (II). From 5 to 50% of GAUs (glutamic acid units) of St-PGAs were modified with propargylamine and NH$_2$EG(2)N$_3$ respectively. One polymer was also dually modified with 10% alkyne and 20% azide mol GAUs. Those polymers where analyzed by DLS and CAC was calculated (FIG. 15). As negative control for the study, linear alkyne modified PGAs (5 and 10 mol % GAUs) were also measured leading to absence of aggregation processes in the concentration range studied

TABLE 6

Summary of CAC values and hydrodynamic radius ($R_h$) obtained by DLS of compounds of formula (II).

| Compound | GAU arm[a] | Mod. GAU[b] | CAC[c] | $R_h^d$ (nm) | $R_h^e$ (nm) |
|---|---|---|---|---|---|
| St-prop(5) | 50 | 5 | 0.60 | 44.0 | 67.2 |
| St-prop(10) | 50 | 10 | 0.50 | 38.5 | 77.3 |
| St-prop(20) | 50 | 20 | 0.40 | 37.4 | 68.6 |
| St-prop(30) | 50 | 30 | 0.35 | 49.2 | 95.5 |
| St-prop(50) | 50 | 50 | 0.35 | 45.1 | 90.6 |
| St-EG(2)N$_3$(5) | 50 | 5 | 0.50 | 2.3 | 69.0 |
| St-EG(2)N$_3$(10) | 50 | 10 | 0.55 | 2.7 | 58.2 |
| St-EG(2)N$_3$(20) | 50 | 20 | n.d.* | 2.6 | 75.2 |
| St-EG(2)N$_3$(30) | 50 | 30 | n.d.* | 2.5 | 65.8 |
| St-EG(2)N$_3$(50) | 50 | 50 | n.d.* | 2.6 | 71.1 | n.d. = not determined.
*A CAC could not be calculated in the concentrations range employed. Aggregation (if occurs) might be found over 2 mg · mL$^{-1}$.
[a]GPC in DMF/LiBr at 8 mg · mL$^{-1}$.
[b]Data obtained by $^1$H-NMR in mol %.
[c]CAC measured by DLS in PBS at 20° C. and size measured by DLS at 2 mg · mL$^{-1}$ in PBS at 20° C. by [d]Number mean, and [e]Intensity mean.

Figure 16:
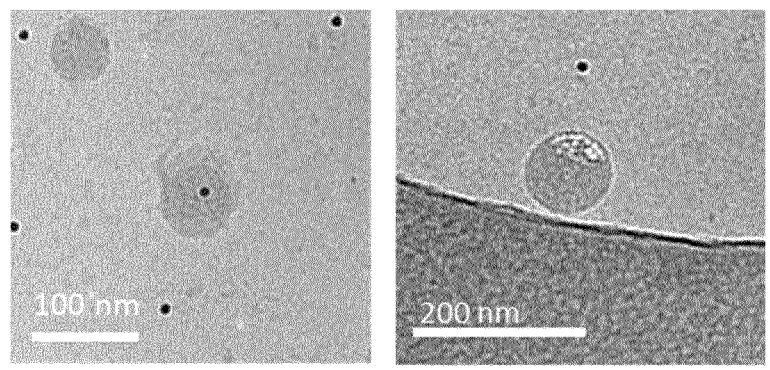
FIG. 16. Cryo-TEM micrographs of modified star polyglutamates (Compound of formula (II)) at 1 mg·mL$^{-1}$ in ddH$_2$O; a) St-EG(2)N$_3$(5); b) St-prop(10).

Assemblies' morphology was also investigated through Cryo-TEM. As shown in FIG. 16, this morphology does not vary significantly from the parent compound with the different chemical modifications introduced. In all cases globular aggregates in the range of 100 nm were found. In general these results are in good agreement with those found for the parent compound and also with DLS and SANS data obtained for these series of compounds.

In a second example, in order to validate the versatility of this approach, different polymer chain modifications (introduction of thiols, maleimides, hydrazides and acetals) in order to perform other covalent capture strategies were implemented. First of all, the synthesis of star-shaped polymers bearing activated di-thiol units (using pyridyl-cysteamine, PD), star polymers with maleimide groups (using NH$_2$—CH$_2$CH$_2$-maleimide, malei), stars bearing hydrazide (hyd) groups and acetals was performed. Compound identity was determined by $^1$H-NMR, (FIG. 6) Their aggregation behavior was also studied by DLS as for the previous compounds, leading to aggregated structures of around 100 nm upon increasing the concentration.

TABLE 7

Summary of CAC values and hydrodynamic radius ($R_h$) obtained by DLS of compounds of formula (II).

| Compound | GAU arm[a] | Mod. GAU[b] | CAC[c] | $R_h^d$ (nm) | $R_h^e$ (nm) |
|---|---|---|---|---|---|
| St-PD(4 | 50 | 4 | 0.6 | 141.55 | 194.4 |
| St-PD(10) | 50 | 10 | 0.55 | 168.78 | 144 |
| St-PD(21) | 50 | 21 | 0.5 | 121.88 | 142.5 |
| St-PD(35) | 50 | 30 | 0.45 | 84.68 | n.d. |
| St-PD(44) | 50 | 44 | 0.3 | n.d. | 138.9 |
| St-PD(60) | 50 | 60 | n.d.* | n.d. | 88.3 |
| St-malei(5) | 50 | 5 | 0.40 | 82.3 | 38.5 |
| St-malei(10) | 50 | 10 | 0.35 | 74.6 | 31.9 |
| St-malei(35) | 50 | 35 | 0.30 | n.d. | n.d. |
| St-hyd(5) | 50 | 5 | 0.5 | 74.6 | 32.9 |
| St-hyd(10) | 50 | 10 | 0.4 | 81.6 | 35.8 | n.d. = not determined;
*C.A.C. could not be calculated in the concentrations range employed. Aggregation (if occurs) might be found over 2 mg · mL$^{-1}$.
[a]GPC in DMF/LiBr at 8 mg · mL$^{-1}$.
[b]Data obtained by $^1$H-NMR in mol %.
[c]CAC measured by DLS in ddH$_2$O at 20° C. and size measured by DLS at 2 mg · mL$^{-1}$ ddH$_2$O at 20° C. by [d]Number mean.
[e]DOSY data in D$_2$O.

3.3. Co-Assembly of Compounds of Formula (II).

Figure 17:
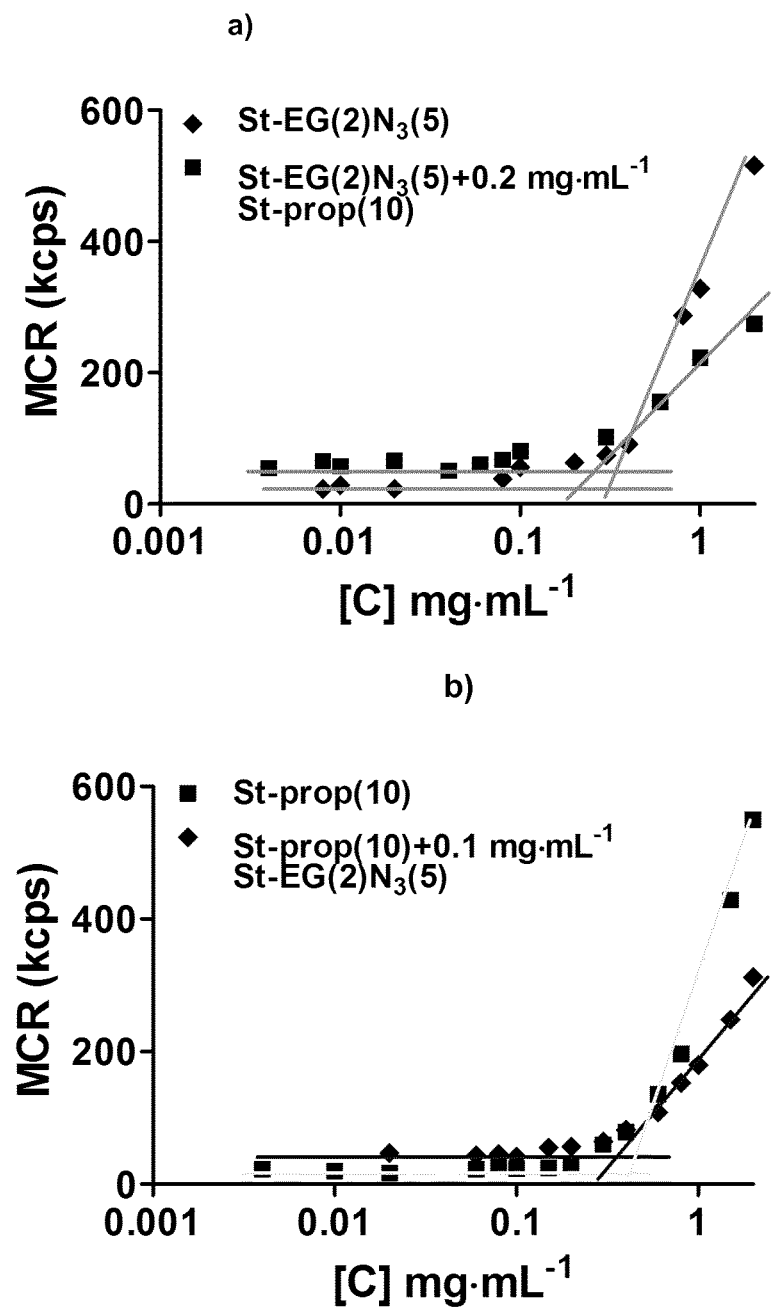
FIG. 17. Co-assembly study by DLS. Graphs showing CAC determination for St-EG(2)N$_3$(5), (Compound of formula (II)), in the presence of constant concentration of St-prop(10), (Compound of formula (II)), (a) and vice versa (b).

Studies to assess co-assembly where done using DLS, by observation of CAC value shift of one of the compounds upon addition of constant amount (always below its CAC) of the second component. Two different series of solutions were prepared for the CAC determination experiments: St-EG(2)N$_3$(5), St-prop(10), and the same series but with addition of the second component in a concentration below their CAC. FIG. 17 shows the plots of scattered intensity against variable concentration of one of the components keeping constant the concentration of the counterpart (always bellow their CAC). It can be seen a decrease in CAC value in both cases when the second compound was added to the solution. These findings somehow suggest a synergy in the formation of mixed assemblies through co-assembly processes what is in good agreement with previous reports on PEG modified BTA species but also block-copolymer systems.

Figure 18:
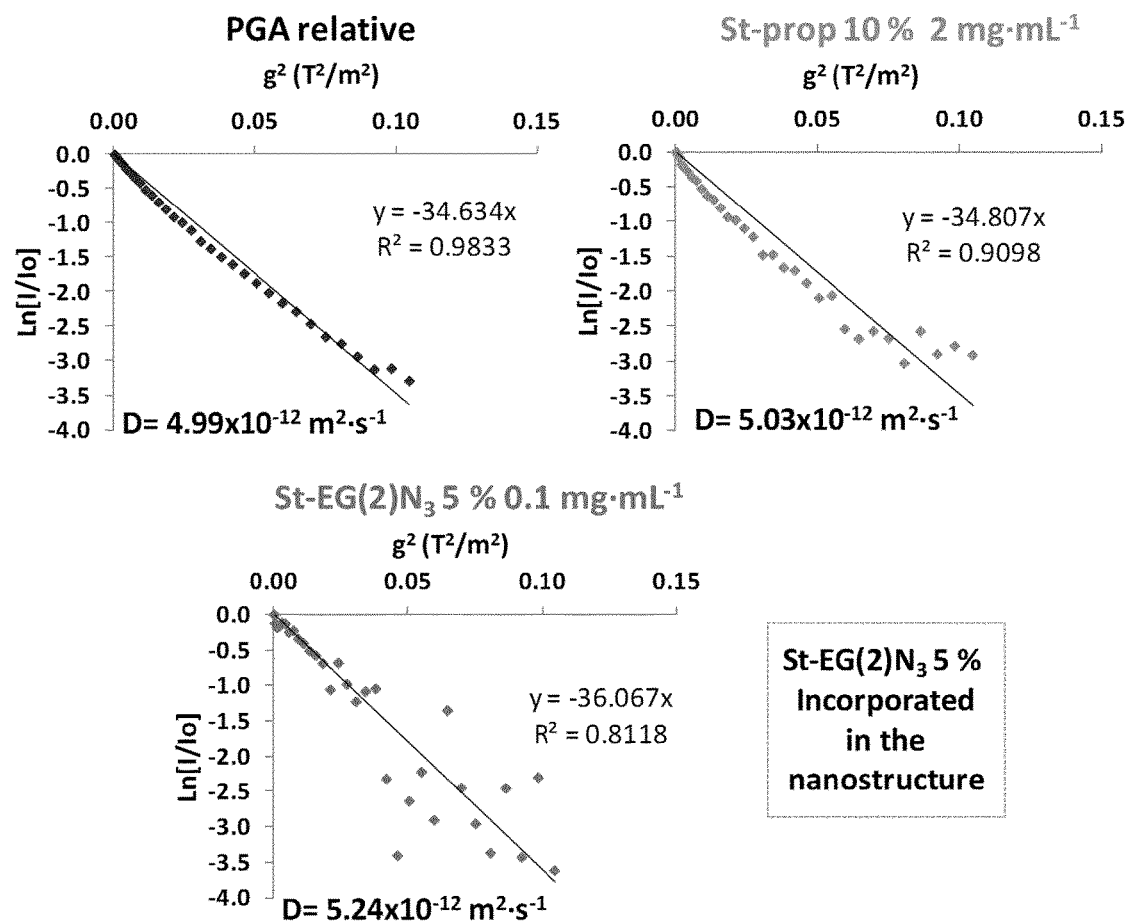
FIG. 18. Co-assembly studies through DOSY NMR of (Compounds of formula (II)), graphs obtained by fitting the intensities of the arrayed DOSY spectra into Stejskal-Tanner equation and the calculated diffusion coefficients (D).

Pulsed-gradient spin-echo NMR spectroscopy, known as diffusion NMR spectroscopy (or DOSY NMR), allows determining the self-diffusion coefficient of the species present in solution. Then, co-assembly process was tested by using a sample containing St-prop(10) above its CAC (2 mg·mL$^{-1}$) in the presence of St-EG(2)N$_3$(5) below its CAC (0.1 mg·mL$^{-1}$). As it can be seen in FIG. 18, $^1$H NMR spectra showed the signals corresponding to each of the components employed in DOSY NMR analysis. After data treatment, it can be seen that compound St-prop(10) shows the characteristic diffusion coefficient of self-assembled species ($5.03 \cdot 10^{-12}$ m$^2$·s$^{-1}$) expected for the concentration studied. However, compound St-EG(2)N$_3$, that, at 0.1 mg·mL$^{-1}$ should present a larger diffusion coefficient when compared to the self-assembled constructs, reduced its diffusion coefficient in one order of magnitude from ($3.12 \cdot 10^{-11}$ m$^2$·s$^{-1}$) to ($5.24 \cdot 10^{-12}$ m$^2$·s$^{-1}$), being virtually equivalent to that found for St-prop(10) component. These results suggest that although St-EG(2)N$_3$ is below the CAC, it moves along with the self-assembled constructs from the counterpart St-prop(10), and thus, indirectly confirms that these architectures are able to co-assemble.

Figure 19:
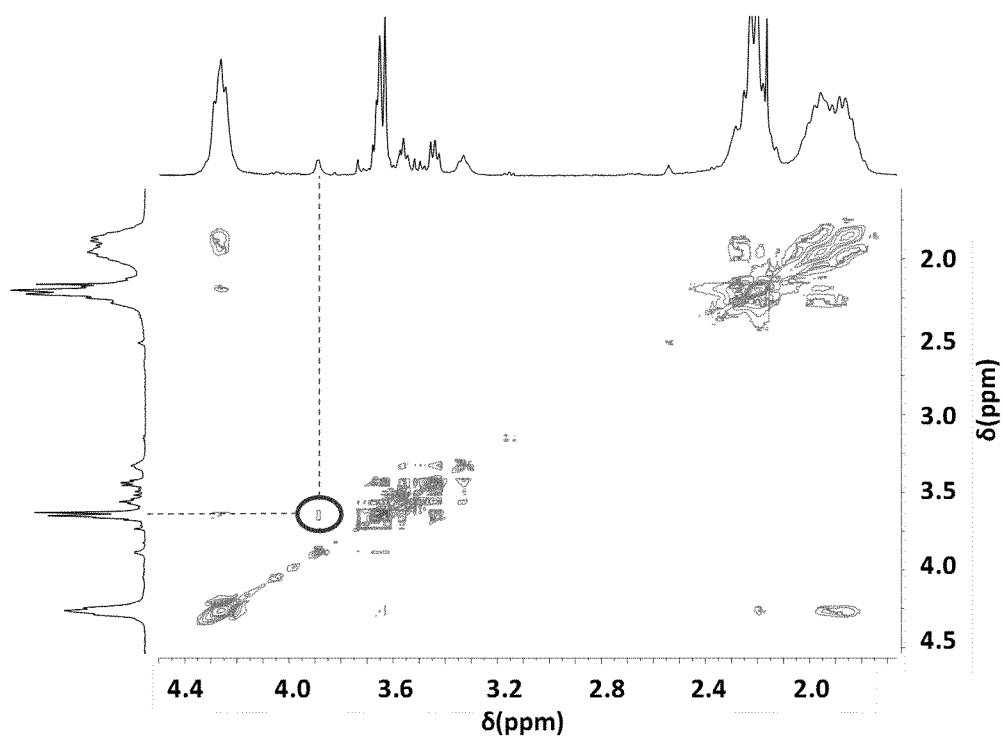
FIG. 19. 2D NOESY spectra showing NOE correlation of propargyl and ethylene glycol protons of a mixture containing 2 mg·mL$^{-1}$ of each compounds of formula (II): St-prop (10) and St-EG(2)N$_3$(5).

Moreover, confirmation of co-assembly process was assessed with the help of NOESY experiments. As observed in FIG. 19, a clear NOE correlation was found for propargyl and ethylene glycol signals, a result that confirms the spatial proximity between both groups.

Example 4: Synthesis of Compounds of Formula (III)

Figure 20:
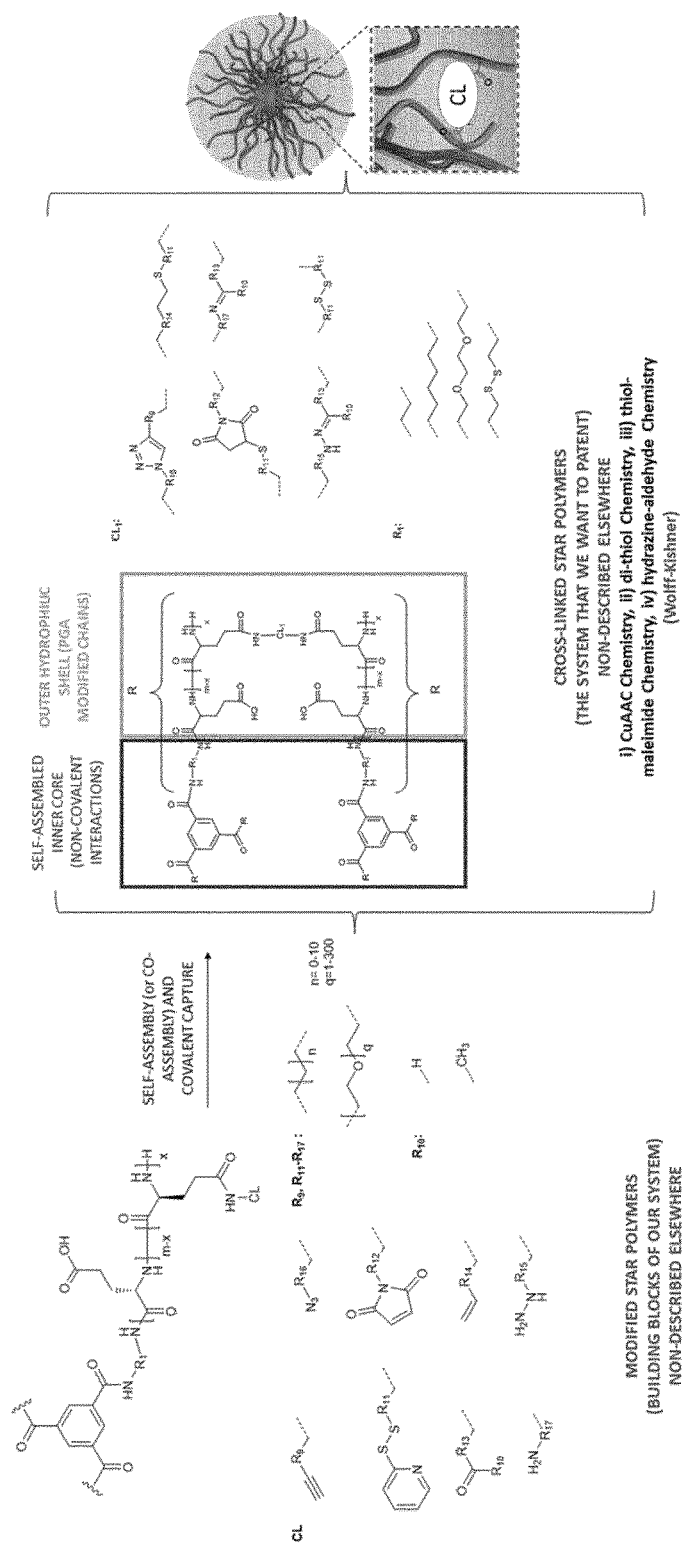
FIG. 20. Schematic representation of covalent capture of co-assembled star-shaped polymers bearing orthogonal functionalities (Compounds of formula (II) and (III)) exemplified for PGA.
Figure 21:
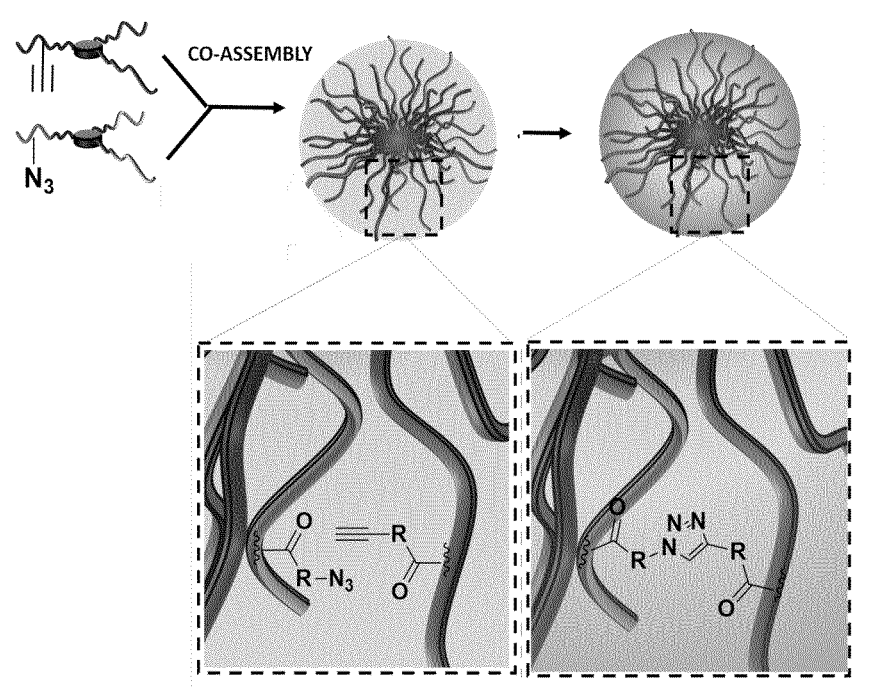
FIG. 21. Schematic representation of covalent capture of co-assembled star-shaped polymers bearing orthogonal functionalities (Compounds of formula (II)) (specific case of alkynes and azides) through CuAAC click chemistry yielding compounds of formula (III).

A general scheme of the proposed methodology to self-assemble the star-shaped polyglutamates into well-defined morphologies and stabilize the aggregates through covalent cross-linking is depicted in FIG. 20 including all the chemical and structural variations. The following non limiting example is intended to illustrate the bottom up approach (see FIG. 21) employed for the construction of these complex carriers employing the propargyl and azide functionalized derivatives.

Methodology for copper catalyzed alkyne-azide coupling (CuAAC) of St-PGA derivatives: using the compounds of formula (II), star-shaped polymers St-prop(10) (Star PGA based on BTA-ethyl and modified with propargyl amine units 10 mol %) and St-EG(2)N$_3$(5) (Star PGA based on BTA-ethyl and modified with oligoethylene glycol azide units 5 mol %): Those polymers were chosen in order to have an excess of propargyl units to ensure complete conversion, as the reaction will be performed in equimolar ratio of both functionalities. The reaction was carried out in ddH$_2$O (constructs were present in aggregated state as seen before), using a concentration to ensure the only presence of big structures within the polymeric mixture (ratio 1:1, 2 mg·mL$^{-1}$). The mixture was firstly sonicated for 5 minutes in order to promote homogenization. Then, 5 eq. of sodium ascorbate in ddH$_2$O solution were added. Then, the mixture was degassed by performing two freeze-pump-thaw cycles. One eq. of CuSO$_4$ was weighted under N$_2$ flow and added in ddH$_2$O solution to the reaction mixture. The final complete mixture, was degassed by performing another freeze-pump-thaw cycle and left to react at 40° C. in an oil bath protected from light. Complete conversion was achieved after 3 days, according to $^1$H-NMR (triazole signal at 7.8 integrates for 5 mol %). Other coupling chemistries encompassing i) di-thiol Chemistry, ii) thiol-maleimide Chemistry, iii) hydrazine-aldehyde Chemistry (Wolff-Kishner) were also carried out.

Figure 22:
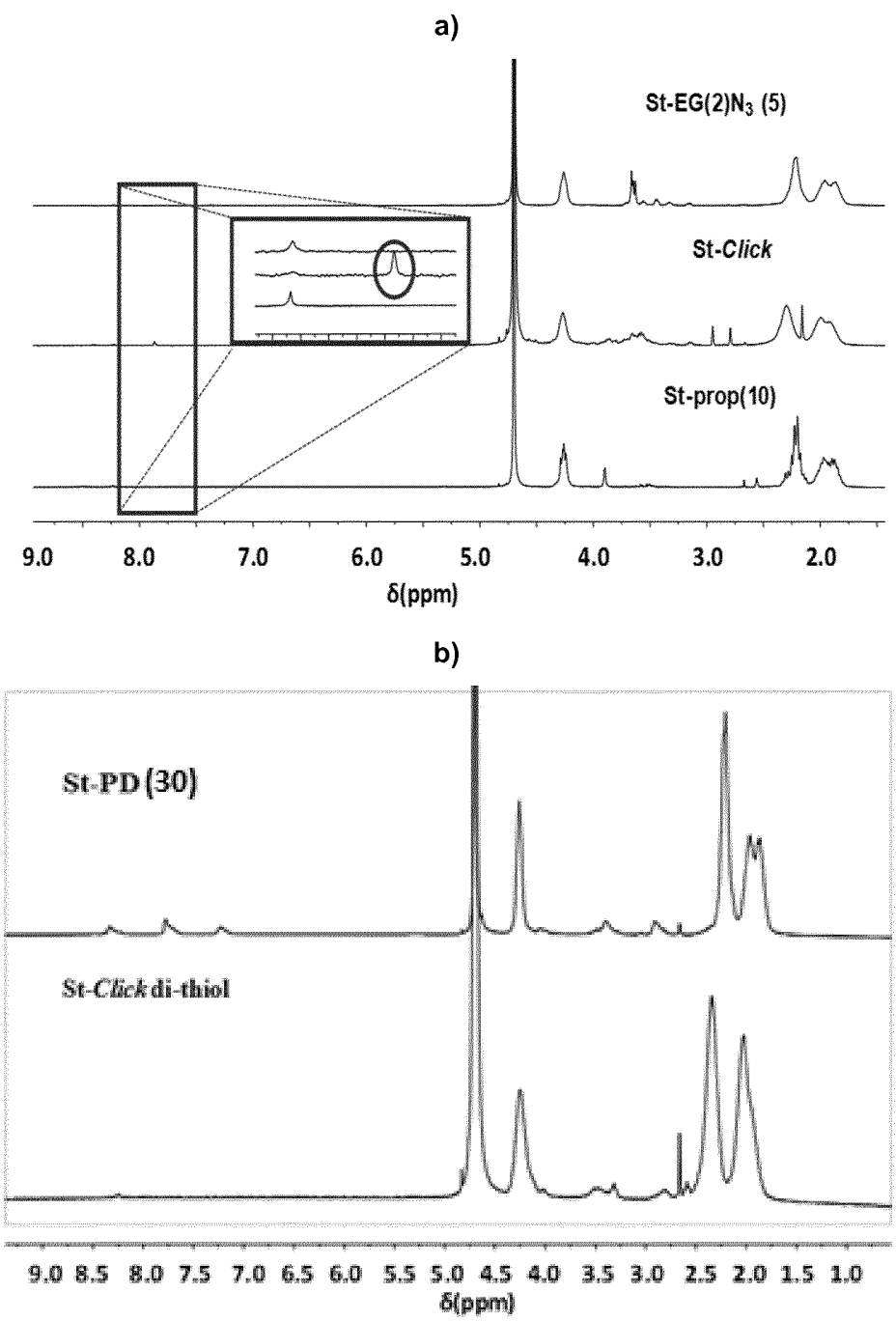
FIG. 22. $^1$H-NMR in D$_2$O of compounds of formula (III) obtained by different cross-linking chemistries as example, and compared with their precursors compounds of formula (II). a) Cross-linked system (formula (III)) by CuAAC chemistry and St-prop(10) and St-EG(2)N3 (5), (compound of formula (II)). b) Cross-linked system (formula (III)) by di-thio chemistry and St-PD(30) (compound of formula (II)).

The products obtained were characterized by $^1$H-NMR and results shown in FIG. 22.

Figure 23:
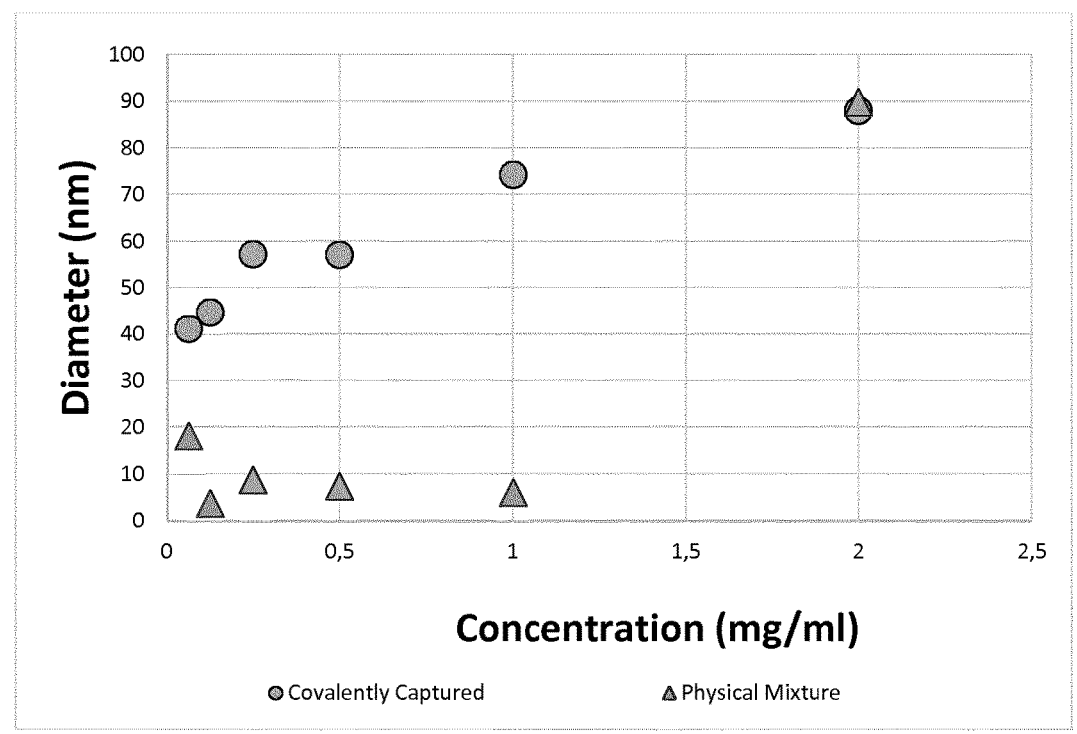
FIG. 23. Comparison of both measured systems (compounds of formula II physically mixed, and compound of formula III) in terms of size against concentration. All values correspond to measurements in PBS 7.4 and are represented in number.

Additionally, the clicked system was studied by DLS measurements in comparison with a physical mixture 1:1 of both components separately after sonication. Dilution experiments were performed by diluting both samples up to 32 fold 1 mg·mL$^{-1}$ stock solution. In the case of the physical mixture, two different structures were already found at the first dilution (1:2 ratio). Nevertheless, for the clicked construct, only big structures of about ~80-100 nm diameter were encountered, even at ⅟₃₂ of the initial concentration (~0.03 mg·mL$^{-1}$) (FIG. 23). The small decrease in the assemblies found for the clicked system (from 45 to 30 nm in radius) might be due to the low eq. of effective cross-linking groups (in this case azide, 5 mol %) resulting in an incomplete cross-linking of the self-assembled nanostructures.

Figure 24:
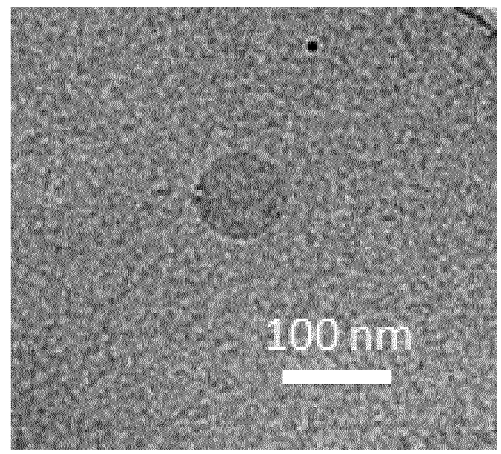
FIG. 24. Cryo-TEM pictures at 2 mg·mL$^{-1}$ of compounds of formula (III).

Cryo-TEM pictures of the clicked system confirmed the formation of spherical structures with a diameter size~100 nm (FIG. 24).

Covalent capture using di-thiol chemistry, was performed at concentrations of 10 mg mL$^{-1}$ for each compound in ddH$_2$O for di-thiol chemistry and PBS buffer at pH 7.4 for thiol-ene, due to the need of controlling the pH over reaction time in order to guarantee maleimide group stability. After purification by dialysis, the success of the entrapment was ratified by $^1$H-NMR. (FIG. 22) In the case of di-thiol chemistry confirmation was achieved by disappearance of the aromatic signals corresponding to pyridyl groups while CH$_2$ signals of cysteamine were kept, in the case of di-thiol chemistry. For thiol-ene reactions, the absence of the characteristic maleimide peak around 6.7 as well as the pyridyl signals were indicatives of effective couplings. DLS and TEM measurements confirmed the covalent capture leading to stable structures of around 100 nm diameter.

Example 5. Synthesis of Conjugates Comprising Compounds of Formula (I), (II) or (III) and an Agent Modification of glutamate residues is carried out under analogous conditions for all the compounds comprised in formulas I, II and III. To simplify, the general synthetic strategy is illustrated for a general poly-L-glutamic acid backbone as depicted bellow:

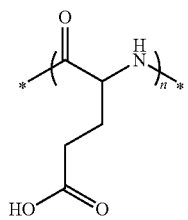

5.1. Conjugation of Oregon Green Cadaverine to Compounds of Formula (I), (II) or (III):

For macromolecular therapeutics and nano-sized drug delivery systems, fluorescent labeling is commonly applied to allow intracellular trafficking studies, conjugate cell-specific localization and/or in vivo fate and PK. Probes such as the fluorophore Oregon Green (OG) have been extensively reviewed for cellular studies to determine cell uptake and binding. To this aim, the conjugated probe must fulfill some requirements such as high stability of the probe itself as well as stability of the linkage to ensure adequate carrier monitoring. On the other hand, a minimal percentage of probe loading is desirable in order to avoid data misinterpretation due to changes in polymer conformation resulting from changes in charge and solubility. In order to fulfill all that criteria, less than 1 mol % of OG was conjugated through a non-biodegradable amine bond. Conjugation of OG to the clicked system was carried out either by using diisopropylcarbodimide (DIC)/Hydroxybenzotriazole (HOBt) as carboxylic acid activators in organic solvents or DMTMM.Cl in aqueous solution. The protocol of OG conjugation was previously established and routinely used with DIC/HOBt in Dr Vicent laboratory, ensuring 80-90% conjugation efficiency of the fluorescence dye. A schematic representation of polymers labeling is depicted in the following scheme:

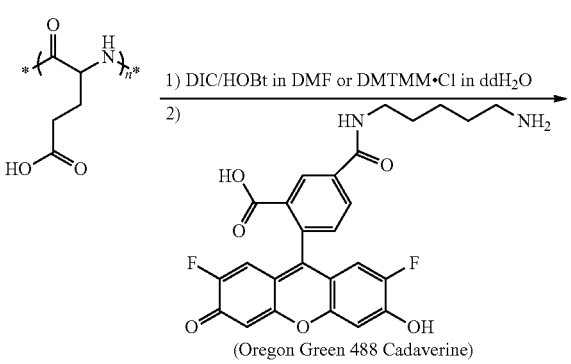

(Oregon Green 488 Cadaverine)

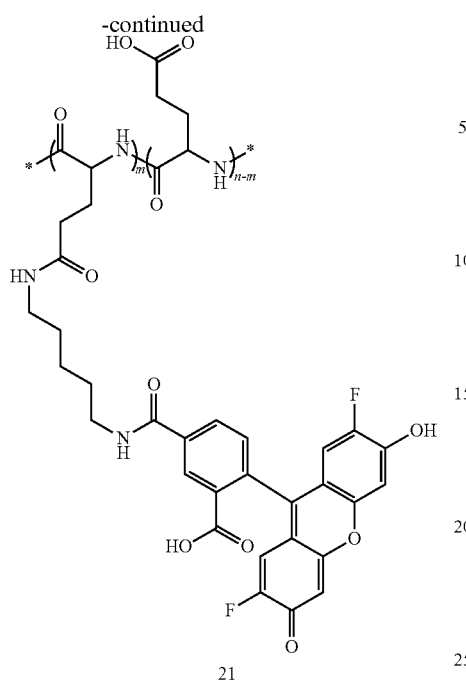

In a round two necked bottom flask fitted with a stirrer bar and two septums, 29 mg of compounds of formula (I), (II) or (III) (0.225 mmol glutamic acid units or GAU, 1 eq.) was weighed and dissolved in 1.5 mL of dry DMF under $N_2$ flow. Of N, N'Diisopropylcarbodiimide (1.12 μL) and DIC (0.85 mg, 0.00674 mmol, d=0.806 g/mL, 0.03 eq.) were added and the reaction was left to proceed for 5 min at room temperature. Afterwards, Hydroxybenzotriazole, HOBt (1 mg, 0.00674 mmol, 0.03 eq.) was added directly. The reaction was then left to proceed for 10 min before Oregon Green Cadaverine (1 mg, 2.25·10⁻³ mmol, 0.01 eq.) was added. The pH was adjusted to 8 by adding ~100 μL of DIEA. The mixture was left stirring overnight protected from light. Finally, the solvent was removed under vacuo at room temperature and the product was dissolved in 300 μL of water and then adding ~50 μL of $NaHCO_3$ 1M. The solution was purified by Sephadex PD10 column eluting with distilled water. The Oregon Green (OG) loading was calculated by fluorescence using a Victor²Wallace™ plate reader with excitation filter of 490 and emission filter of 535. A calibration curve with OG was first performed. Yield: 95%. OG loading: 0.8 mol glutamic acid unit.

5.2. Conjugation of Cy5.5 to Compounds of Formula (I), (II) or (III).

Briefly, in a one-neck round bottom flask, PGA-based polymer was dissolved in $ddH_2O$ (1 eq. GAU). Then, the carboxylic groups were activated using DMTMM.Cl (i.e. 0.02 eq. for 2% modification). Reaction was allowed to proceed for 10 minutes. After that time, Cy5.5 (i.e. 0.02 eq. for 2% modification) was added in $ddH_2O$. The pH was adjusted to 8 by adding sodium bicarbonate 1 M. Reaction was left to proceed for 24 hours, protected from light. For purification, the products were submitted to both Sephadex G25 and dialysis using Vivaspin® MWCO 5000.

Cy5.5 content estimation was carried out by fluorescence ($A_{em}$: 595 nm, $A_{ex}$: 680 nm) after the building of an appropriate calibration curve of Cy5.5 dye in PBS buffer.

Yields: 60-70%. Conjugation efficiency 70-90%.

5.3. Conjugation of $DO_3AtBu-NH_2$ to Compounds of Formula (I), (II) or (III):

As for OG conjugation, DIC/HOBt as carboxylic acid activators in organic solvents or DMTMM.Cl in aqueous solution were used.

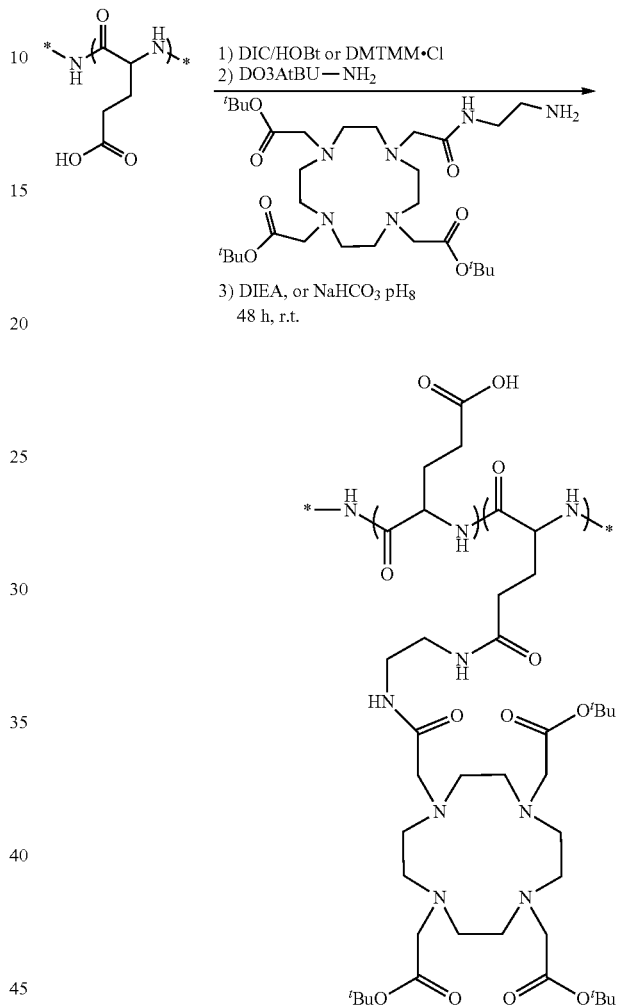

In a two-neck round bottom flask fitted with a stir bar and two septums, 300 mg (of St-PGA), 110 GAU, 2.32 mmol GAU, 1 eq.) was dissolved in 20 mL of anhydrous DMF under nitrogen flow. Then, 53 μL of DIC (88 mg, 0.70 mmol, 0.3 eq.) were added and the reaction was left to proceed for 5 min at room temperature. Afterwards, HOBt (94 mg, 0.70 mmol, 0.3 eq.) was added directly. The reaction was then left to proceed for 10 min before $DO_3AtBu-NH_2$ (282 mg, 0.46 mmol, 0.2 eq.) was added for 20% modification. The pH was adjusted to 8 by adding ~100 μL of DIEA. The mixture was left stirring for 48 hours at room temperature and protected from light. Finally, the solvent was partially removed under vacuo, precipitated into a large excess of cold acetone, filtered off and washed three times with cold acetone. A pale yellow solid was obtained after drying. The percentage of modified GAU was calculated as 20% mol GAU, according to the tBu groups signal at 1.4 ppm in comparison with the alpha proton of PGA backbones in ¹H-NMR spectra. Conjugation efficiency: 100%. Yield: 75%.

Deprotection of DO₃A tBu-NH:

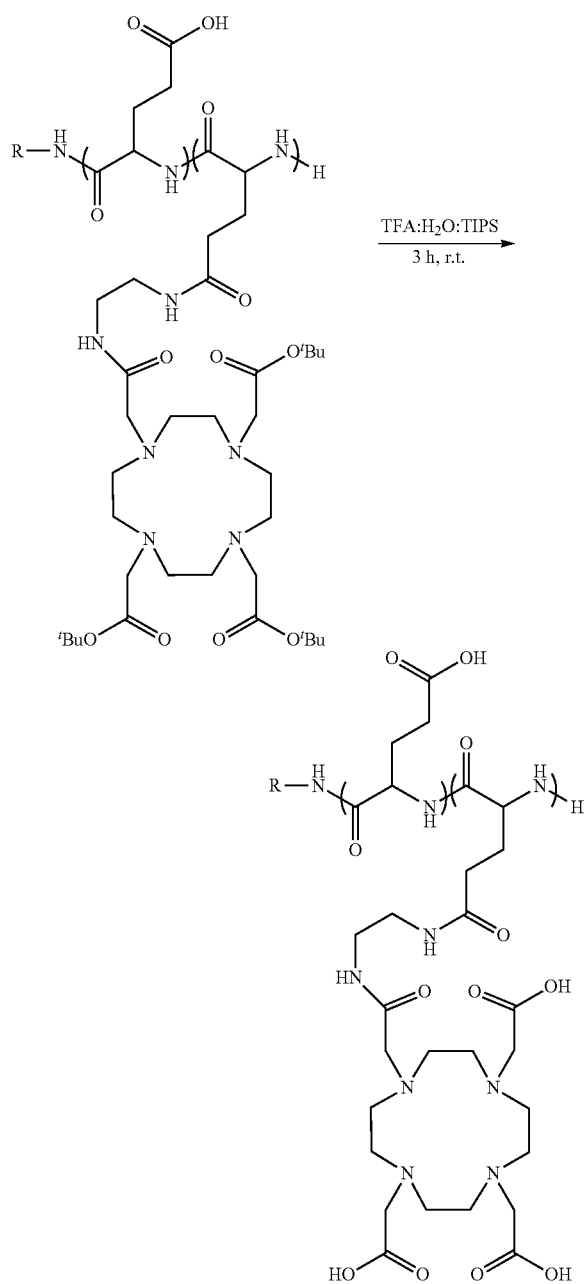

Two different protocols were used depending on the compound nature. For constructs without any sensitive group to trifluoroacetic acid (TFA) conditions, the first protocol was applied. The use of Triisopropylsilyl ether (TIPS) in the second protocol was introduced in order to prevent disulfide bonds breakage during deprotection conditions.

Protocol 1. The construct was dissolved in CH₂Cl₂/TFA (3/2, v/v) mixture and left under vigorous stirring for 16 hours at r.t. After that time, the solution was precipitated by pouring into a large excess of cold diethyl ether. Pale yellow solid was obtained after filtering, washing with diethyl ether and drying under vacuum. Complete deprotection was achieved as confirmed by ¹H-NMR. Yields: 80-90%.

Protocol 2. The construct was dissolved in TFA/H₂O/TIPS (95/2.5/2.5, v/v) mixture and left stirring at r.t. during 3 hours. After that, the contents were precipitated into a large excess of cold diethyl ether. A pale yellow solid was collected, washed with diethyl ether and dried over vacuum. Complete deprotection was confirmed by ¹H-NMR analysis. Yields: 80-90%

5.4. Radiolabelling with ¹¹¹In of Compounds of Formula (I), (II) or (III).

As example, St-PGA-DO₃A-¹¹¹In was prepared by dissolving 51.3 mg of St-PGA-DO₃A in deionized water to a final concentration of 10 mg/mL. Then, 0.25-0.5 mL of this dissolution was transferred into a microwave tube and the pH was adjusted to 3.5-4 by adding HEPES buffer and HCl 2 M. Next 7-27 MBq of ¹¹¹InCl₃ in HCl 0.05 M was added and the reaction mixture heated at 90° C. for 5 min by using a laboratory microwave with monomodal radiation (Discover Benchmate, CEM). After that, the reaction mixture was cooled down with nitrogen gas. The reaction was stopped after 5 min at room temperature by the addition of 50 µL of 50 mM ethylenediaminetetraacetate acid (EDTA). St-PGA-DO3A-¹¹¹In was purified from unreacted ¹¹¹In-EDTA by exclusion molecular chromatography cartridge (Bio Gel P-6, BioRad) using phosphate buffered saline (pH=7) as eluent, at flow rate 0.5 mL/min. The elution profile was determined by fractionating, 0.77 mL per fraction, and measuring each with a dose calibrator (VDC 405, Veenstra). Radiochemical yield (RY) was calculated as percentage of the activity in each fraction eluted from the molecular exclusion cartridge of the total activity purified and corrected for the decay.

5.5. DO3A-Gd³⁺ Labeling for MRI of Compounds of Formula (I), (II) or (III).

In a one-neck round bottom flask, the corresponding DO3A bearing polymer as sodium salt form (1 eq. of modified DO3A GAU units) was dissolved in PBS 0.1 M pH 7.4. Then, GdCl₃ (1 eq.) dissolved in ddH₂O was dropped into the main solution. During this process, pH was monitored and remained constant to 8. The degree of Gd (III) complexation was determined by titrating aliquots during reaction process using 4-(2-pyridylazo) resorcinol which turns from yellow to orange in the presence of free Gd). No free Gd was detected after 5 hours reaction time. The reaction was then stopped and purified by dialysis using Vivaspin® MWCO 5000. Absence of free Gd was again confirmed by using the titrating method described before with the dialyzed contents.

Figure 25:
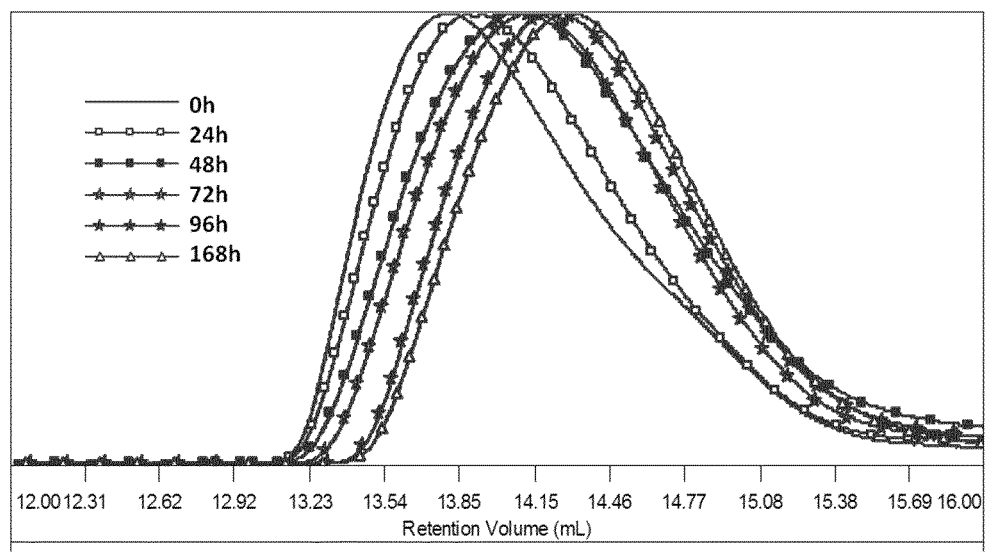
FIG. 25. In vitro evaluation of the newly synthesized St-PGA ((compounds formula (I)) carriers. a) Example of degradation profile by cathepsin B monitored by GPC in PBS at 3 mg/mL and at different time points. b) Toxicity assay against SHSY5Y cell line of different St-PGAs (compounds formula (I)) measure by MTS assay at 72 hours post-treatments. c) Toxicity assay against HUVEC cell line of different PGA based architectures measure by MTS assay at 72 hours post-treatments. DB: Di-block PEG$_{42}$PGA$_{200}$; PGA: linear PGA$_{250}$; STAR: St-PGA$_{250}$ FIG. 26. In vitro evaluation of the newly synthesized carriers. a) Uptake study by flow cytometry of a star-shaped fluorescently labeled PGA (compounds formula (I)) in SHSY5Y cell line. Experiment at 4° C. excludes the energy dependent mechanisms. The different among the uptake profile at 4 and 37 degrees (so-called "Energy-dependent" uptake) is also represented. CAF: Cell associated fluorescence=% positive cells*mean fluorescence/100. The CAF represented corresponds to the difference between CAF obtained with treated cells and CAF from untreated control cells. b) Confocal image of the uptake at 2 hours post-treatment of a star-shaped PGA in SHSY5Y cell line following a pulse-chase experiment, with co-localization histogram. Co-localization with the lysosomal marker Lysotracker Red was observed.
Figure 25:
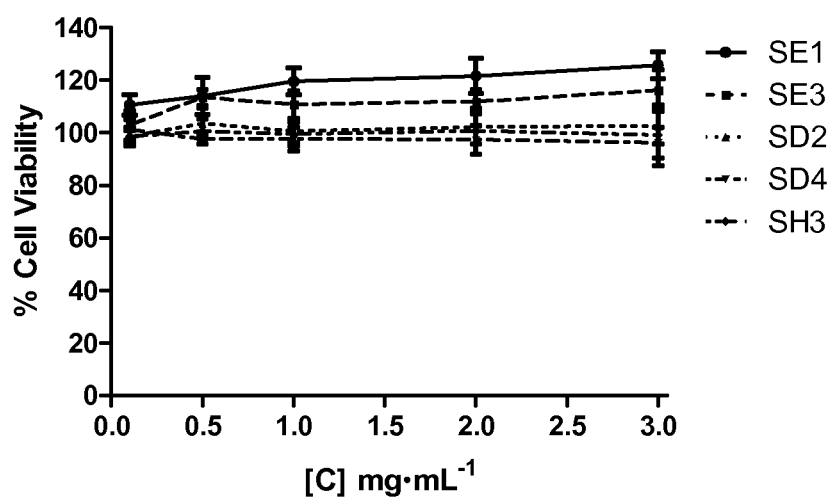

Example 6: Validation of Compounds of Formula (I) as Carriers 6.1. Degradation with Cathepsin B:

To be sure that the enzyme-dependent biodegradability of the polyglutamate-based stars had not been compromised by the architecture, all polymers were incubated in presence of the lysosomal enzyme cathepsin B. St-PGA was degraded in presence of the lysosomal enzyme cathepsin B as its linear counterpart. To test the profile and ratio of the degradation of the polymers by cathepsin B, solutions of the St-PGAs (3 mg/mL) were prepared. 3 mg exactly were weighed and 700 µL of acetate buffer 20 mM, pH 6, 100 µL of EDTA 2 mM, 100 µL of DTT 5 mM were added. Finally, 6.25 units of Cathepsin B (100 µL of a solution of 25 units of cathepsin B in 400 µL of acetate buffer pH 6 20 mM were added. Cathepsin B needs pH 6 to be active, the DTT solution is added to activate Cathepsin B and the solution of EDTA was added to complex the free cations (mainly Ca²⁺ that inactivates cathepsins). Once the solutions were prepared, aliquots of 100 μL were picked at different time points (t=0, 0.5, 1, 2, 4, 8, 24, 48 and 72 hours) after homogenization of the solutions. Meanwhile, the samples were kept at 37° C. under stirring. The aliquots taken were frozen and later analyzed by GPC. To evaluate the mass of the conjugates, 100 μL of 3 mg/mL conjugate solution in PBS was injected in the GPC using two TSK Gel columns in series G2500 PWXL and G3000 PWXL with a Viscoteck TDA™ 302 triple detector 87 with UV detection coupled. The mobile phase used was PBS 0.1 M, flow 1 mL/min As expected, the star polymers were found to be degraded by the lysosomal enzyme with similar kinetics independently of the MW and initiator used for the polymerization (FIG. 25a).

6.2. Cell Viability.

Another key feature for the validation of the compounds of the invention as potential drug delivery carriers or imaging probes is their toxicity in cell cultures. To this respect, 72 hours MTS assays (3-(4,5-dimethylthiazol-2-yl)-5-(3-carboxymethoxyphenyl)-2-(4-sulfophenyl)-2H-tetrazolium colorimetric agent assay) were performed against SHSY5Y human derived neuroblastoma cell line as well as in HUVEC (human umbilical vein endothelial cells). Polymers were found to be non-toxic up to 3 mg/mL (FIGS. 25b and c).

6.3. Cellular Uptake.

Understanding of cellular internalization mechanisms used by nanopharmaceuticals has become a key player in the field of drug delivery. Nanomedicines mainly use endocytic vesicles or endosomes, which in turn employ a complex mechanism to address the different molecules to specific intracellular locations. It can be said that charge, shape, material composition, and surface functional groups are basic physico-chemical parameters that determine cell entry of nanomedicines by endocytic pathway.

Confocal microscopy techniques and flow cytometry are routinely used with fluorescence-labeled polymers in order to evaluate their uptake by cells. Live-cell confocal imaging, allows visualizing trafficking between multiple compartments within individual living cells over time, avoiding any possible artifacts derived from fixation protocols. On the other hand, flow cytometry give us semi-quantitative information about the mechanism of internalization.

Figure 26:
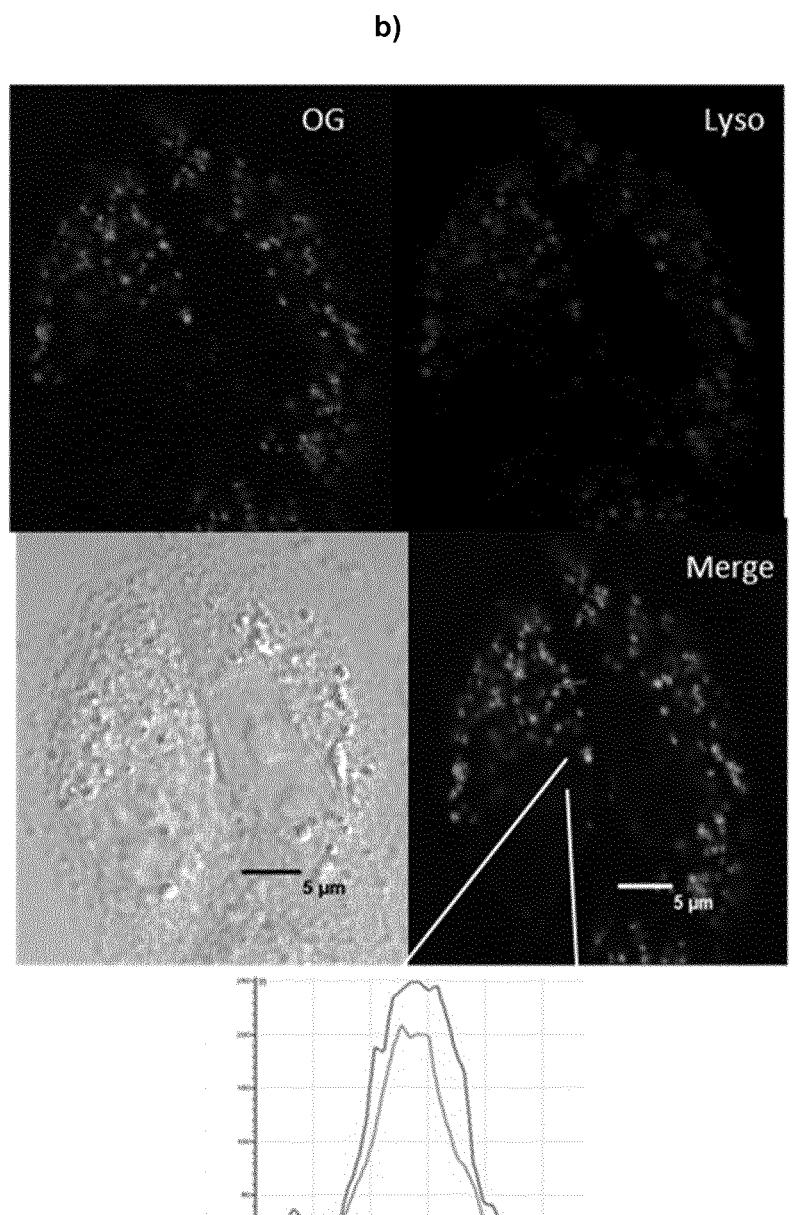

Flow cytometry (cell uptake and binding) together with live-cell confocal microscopy analysis (subcellular fate and pathway) in SHSY5Y human derived neuroblastoma cell line, were used to study cellular trafficking of the OG-labeled star-shaped polymers (FIG. 26). Flow cytometry experiments were carried out at different temperatures, 37° C. (to measure the total uptake) and 4° C. (to measure cell binding) in order to determine the presence of energy dependent or non-dependent internalization mechanisms, such as endocytosis or diffusion, respectively. It is worth mentioning that all experiments were done in presence of the cathepsin B inhibitor CA-047 in order to avoid the degradation of the polyglutamic acid chains along the incubation periods.

Live-cell confocal imaging allows visualizing trafficking between multiple compartments within individual living cells over time, avoiding any possible artifacts derived from fixation protocols. Results from both techniques clearly showed an energy-dependent mechanism of internalization due to the absence of uptake at 4° C. as observed by flow cytometry. This was further confirmed with the confocal microscopy studies at 2 hours post-treatment with an OG labeled polymer in SHSY5Y cells following a pulse-chase experiment, where co-localization in the lysosomes was observed upon the use of lysosomal marker Lysotracker Red (FIG. 26b).

Figure 27:
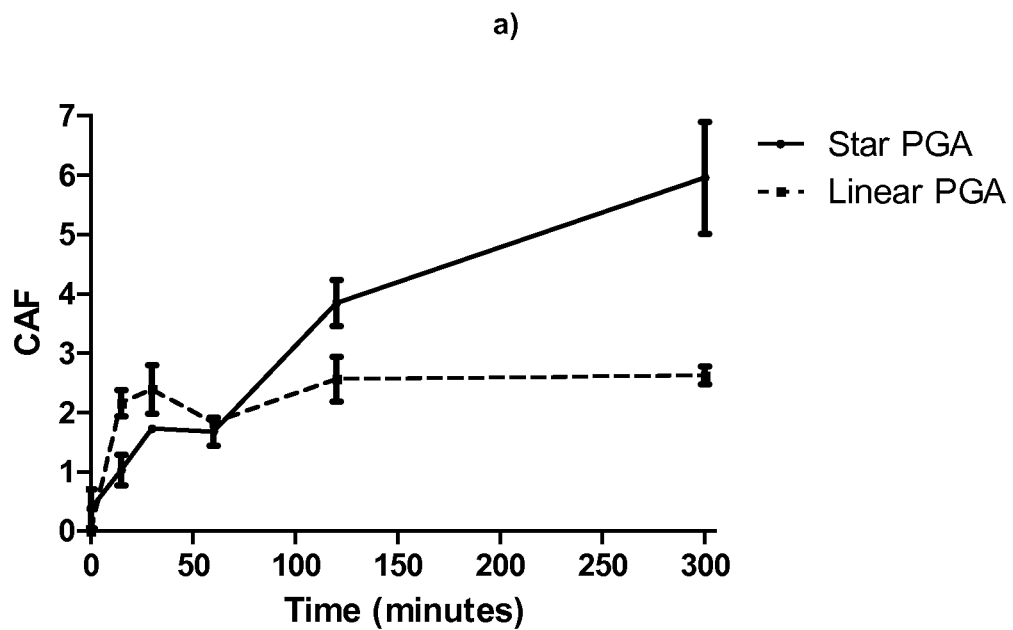
FIG. 27. Uptake study of St-PGA ((compounds formula (I)) in comparison with linear PGA of similar MW (around 250 GAU). a) CAF of both polymers over time. b) CAF of both polymers at 5 hour time point showing significant differences when statistics was performed using one-way ANOVA. p*<0.05. c) % of positive (+) cells to Oregon Green (OG) fluorescence, comparison of both polymers at 5 hour time point showing as expected statistical differences. p*<0.05. d) % of positive cells representation comparing both polymers together with the control used (cell autofluorescence).

Interestingly, the St-PGA-OG showed a significant increase in cell uptake at 5 hours when compared with linear-PGA-OG conjugate of similar MW (FIG. 27). This might be attributed to the inherent properties assigned to the star-shaped polymers. As general basis, star polymers have a more compact structure, presumably with globular shape, and have large surface areas, increased concentrations of functional end groups for polymers with equal molecular weight, and unique rheological properties which make them optimal platforms for drug delivery and imaging among other biological applications.

6.4. Biodistribution and Pharmacokinetics (PK).

To further validate the synthesized nanocarriers, in vivo biodistribution as well as pharmacokinetic profiles (PK) were obtained by radioactivity measurements. For that purpose, a gamma emitting radionuclides $^{111}$In was introduced into the star-shaped PGAs through complexation chemistry as previously explained. In order to accomplish a stable complexation of the metal radioisotope, the incorporation of bifunctional chelating agents into the polymer backbone is required. The most commonly used chelating agents for $^{111}$In are based on polyamine carboxylic acids such as diethylene triamine pentaacetic acid (DTPA), 1,4,7,10-tetraazacyclododecane-1,4,7,10-tetraacetic acid (DOTA), or 1,4,7-triazacyclododecane-1,4,7-tetraacetic acid (NOTA). For the biodistribution of radiolabeled PGA based architectures, DOTA derivative chelating agent with a free amine group suitable for conjugation ($DO_3A-NH_2$) was selected. It is well-known that, $DO_3A-NH_2$ forms stable complexes with several $M^{2+}$ and $M^{3+}$ ions such as $^{68}$Ga or $^{111}$In. Therefore, 20% mol GAU of $DO_3A$-tBu-$NH_2$ was effectively conjugated via amide bond to a St-PGA$_{110}$ (D 1.23).

Figure 28:
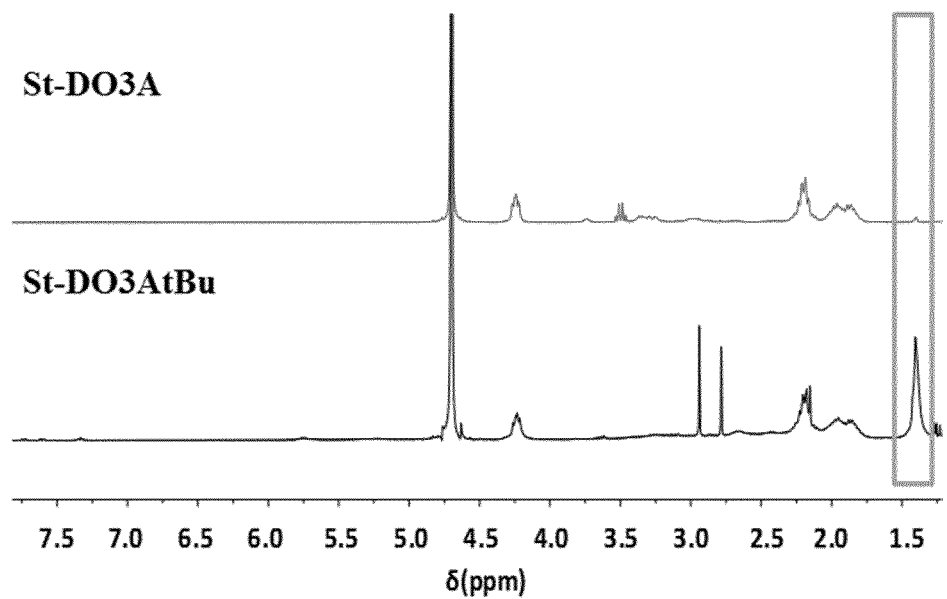
FIG. 28. $^1$H-NMR spectra ($D_2O$) of St-DO3A-tBu and St-DO3A (conjugates of compounds of formula (I)).
Figure 29:
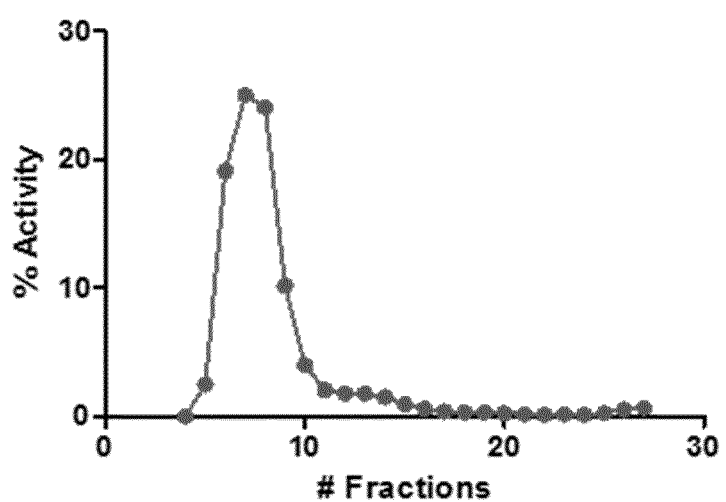
FIG. 29. % Activity measured after $^{111}$In labeling and purification by SEC of St-DO3A (compound of formula (I)).

Conjugation efficiency was almost quantitative (since 10% mol GAU was pursued) with a reasonable mass yield of 75%. The percentage of modification was calculated according to $^1$H-NMR analysis by comparing the corresponding integral of the CH alpha of PGA (4.24 ppm) with the 27 protons of the tBu groups at 1.40 ppm (FIG. 28). The tBu groups were then easily deprotected using the mixture $CH_2Cl_2$/TFA (3/2, v/v). Finally, the St-PGA-$DO_3A$ polymer was labelled with $^{111}$In as described previously. Radio-chemical yields were ≥85% for St-PGA-$DO_3A$-$^{111}$In in all synthesis (as shown in FIG. 29).

Animal experiments to test the biodistribution and PK profile were then carried out with i.v. injected doses between 37 KBq and 2.5 MBq of $^{111}$In-labelled polymers (1-20 μg/g body weight) and monitored up to 24 hours (4-5 mice were sacrificed per time point 0.5, 1, 2, 4, 8 and 24 hours). Blood and organs were extracted and radioactivity was measured ex vivo in the gamma counter.

Figure 30:
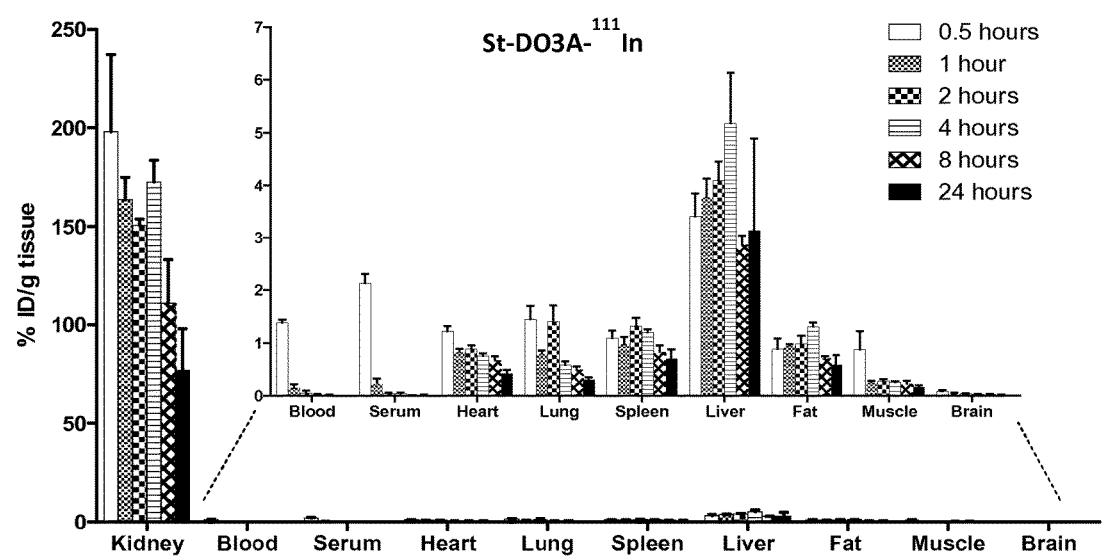
FIG. 30. St-$DO_3A$-$^{111}$In biodistribution. Data expressed as normalized % ID per gram of tissue at different time points.

According to the results obtained from the biodistribution, where the higher percentage of injected dose (ID) corresponded to the kidneys, it can be concluded that these new polypeptide architectures follow renal excretion profiles with no specific accumulation in any organ (FIG. 30).

Figure 31:
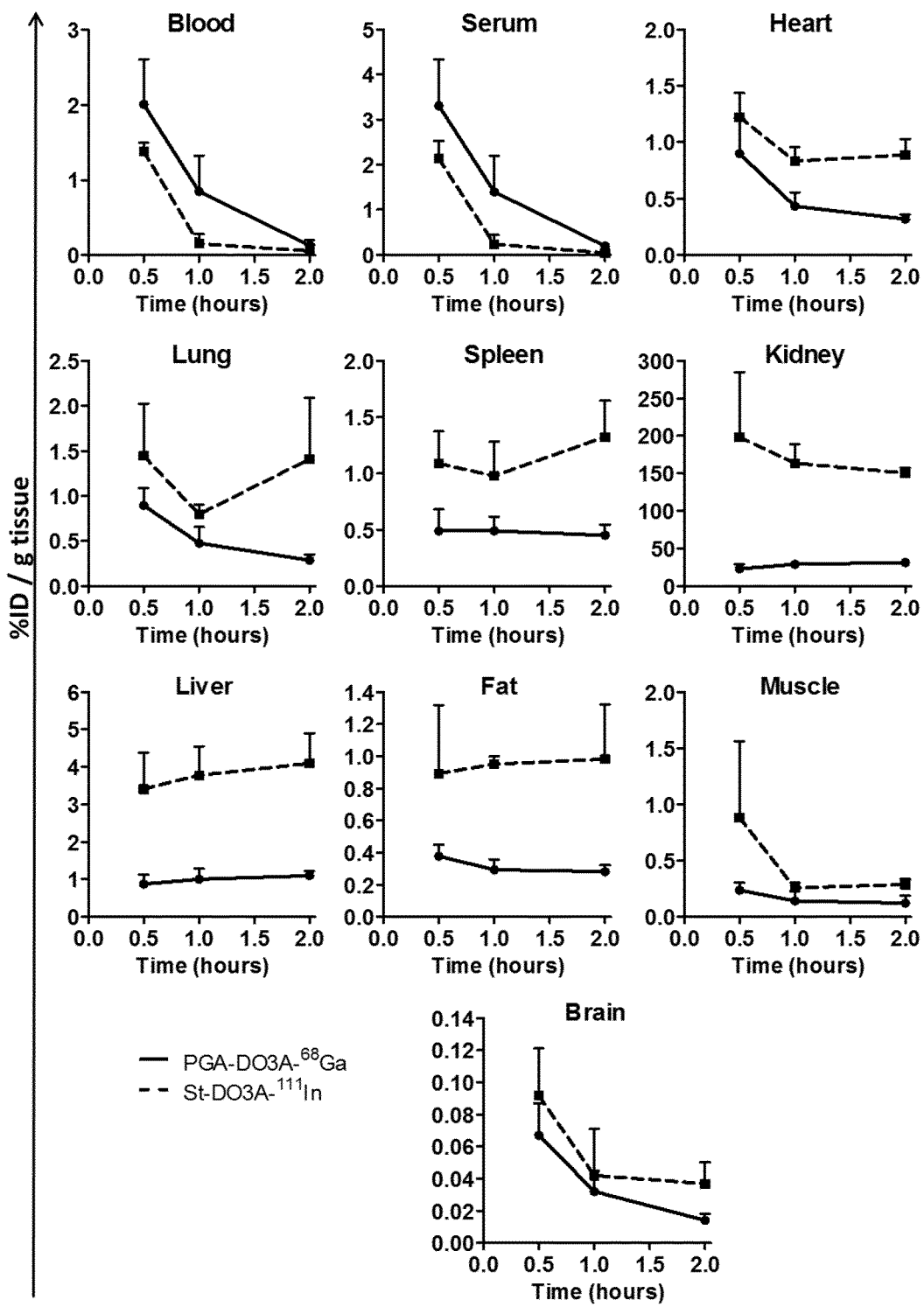
FIG. 31. Normalized data of radioactivity signal of each organ respect the injected dose (ID) per gram of tissue, of St-PGA (compound of formula (I) compared with it linear counterpart of similar MW.

The biodistribution profile obtained for St-PGA was then compared with the one obtained for its linear counterpart of similar MW (100 GAU, D: 1.20). The biodistribution of linear PGA was previously performed using $^{68}$Ga radioisotope, therefore, only short times (up to 3 hours) could be recorded due to radionuclide decay (about 68 min for $^{68}$Ga). If short time points (0.5 h, 1 h and 2 h) of the % ID/g tissue of PGA-$DO_3A$-$^{68}$Ga and St-$DO_3A$-$^{111}$In are compared, a general greater accumulation in all the organs of star shaped polymer is observed, in comparison with the one found in the linear PGA construct as shown in FIG. 31.

Although the plasmatic profiles are similar for both compounds, differences can be drawn when we compared the PK parameters obtained for PGA-DO$_3$A-$^{68}$Ga with St-PGA-DO$_3$A-$^{111}$In. The linear polymer was not detected after 4 hours post administration. Their biological or terminal half-life estimated resulted to be 13 times higher for the star polymer, this fact could be in part attributed to the use of different radionuclides for the study. The use of $^{111}$In allowed to study and estimate the PK parameters of the stars providing results more reliable due to the higher semidesintegration period for $^{111}$In (2.1 days) compared to $^{68}$Ga (68 min).

TABLE 8

Main St-PGA-[$^{111}$In]-DO3A and PGA-[$^{68}$Ga]-DO3A pharmacokinetic parameters estimated by a 2-compartment model following the equation $C(t) = Axe^{(-ALPHAxt)} + Bxe^{(-BETAxt)}$. Values represent Mean ± SD.

| Parameter | St-PGA[$^{111}$In]-DO3A- | PGA-[$^{68}$Ga]-DO3A- |
|---|---|---|
| A (% ID/mL) | 22.33 ± 5.13 | 35.00 ± 12.88 |
| B (% ID/mL) | 0.04 ± 0.01 | 4.35 ± 2.78 |
| ALPHA (h$^{-1}$) | 4.73 ± 0.42 | 7.28 ± 2.56 |
| BETA (h$^{-1}$) | 0.06 ± 0.04 | 1.18 ± 0.59 |
| AUC (% ID · h/mL) | 5.45 ± 0.76 | 8.50 ± 0.67 |
| t$_{1/2}$ ALPHA (h) | 0.15 ± 0.01 | 0.10 ± 0.03 |
| t$_{1/2}$ BETA (h) | 12.05 ± 7.96 | 0.59 ± 0.29 |
| Cl (mL/h) | 18.35 ± 2.55 | 11.77 ± 0.93 |
| Vss (mL) | 46.34 ± 44.44 | 5.25 ± 2.52 |

In the case of the two compartment model a number of volume terms can be defined. V$_{ss}$ is the appropriate volume of distribution (Vd) when plasma concentrations are measured in steady state conditions. This V$_{ss}$ value is about 9 times higher for the star polymer compared to the linear one, meaning a greater distribution of the carrier. The Clearance value (Cl) from the central compartment is slightly higher also in the star-shaped polymer (18.35 vs 11.77 mL/h for linear PGA). The renal clearance value of inulin (a model compound that is excreted only by glomerular filtration and is not subject to tubular secretion or re-absorption) has being established to be around 20 mL/h by in FVB mice. This value is really close to the value obtained for the star polymer. Thus it could be claimed that the polymer is cleared out only by glomerular filtration. In the case of linear PGA, the value is slightly smaller. This could be explained by the binding of the compound to plasmatic proteins, reducing the glomerular filtration, or if the linear polymer could be reabsorbed in the tubules.

Example 7: Validation of Compounds of Formula (III) as Carriers 7.1. Cell Viability.

Figure 32:
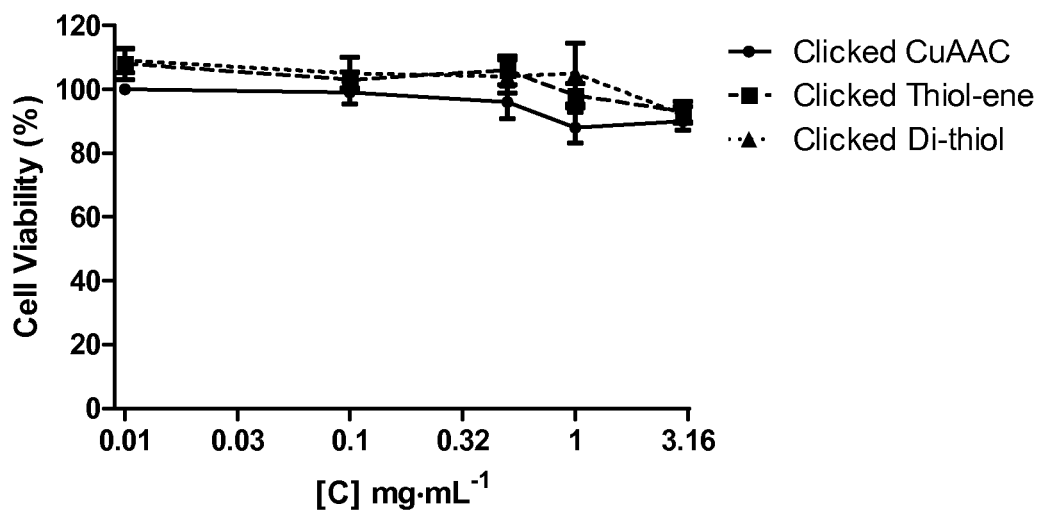
FIG. 32. Cell viability assay of 3 different St-Click architectures (compounds of formula (III)) against SHSY5Y cell line up to 3 mg·mL$^{-1}$, 72 hours of treatments (n>3, mean±SEM).

Cell viability against SHSY5Y cell line of the three chemically different clicked architectures was studied. All of them resulted non-toxic up to 3 mg·mL$^{-1}$ when tested at 72 hours of incubation following an MTS protocol for cell viability determination. Results are shown in FIG. 32.

7.2. Cellular Uptake.

Flow cytometry (cell uptake and binding) together with live-cell confocal microscopy analysis (subcellular fate and pathway) in SHSY5Y human derived neuroblastoma cell line, were used to study cellular trafficking of the OG-labeled clicked stars (compounds of formula III). Uptake experiments were carried out at different temperatures, 37° C. (total uptake) and 4° C. (binding) in order to determine the presence of energy dependent or non-dependent internalization mechanisms, such as endocytosis or diffusion, respectively. It is worth mentioning that all experiments were done in the presence of cathepsin B inhibitor CA-047 in order to avoid possible degradation of PGA chains along the incubation periods. Results were represented by means of cell associated fluorescence (CAF) over incubation time. CAF represents the percentage of positive cells multiplied by fluorescence intensity and divided by 100, always removing CAF of control cells (without treatments) in order to avoid any artifacts from autofluorescence phenomena.

Figure 33:
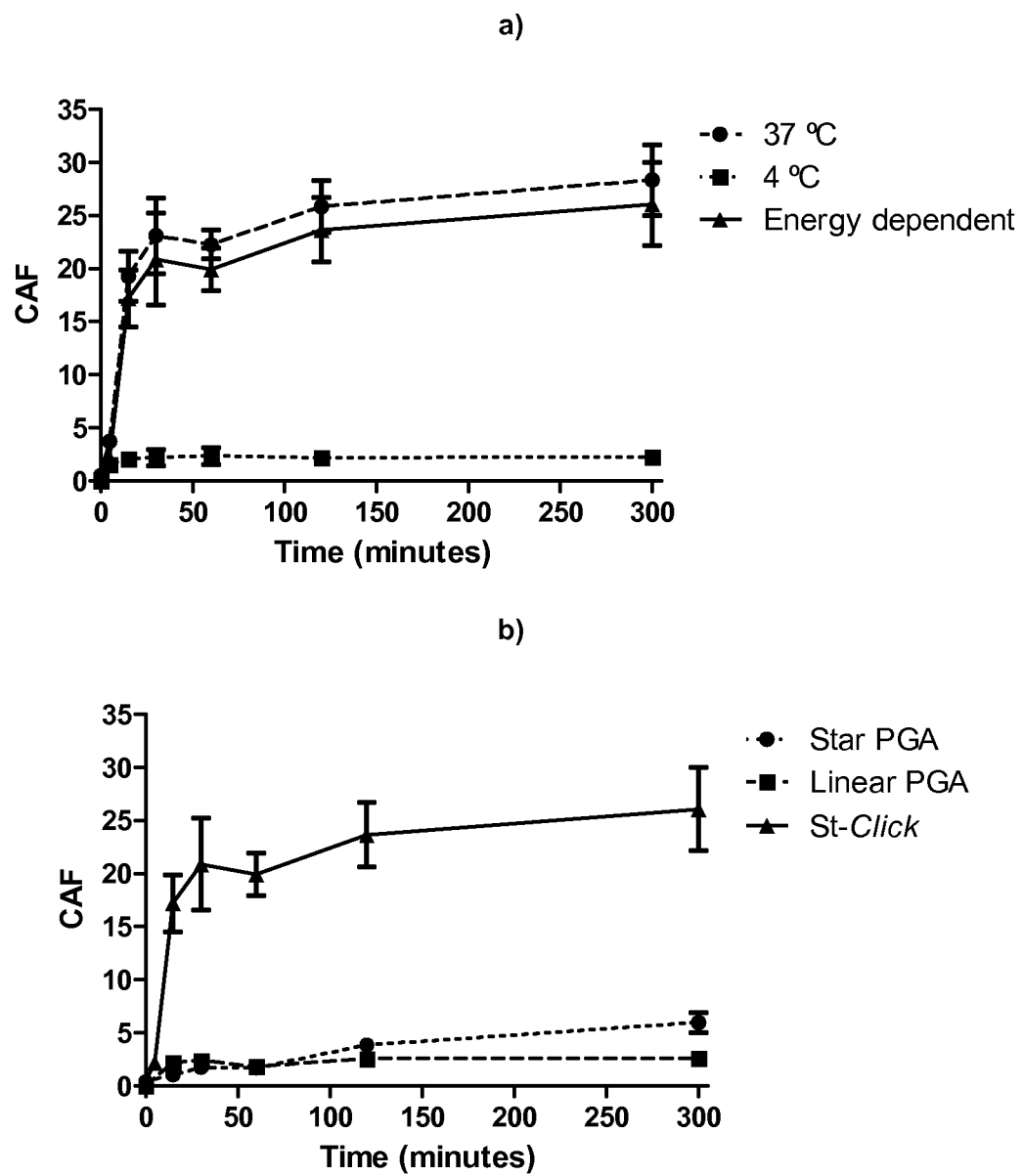
FIG. 33. a) Uptake kinetics against SHSY5Y cell line of St-Click-OG-labeled (compound of formula (III)) polymer at different time points and different temperatures (4° C. for binding, 37° C. for total uptake). b) CAF representing the energy-dependent fraction of uptake, comparing the three architectures over time. n>3, mean±SEM.
Figure 34:
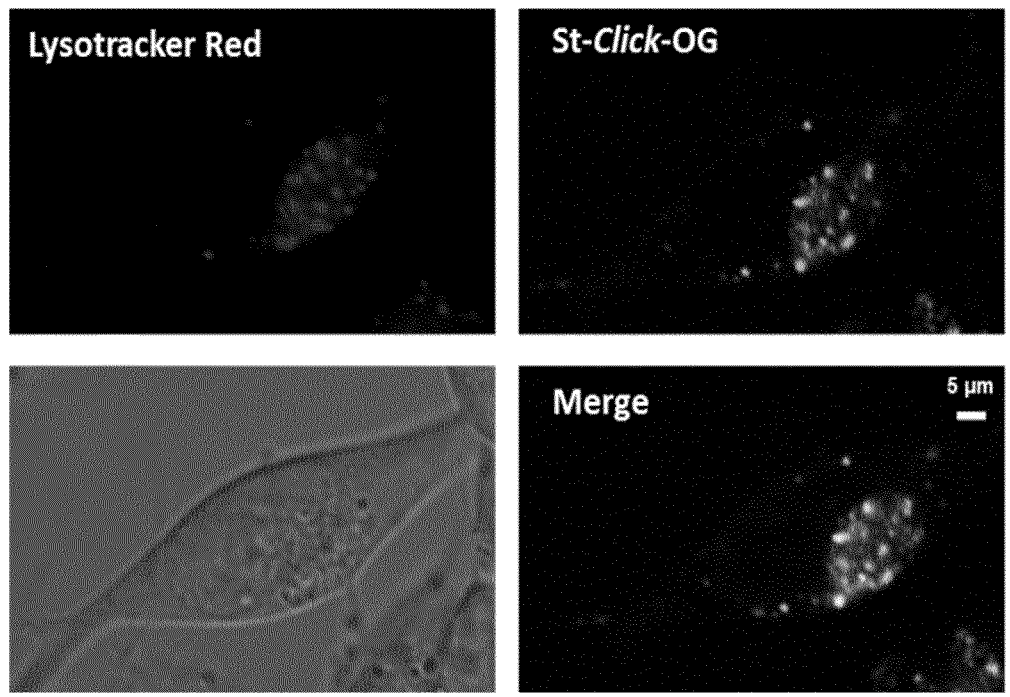
FIG. 34. Confocal image of the uptake at 2 hours post-treatment of OG-labeled St-Click compound of formula (III)) in SHSY5Y cell line following a pulse-chase experiment. Co-localization with Lysotracker Red was observed.

Results shown in FIG. 33 demonstrate the energy-dependent mechanisms of internalization (endocytosis) in due to absence of uptake at 4° C. as observed by flow cytometry. As it could be expected, this globular shaped structure was fast internalized, showing around 95% of positive cells already at 15 minutes (FIG. 33a). Furthermore, when this construct was compared with the linear PGA and non-clicked star PGA, a significant increase in cell-associated fluorescence (CAF) was observed (FIG. 33b). Not only such compound goes through a faster uptake (according to both CAF and % positive cells) but also, the amount of construct internalized is significantly greater when compared with the other 2 systems. Furthermore, co-localization with the lysosomal marker Lysotracker Red was found in confocal microscopy images (FIG. 34).

Example 8. Validation of Compounds of Formula (III) as Carrier to Cross the Blood Brain Barrier (BBB)

8.1. Synthetic Strategy and Characterization.

Figure 35:
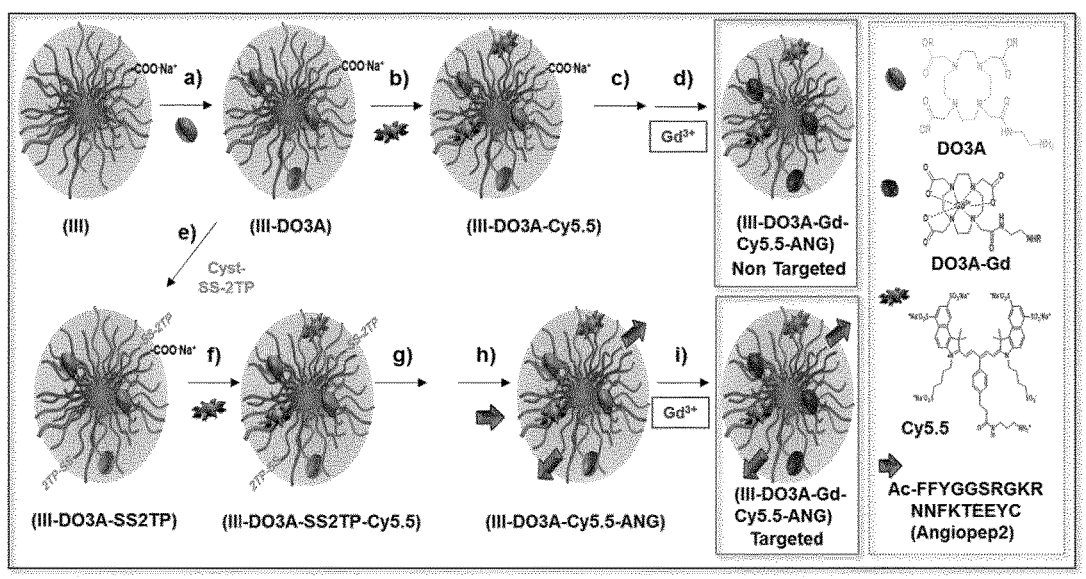
FIG. 35. Schematic representation of the synthetic route followed for surface modification of the covalently captured star-shaped PGAs (compounds of formula (III)) to reach the dual probes. a) 1) DMTMM.Cl, 2) DO3AtBu-$NH_2$ in dd$H_2O$, r.t. 24 h. b) and f) 1) DMTMM.Cl, 2) Cy5.5 (6S-IDCC) in dd$H_2O$, r.t. 24 h. c) and g) TFA:TIPS:dd$H_2O$ (95:2.5:2.5), r.t. 3 h. d) and i) GdCl$^{3+}$ in PBS 0.1 M 7.4, r.t. 5 h. e) 1) DMTMM.Cl, 2) cysteamine-SS2TP in dd$H_2O$, r.t. 24 h. h) ANG in HEPES buffer 7.4, r.t. 16 h. *Yellow disc: DO3A, *Purple disc: DO3A-Gd3+*Blue star: Cy5.5, *Green arrow: Angiopep-2

In order to validate the systems as adequate carriers for intravenous administration, biodistribution experiments were done. The clicked stars were labeled with DO3A-Gd$^{3+}$ for MRI techniques and Cy5.5 for fluorescence optical imaging techniques. Furthermore, in order to ratify the versatility of the systems to be used as carriers through the BBB, the targeting ligand ANGIOPEP-2 (ANG-2) currently in Phase II clinical trials was linked to the polymers. Synthetic route of these conjugates can be seen in FIG. 35.

Briefly, DMTMM-Cl was employed in order to activate the carboxylic acids to allow the introduction of DO3AtBu-NH$_2$ in the first place, followed by Cy5.5 in the synthesis of the non-targeted system. DO3A modified units were quantified by $^1$H-NMR. On the other hand, Cy5.5 content estimation was carried out by fluorescence (prior calibration curve of Cy5.5 dye in PBS buffer was obtained.

For the non-targeted construct, tBu protecting groups from DO3A were easily removed at this point, using the mixture TFA:TIPS:H$_2$O (95:2.5:2.5). In the case of the targeted polymer, cysteamine-2TP units were introduced again by post-polymerization modification in aqueous media prior to the introduction of Cy5.5. Quantification was determined as 10 mol % of GAU by $^1$H-NMR. Then, the tBu protecting groups from DO3A were removed, and ANG was conjugated following previous strategies by means of disulfide bonding. Finally, Gd$^{3+}$ was complexed to DO3A bearing constructs using a 1:1 eq. (DO3A:GdCl$_3$) ratio. The reaction took place in PBS 0.1 M at pH 8 (GdCl$_3$ precipitation was observed at lower pHs) and monitored by titration using 4-(2-pyridylazo)resorcinol. This titrating agent turns from yellow to orange in the presence of free Gd$^{3+}$. After 5 hours reaction time, no free Gd$^{3+}$ was detected. The reaction was purified by dialysis and absence of free $Gd^{3+}$ was again tested. Conjugates physico-chemical characteristics are summarized in Table 9.

TABLE 9

Conjugate physico-chemical characteristics for in vivo biodistribution by fluorescence.

| Compound | mol % GAU wt % DO3A | wt % Gd | mol % GAU/ wt % Cy5.5 | mol % GAU/ wt % ANG |
|---|---|---|---|---|
| St-Click-DO3A-Gd-Cy5.5 | 10.0 mol % 20.3 wt % | 12.0 | 0.5 mol % 3.1 wt % | — |
| St-Click-DO3A-Gd-Cy5.5-ANG | 10 mol % 17.6 wt % | 10.4 | 0.5 mol % 2.7 wt % | 1.5 mol % 13.8 wt % |

Figure 36:
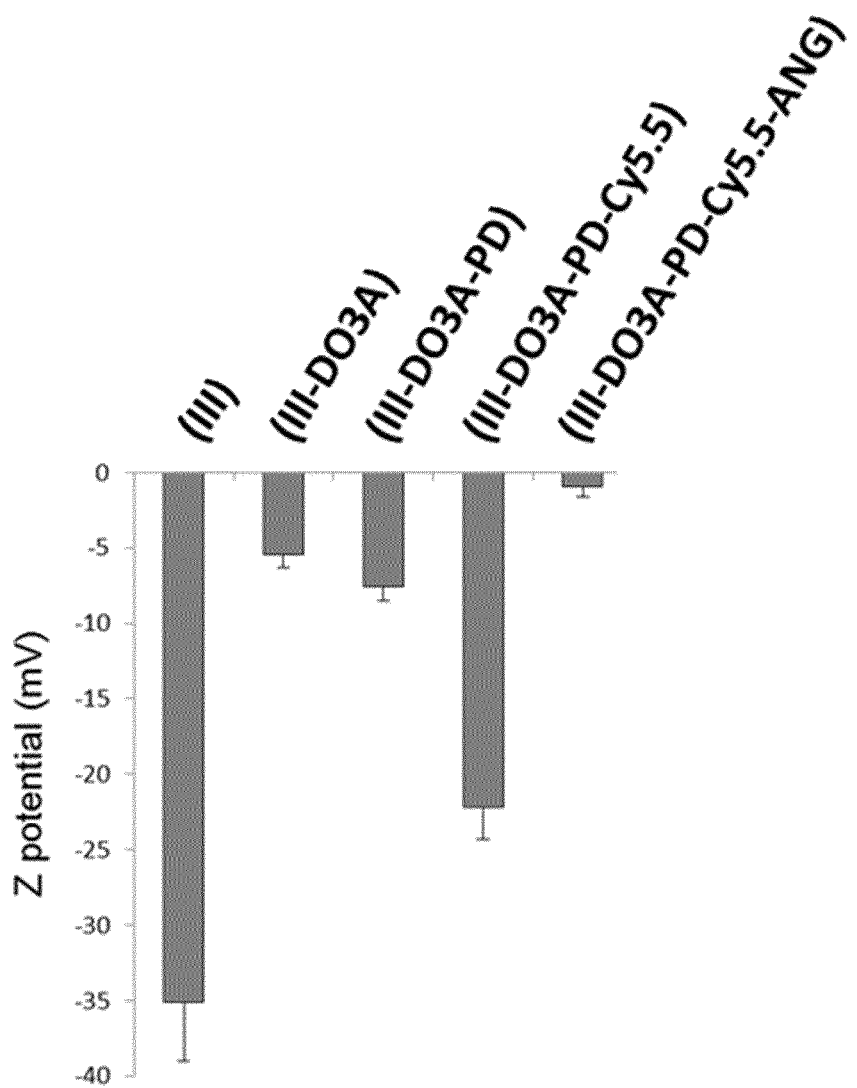
FIG. 36. Z-potential obtained at 20° C. from clicked structures (compounds of formula (III)) at 1 mg·mL$^{-1}$ in dd$H_2O$, before and after the subsequent surface modifications.

The Z-potential of the clicked architectures before, and after surface modifications was recorded in $ddH_2O$ at 20° C. and the results are depicted in FIG. 36. As it can be observed, surface modifications with DO3A-tBu and cysteamine-2TP, significantly decrease the negative Z-potential obtained for the clicked structure with all the carboxylic groups unmodified and presumably exposed at the surface.

The introduction of the negatively charged Cy5.5 within the structure resulted in an increase on Z-potential obtained. Finally, when ANG-2 peptidic sequences where conjugated, Z-potential dramatically decrease to almost neutral, probably due to a shielding effect provided by the 19 aa sequences.

Figure 37:
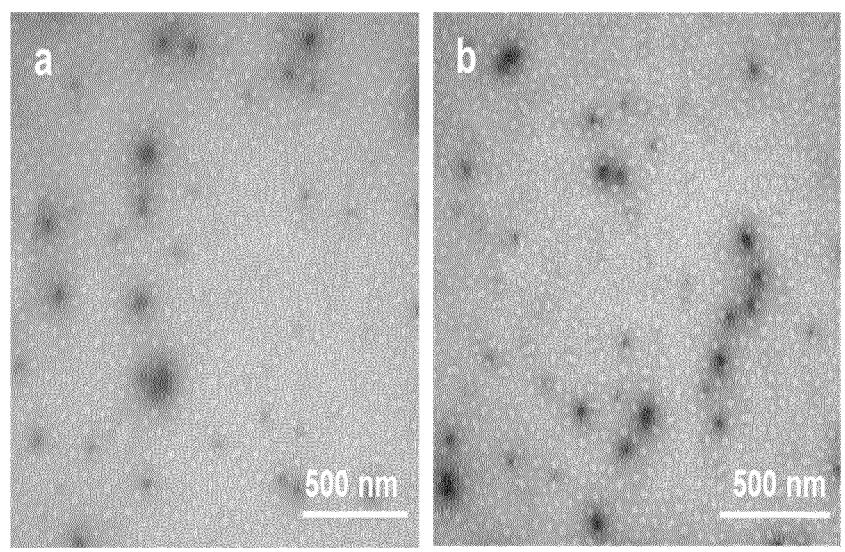
FIG. 37. TEM micrographs of a) St-Click-DO3A-Gd-Cy5.5, and b) St-Click-DO3A-Gd-Cy5.5-ANG (compounds of formula (III))

Furthermore, size of the systems was estimated by TEM to be in the range of 70-100 nm diameter (FIG. 37)

8.2. In Vivo Evaluation of Compounds of Formula (III) as Carriers to Cross the BBB.

Figure 38:
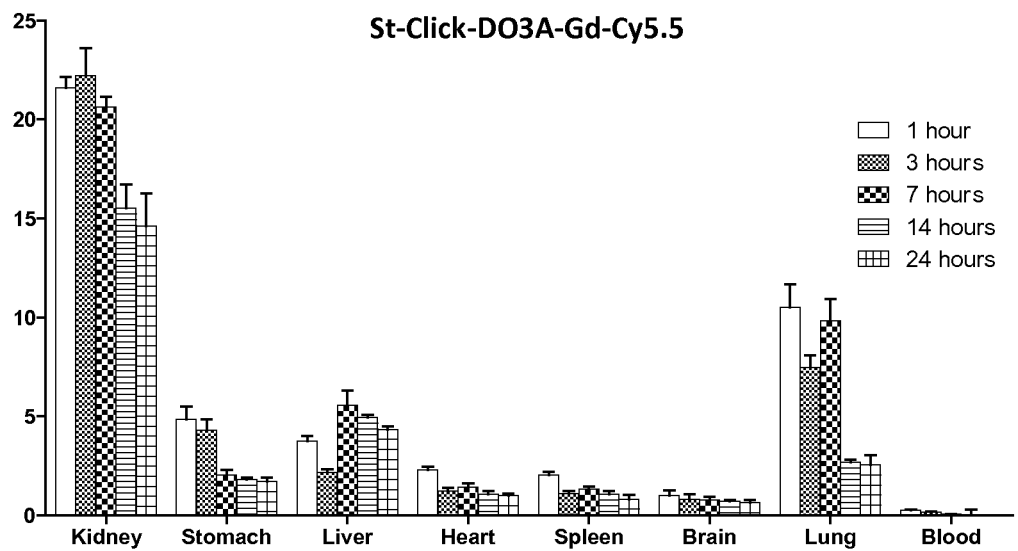
FIG. 38. % ID normalized by pixel area of non-targeted (a) and targeted (b) Cy5.5 labeled clicked architectures (compounds of formula (III)).
Figure 38:
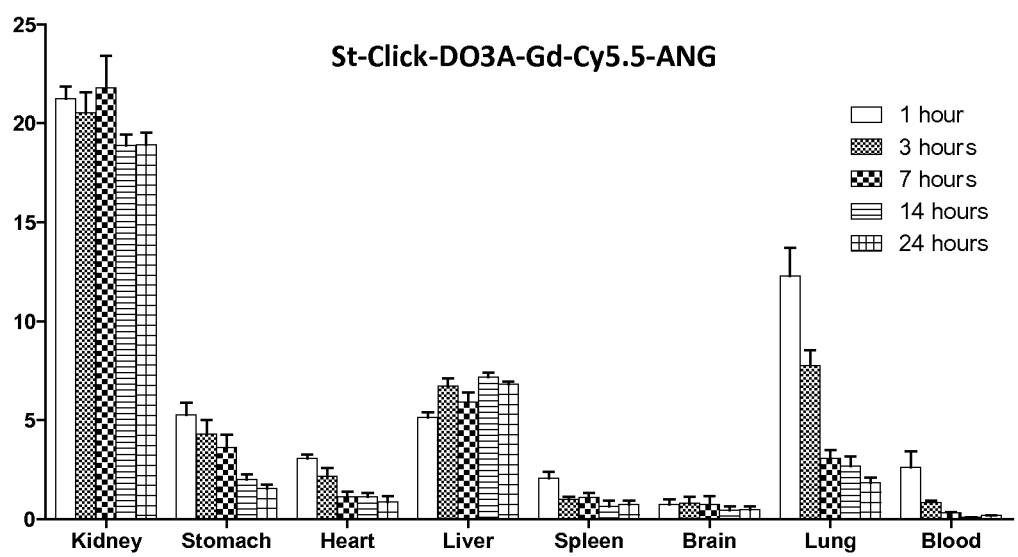

Biodistribution experiments were carried out using $C_{57}Bl/6$ mice and fluorescence techniques taking profit from Cy5.5 dye on the polymeric carriers. Targeted and non-targeted architectures were administered i.v. through the tail vein to isofluorane anesthetized mice, at a dose of 4.15 $mg \cdot Kg^{-1}$ Cy5.5 eq. Two animals were then sacrificed at different time points (1, 3, 7, 14 and 24 hours). Prior to sacrificed, mice were first anesthetized with a lethal anesthesia cocktail, blood was extracted from the cava vein, and perfusion with saline was carried out in order to accurately determine the amount of compound in the brain. Then, organs were extracted and their fluorescence was measured using the red filter in MAESTRO™. For fluorescence quantification, normalized data was obtained by taking always the same pixel area for all organs expressed as average signal ($counts \cdot s^{-1}$). A calibration curve of the compounds in the same MAESTRO™ was carried out in order to estimate the fluorescence corresponding to the injected dose. Biodistribution data obtained from non-targeted and targeted polymer is depicted in FIGS. 38 and 39.

Figure 39:
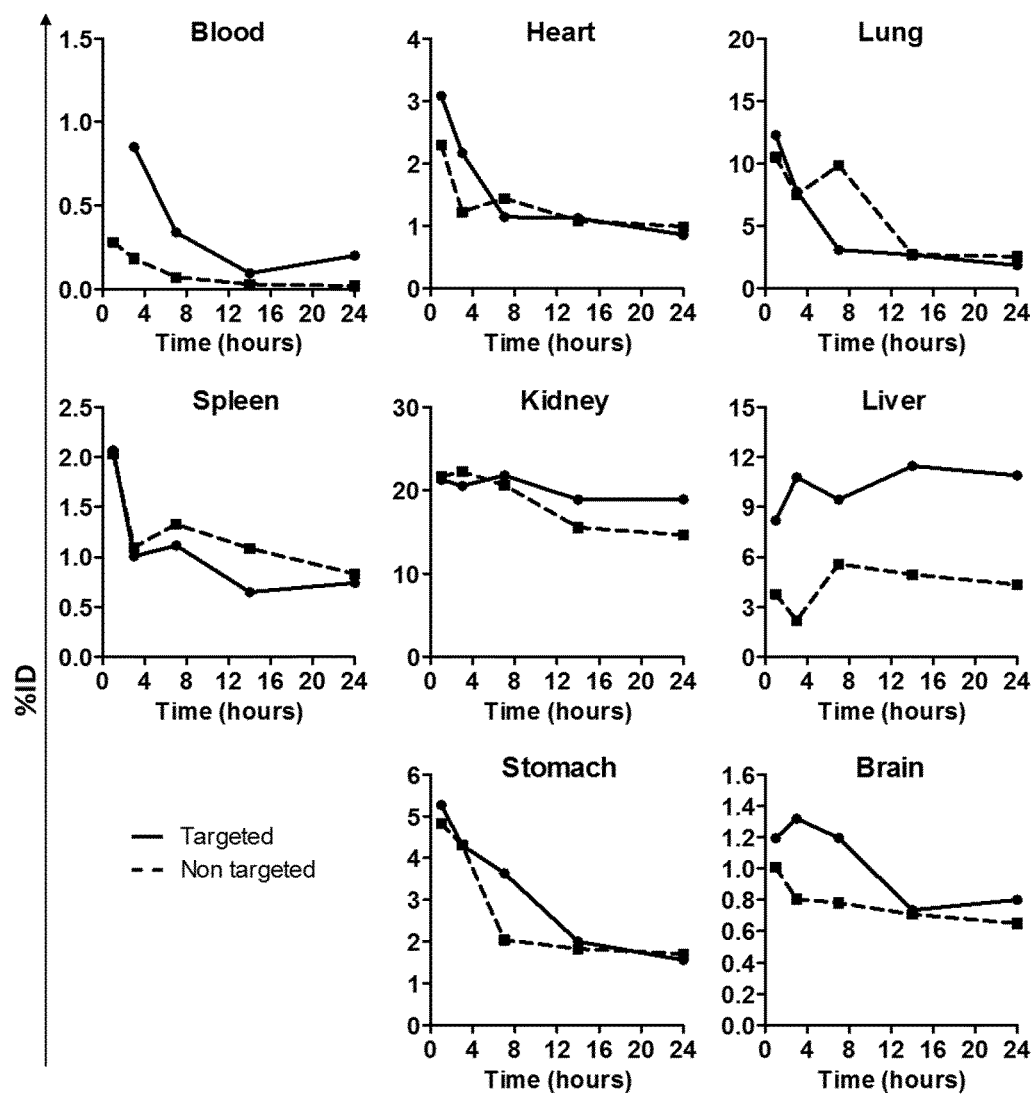
FIG. 39. Biodistribution by optical imaging at different time points of targeted and non-targeted clicked architectures (compounds of formula (III)). Time course experiment. Error bars are not included for clarity reasons.

When both compounds were compared, no major differences in biodistribution were encountered as it can be observed in FIG. 39. Renal excretion profiles could be observed in both cases. However, the targeted compound was found to accumulate in a higher extend in organs such as liver and kidney. Notably, when the biodistribution data from these bigger architectures was compared with that from the non-clicked stars, a greater accumulation in the lungs at early time points was observed. This fact was in good agreement with the nature of the architectures used, since sizes above 100 nm tend to accumulate in lungs. Hence, this family of architectures could have a potential use in order to target lung diseases such as lung cancer. Nevertheless, these carriers also demonstrated to be safe as not weight loss in the animals was observed. Besides, lung accumulation was significantly diminished over time, validating them as possible carriers.

Important to note, the ANG bearing compound offered greater brain accumulation at early time points when compared to the non-targeted counterpart. Nonetheless, similar accumulation was found for both compounds at late time points such as 24 hours. Remarkably, the amount found in the brain in both cases was between 1-1.5% ID, which is 20-30 times greater than the one obtained for non-clicked stars (0.05% ID). As mentioned before and according to literature, the normal % ID for those systems which are able to reach the brain is usually between 1-2% ID, with the maximum obtained with 4%.

Example 9. Validation as Carrier to Treat Neurodegenerative Disease 9.1. Synthetic Protocol and Characterization.

We aimed to obtain combination conjugates for systemic administration with synergistic effect using the neuroprotective-neurorescuer propargyl moieties and the neuro-anti-inflammatory curcuminoids, looking for a new therapeutic strategy in AD.

Briefly, in a two-necked round bottom flask, fitted with a stirrer bar and two septums, the corresponding star polymer was dissolved in 10 mL of anh. DMF under nitrogen atmosphere. After that, 1.5 eq. of $DMTMM \cdot BF_4$ of the desired percentage of GAU modification was added in 5 mL more of anh. DMF. Reaction was left to proceed for 10 minutes. Then, 1.5 eq. of the desired percentage of GAU modification of bisdemethoxycurcumin (BDMC) were added to the reaction mixture, followed by a catalytic amount of DMAP. The pH was checked to be around 7. Reaction was then left to proceed for 72 hours. For purification, the mixture was poured into a large excess of diethyl ether. After isolation, the yellowish solid was converted into sodium salt form by careful addition of $NaHCO_3$ 1 M. Then, the aqueous solution was washed with diethyl ether till no yellowish coloration was found in the organic phase. Finally, the product in aqueous phase was purified by dialysis using Vivaspin® MWCO 5000, and freeze-dried. BDMC contain was determined by UV-VIS at 415 using a calibration curve with free BDMC. FDC was estimated by HPLC following the method: eluent A was $ddH_2O$ and eluent B was acetonitrile. Samples were analyzed using the following gradient: from 40% B to 80% B over 20 min using Lichrospher 100 RP 18, 5.0 μm (dimension: length×ID)=125×4.0 mm). BDMC retention time (tr) 5.98 minutes. Experiments were done per triplicate. % of free drug was established by performing a calibration curve with BDMC dissolved in the mixture $ddH_2O$/Acetonitrile (50/50) and injected under the same HPLC conditions.

TABLE 10

Physico-chemical characteristics of BDMC-conjugates through bottom-up approach, conjugates of formula (II) and (III).

| Conjugate | TDC wt % (Abs 415 nm) | FDC wt % of TDC (Abs 415 nm, HPLC) |
|---|---|---|
| St-BDMC | 0.5 | <1 |
| St-BDMC | 1 | <1 |
| St-BDMC | 2.5 | <1 |
| St-EN(2)N3(5)-BDMC | 1.25 | <1 |
| St-Click-BDMC | 2.00 | <1 |
| St-Click-BDMC | 4.00 | <1 |

*TDC: total drug content; FDC: free drug content.

9.2. Cell Viability.

Figure 40:
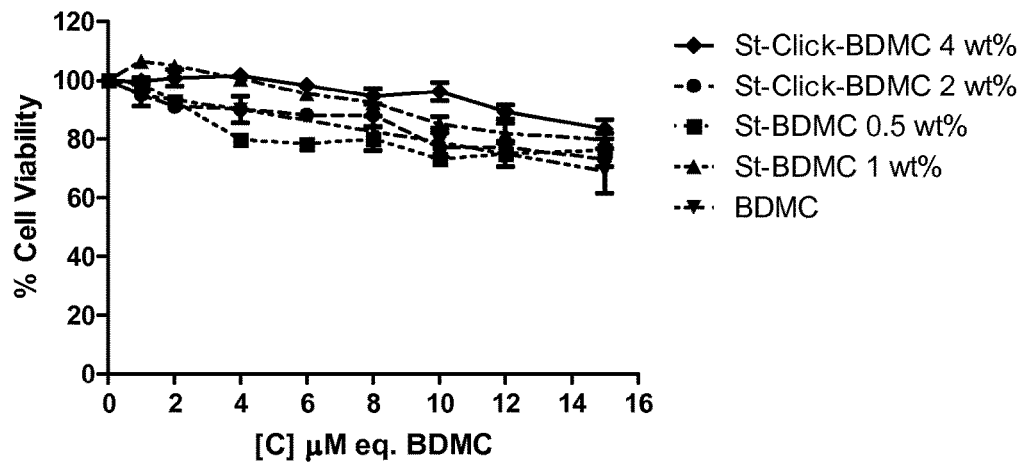
FIG. 40. Cell viability of BDMC derivatives (compounds of formula (I, or III)) against SHSY5Y cell line. 72 hours MTS assay. n>3, mean±SEM.

Firstly, cytotoxicity of BDMC bearing polymers was explored up to 15 µM drug-eq. According to previous studies found in literature, a curcuminoid concentration range of 0.1-1 µM should be enough to induce a therapeutic benefit by diminishing oxidative stress. Moreover, the IC50 value for Aβ aggregation and lipid peroxidation of curcuminoids is also found in that concentration rage, indicating that such a dose should be enough in order to produce antioxidant and anti-inflammatory effects. As it can be observed from FIG. 40, non-significant toxicities up to 10 µM drug-eq. were found. The compound St-Click-BDMC with 4 wt % of BDMC was selected for further investigations (100% cell viability at 10 µM).

9.3. Drug Release Profiles.

Figure 41:
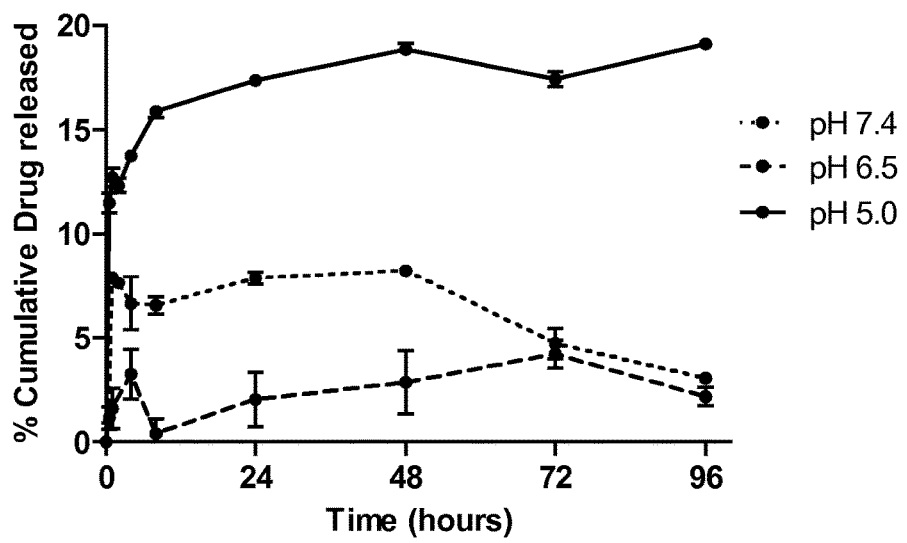
FIG. 41. Drug release profiles at different pH (5.0, 6.5 and 7.4) of St-Click-BDMC (4 wt %), (compound of formula (III)). Time course experiments were done per triplicate. n>3, mean±SEM.

Since a pH degradable linker (ester) was used for the conjugation of BDMC, the kinetics of drug release under hydrolytic conditions was consequently studied. Samples of St-Click-BDMC 4 wt %, (selected from cell viability experiments) were incubated at 37° C. at different pHs including 5.0 (lysosome), 6.5 (endosome) and 7.4 (blood) up to 96 hours. A sustained and controlled drug release profile was obtained after HPLC analysis. About 20% of the conjugated drug was released within 2 days at pH 5.0 whereas pH 6.5 and 7.4 showed a much slower release profile (see FIG. 41).

9.4. Prevention of Fibril Formation In Vitro.

Figure 42:
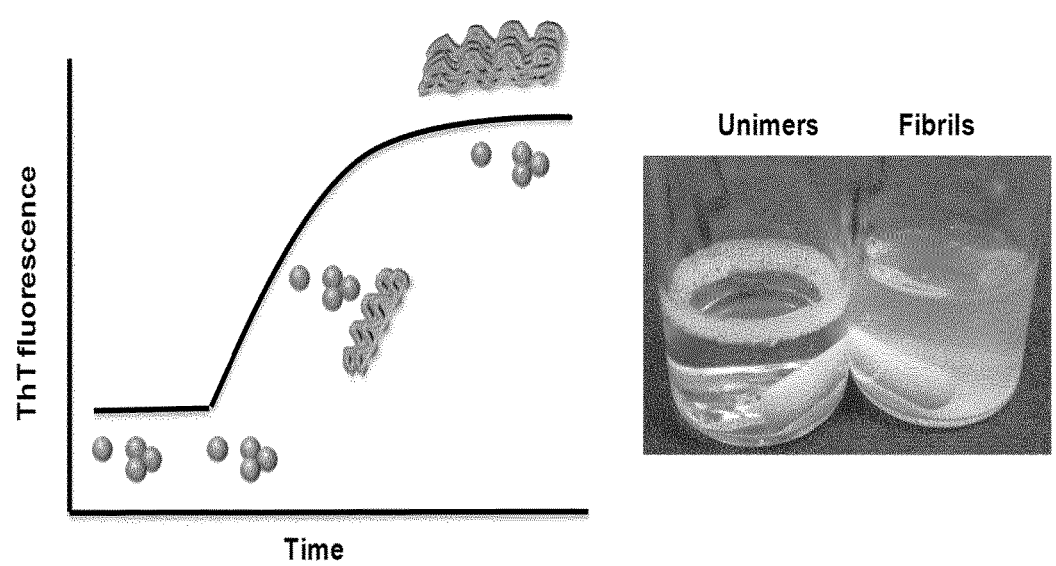
FIG. 42. a) Schematic representation of ThT fluorescence changes upon protein fibrillization. b) Pictures of HEWL unimers and HEWL fibrils upon heating at 60° C. and vigorous stirring during 24 h, pH 2.0.

In order to achieve proof of concept, activity of the compounds was checked in a first attempt using an accepted model based on the use of Hen Egg White Lysozyme (HEWL) for protein amyloid formation. HEWL is a monomeric protein composed of 129 amino acids with helix rich conformation, and it represents one of the best known model proteins to study protein aggregation. It has been demonstrated that under acidic pH this protein undergo amyloid aggregation (FIG. 42). Hence, activity of several BDMC bearing conjugates, as inhibitors of fibril formation was checked by Thioflavin T (ThT) fluorescence measuring, which is in correlation with fibril formation. ThT is a benzothiazole salt used as a dye to visualize and quantify the presence or fibrillization of misfolded protein aggregates, or amyloid, both in vitro and in vivo (i.e. plaques composed of amyloid beta found in the brains of Alzheimer's disease patients). ThT Assay measures changes of fluorescence intensity of ThT upon binding to amyloid fibrils (FIG. 42). The enhanced fluorescence can be observed by fluorescence microscopy or by fluorescent spectroscopy. The spectroscopic assay is normally used to monitor fibrillization over time.

Figure 43:
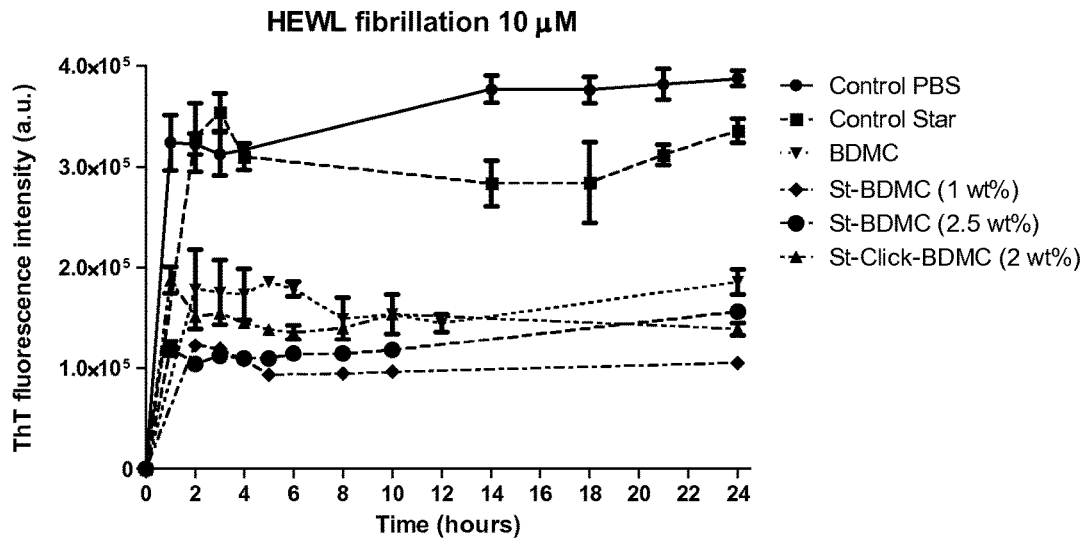
FIG. 43. ThT fluorescence intensity changes upon time in HEWL samples incubated with different BDMC conjugates (compound of formula (I or III)) at a) 10 µM BDMC-eq. and b) 50 µM BDMC-eq. n>3, mean±SEM.
Figure 43:
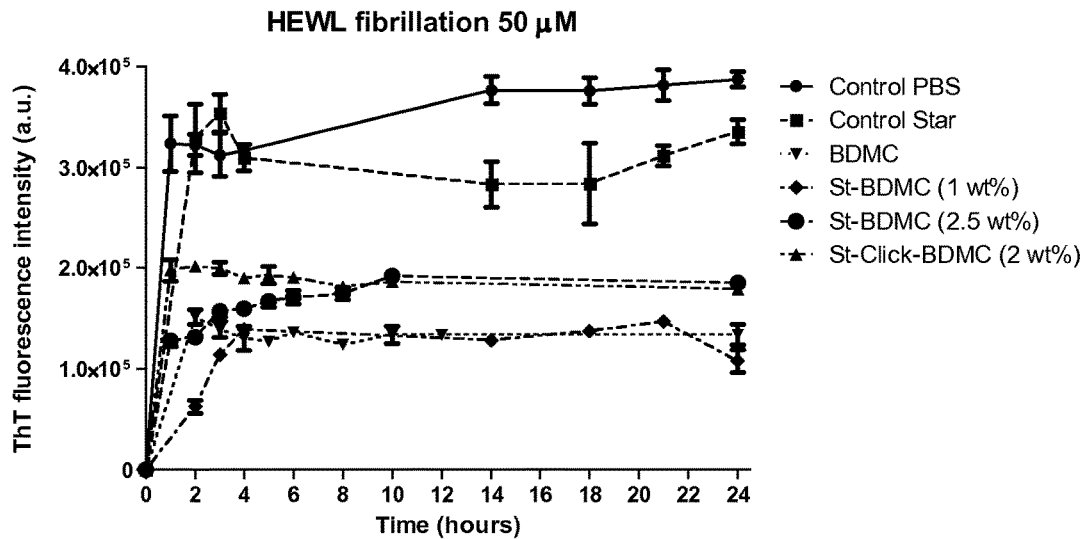
Figure 44:
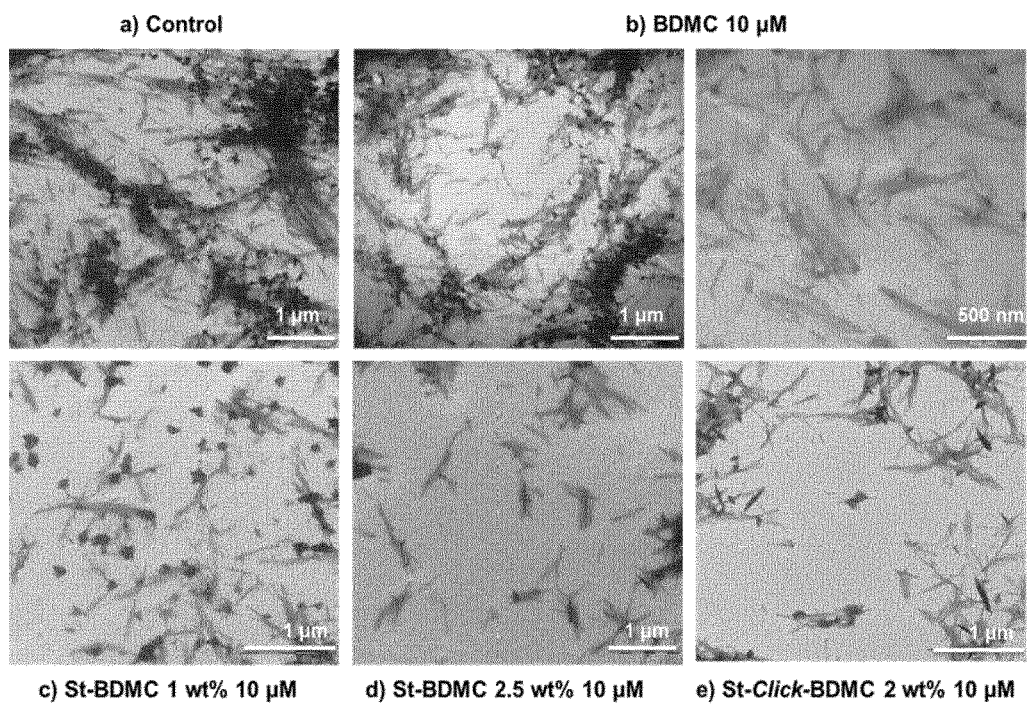
FIG. 44. TEM pictures obtained from HEWL incubated samples within the different BDMC polyglutamate derivatives (compound of formula (I, or III)) at 10 µM BDMC-eq. (c-e) in comparison with a) Control PBS and b) Free BDMC 10 µM.

Then, several BDMC bearing compounds and free BDMC, for comparison, at two different concentrations (10 and 50 Mm BDMC-eq.) were incubated for 24 hours with HEWL (2 mg·mL$^{-1}$ solution) at 60° C. under vigorous magnetic stirring, and at low pH in order to favor amyloid aggregation. PBS solutions and the polymeric carrier were used as positive controls. It is worth mentioning that, no fibrillation was found neither when HEWL was incubated at r.t. nor when no magnetic stirring was used. Aliquots of the fibril samples were taken at different time points and mixed with ThT aliquots for 5 minutes. Finally, fluorescence was measured in a Victor™ Wallace ($\lambda_{exc}$ 450 nm and $A_{em}$ 510 nm) and background fluorescence from curcuminoid subtracted (FIG. 43). By this assay, it could be concluded that the polymer conjugates exhibits a fibril inhibitor behavior slightly better (although no significantly different) than free BDMC. It was also clear that, activity of the conjugates was mainly due to the presence of curcuminoid and not to the PGA chains. The use of higher concentrations (50 µM drug-eq.) did not improve the results obtained when compared with lower concentrations (10 µM drug-eq.). 10 µM BDMC-eq was selected then, as the concentration to move forward. These results were further confirmed by TEM, as it can be observed in FIG. 44.

9.5. Effects of St-Click-BDMC on Aβ Induced Neurotoxicity in Hippocampal Organotypic Cultures.

The neuroprotective effect of the curcuminoid bearing polymeric structure was evaluated in organotypic cultures from entorhinal cortex-hippocampus. In order to study neuroprotection, the experimental design involved pretreatments with the conjugate prior to an Amyloid-β peptide (Aβ$_{1-42}$) triggered injury. This ex vivo model has been previously validated to determine neurotoxicity and constitutes an effective manner to identify the neuroprotective effect of molecules with real therapeutic potential against AD. The organotypic cultures of slices containing both entorhinal cortex and hippocampus are an excellent ex vivo model to monitor the structure and physiology of these regions of the limbic system. They preserve the principal circuits of hippocampus, including its main excitatory input coming from the entorhinal cortex. Besides, they can be maintained for long periods of time, optimal to evaluate pharmacological activity on neurons or glial cells of the different treatments upon time. Hippocampus and entorhinal cortex are among the most affected regions in AD, accumulating a high density of extracellular deposits of Aβ peptide, and are partially responsible of the progressive memory loss and cognitive impairment observed in this neurological disorders.

Figure 45:
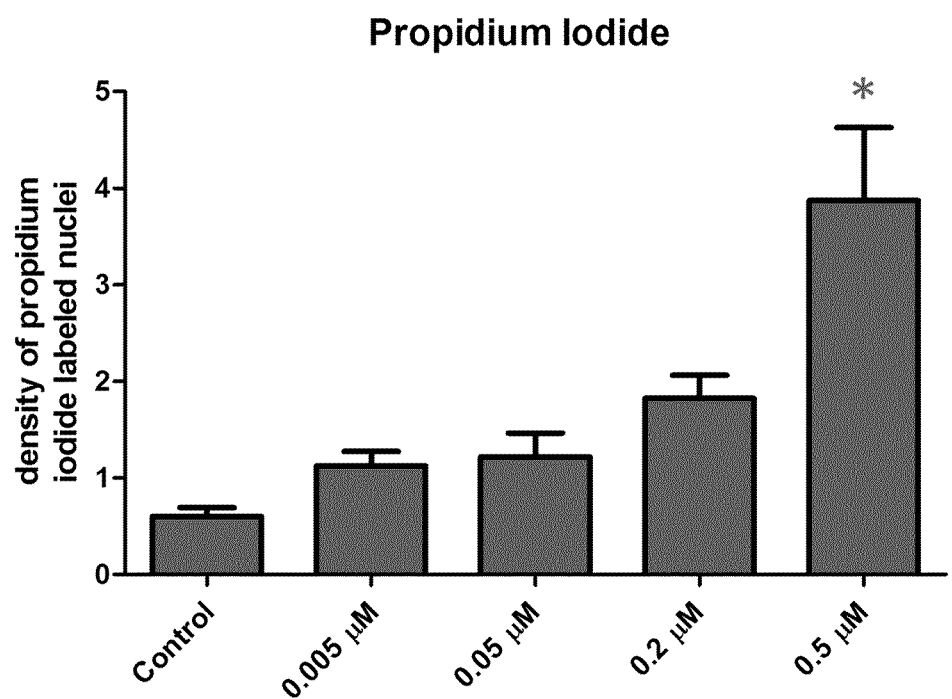
FIG. 45. Changes in density (nuclei/1000 µm$^2$) of PI stained nuclei in pyramidal layer of CA1 region of hippocampal organotypic cultures comparing control cultures treated with vehicle and cultures treated with different concentrations of St-Click-BDMC, (compound of formula (III)) (0.005, 0.05, 0.2 and 0.5 µM drug-eq.). Asterisk indicate statistically significant differences after ANOVA analyses followed Bonferroni's post hoc tests. n>3, mean±SEM.
Figure 46:
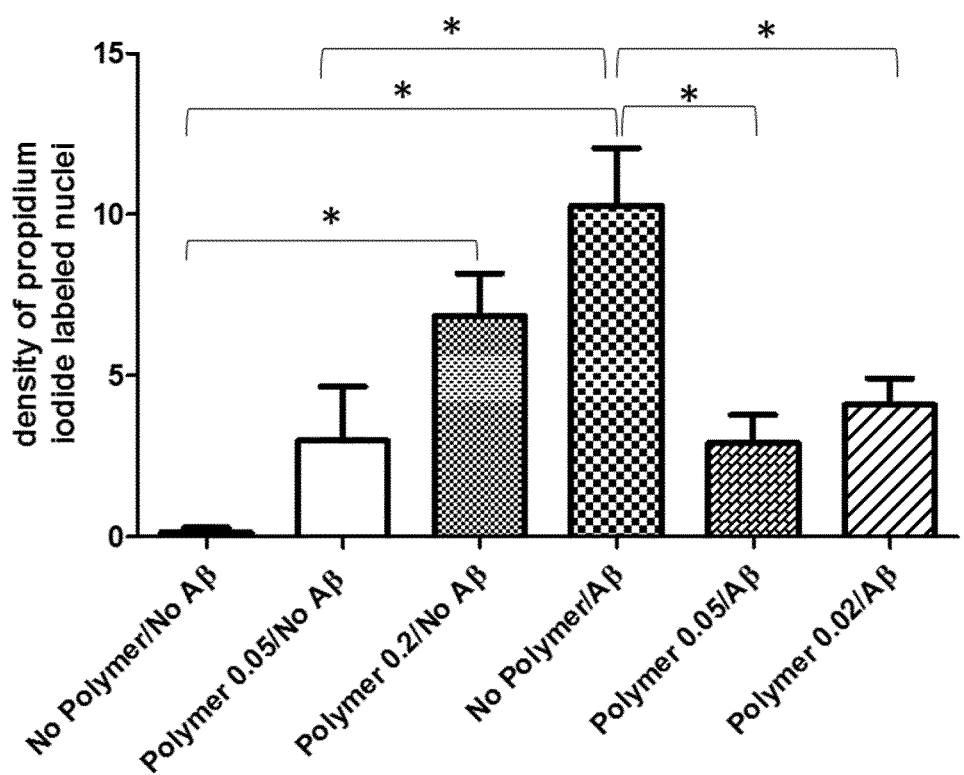
FIG. 46. Changes in density (nuclei/1000 µm$^2$) of PI stained nuclei in pyramidal layer of CA1 region of hippocampal organotypic cultures comparing control cultures treated with vehicle (No polymer/No Aβ), cultures pre-treated with different concentrations of polymer conjugate (compound of formula (III)) (0.05 µM drug-eq. (Polymer 0.05/No Aβ) and 0.2 µM drug-eq. (Polymer 0.2/No Aβ), exposed only to Aβ$_{1-42}$ peptide (No polymer/Aβ) or exposed to Aβ$_{1-42}$ and pretreated with different concentrations of polymer conjugate (0.05 µM drug-eq. (Polymer 0.05/Aβ) and 0.2 µM drug eq. (Polymer 0.2/Aβ). Blue asterisk in bars indicate statistically significant differences from control group and red asterisk indicate statistically significant differences from cultures exposed only to Aβ$_{1-42}$ peptide (No polymer/Aβ), after ANOVA analyses followed by Bonferroni's post hoc tests. n>3, mean±SEM.

Previous work has provided strong evidence that the synthetic peptide Aβ$_{1-42}$ is able to induce neural injury in this type of organotypic culture. Hence, the aim was to analyze this cell damage and its putative prevention by a pretreatment with the St-Click-BDMC 4 wt % using propidium iodide (PI) staining (FIGS. 45 and 46). PI is a polar compound impermeable to intact cell membranes, but capable to penetrate damaged cells and to bind to nuclear DNA, providing a bright red fluorescence. This labeling, allow us the quantification of the density of degenerated cells in a given region. In our case, the region of interest (ROI) was the CA1 region of hippocampus (cornus ammonis 1), where several studies have found neurodegenerative effects induced by Aβ peptides.

Viability of the organotypic cultures in the presence of St-Click-BDMC and absence of Aβ peptides was firstly investigated (48 hours incubation). Slices were stained with PI, fixed and finally analyzed by confocal microscopy. Our polymer conjugate, up to 0.2 µM BDMC-eq, did not induce significant changes in IP positive nuclei density when compared to control cultures (0.005 µM $F_{(4, 18)}$=11.096, ρ=1; 0.05 µM $F_{(4, 18)}$=11.096, ρ=1; 0.2 µM $F_{(4, 18)}$=11.096, ρ=0.41). At 0.5 µM drug-eq. concentration an increase in cell death was observed ($F_{(4, 18)}$=11.096, p<0.0001) (See FIG. 45).

The concentrations of 0.05 and 0.2 µM drug-eq. were then selected in order to have the maximum tolerated concentration to provide neuroprotective effects in Aβ$_{1-42}$ treated cultures. In this case, organotypic slices were pretreated with the polymer conjugate 48 hours before Aβ cell death induction. Thereafter, cultured slices were treated with a second dose of conjugate and Aβ$_{1-42}$ (1 µM final concentration). 48 hours later, cell death was quantified after staining with PI, fixation and analysis by confocal microscopy. In this case, pretreatment with 0.2 µM BDMC-eq. induced a significant increase in cell death ($F_{(5,9)}$=9.574, ρ=0.006) but not in the case of 0.05 µM BDMC-eq. Cultures treated with Aβ$_{1-42}$ increased cell death when compared to controls (vehicle ($F_{(5,19)}$=9.574, ρ=0.0001), and 0.05 μM drug-eq. of polymer conjugate ($F_{(5,19)}$=9.574, ρ=0.006)) as shown in FIG. 46. Pretreatment of cultures with 0.05 μM polymer conjugate ($F_{(5,19)}$=9.574, ρ=0.005) or 0.2 μM ($F_{(5,19)}$=9.574, ρ=0.026) before $Aβ_{1-42}$ addition induced a significant decrease in the density of PI labeled nuclei when compared with cultures treated only with $Aβ_{1-42}$ peptide. (FIG. 46).

Overall, the construct bearing BDMC tested in organotypic cultures shows no toxicity after 48 hours of treatment at the different concentrations tested, except for 0.5 μM concentration. When repeated doses were applied (in the case of the pretreatment experiment), the 0.2 μM concentration resulted toxic for the non $Aβ_{1-42}$ peptide treated cultures, however, this concentration was effective for $Aβ_{1-42}$ toxicity prevention. Pretreatment with polymer conjugate at either 0.05 or 0.2 μM of drug-eq. significantly reduced cell death in $Aβ_{1-42}$ peptide treated cultures. As 0.05 μM concentration resulted enough to produce significant neuroprotective effects against $Aβ_{1-42}$ neurotoxicity without being toxic, this concentration was selected to move forwards. Further experiments are ongoing in order to identify the possible mechanisms of neuroprotection followed by our constructs.

9.6. Preliminary Studies of St-Click-BDMC Demonstrating Safety on a Genetically Modified Alzheimer's Disease Model For that purpose, the mouse strain ArcAbeta was used as Alzheimer's mouse in vivo model. As our idea is to tackle the disease from a neuroprotective point of view, young animals (from 8-11 months) were chosen. Since this mouse model starts to accumulate plaque burden at around 6-9 months of age, excessive and irreversible amounts of Aβ plaques will not be present. Firstly, in vivo safety is a go/no go step for any tested compound in order to proceed with its validation. Therefore, a pilot study with St-click-DO3A-Gd-Cy5.5.-BDMC was designed with a dose schedule selected based on PK studies. In this first experiment, animal weight was monitored as a proof of safety upon successive administrations of the compound. Three different groups of animals were chosen: wild type animals as control (×2), ArcAbeta animals used as non-treated controls injected with saline (×7) and ArcAbeta animals treated with the compound at a comparable dose as that used in the biodistribution studies (2 mg·$Kg^{-1}$ BDMC eq.) (×7).

Figure 47:
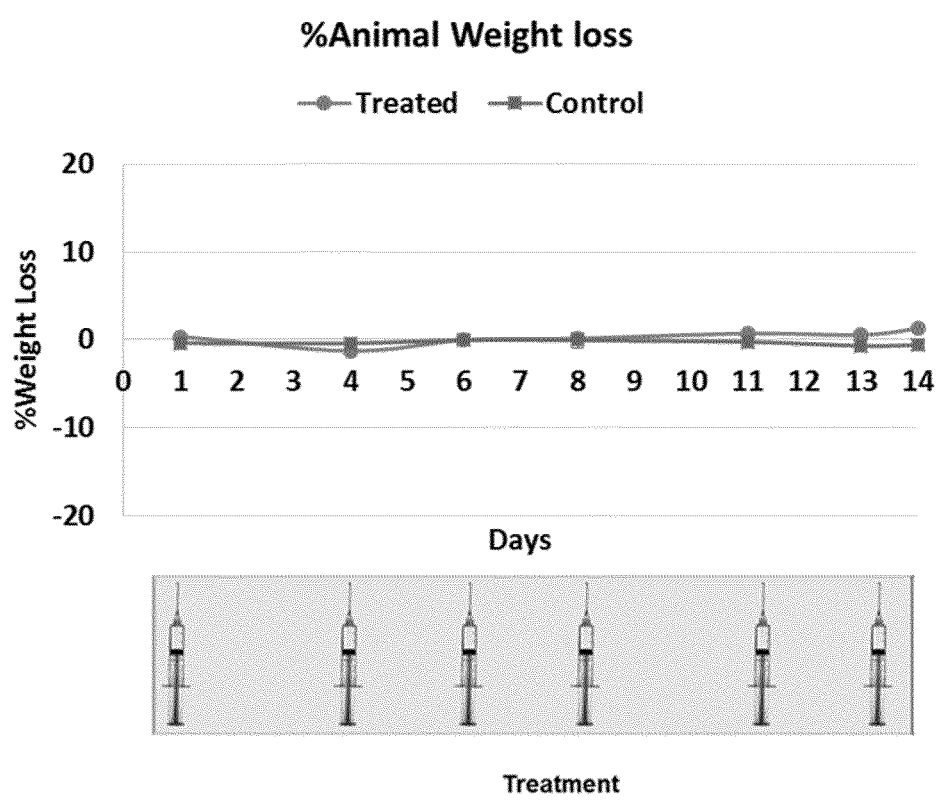
FIG. 47. Experimental design from the treatments with compound of formula (III) performed in ArcAbeta model together with the animal weight registration as a proof of treatment safety.

Animals were injected six times within two weeks without showing signs of toxicity as it is depicted in FIG. 47 where no weight loss of the treated animals was observed.

Example 10. Validation as Carrier to Cancer Applications 10.1. Synthetic Protocol and Characterization.

Figure 48:
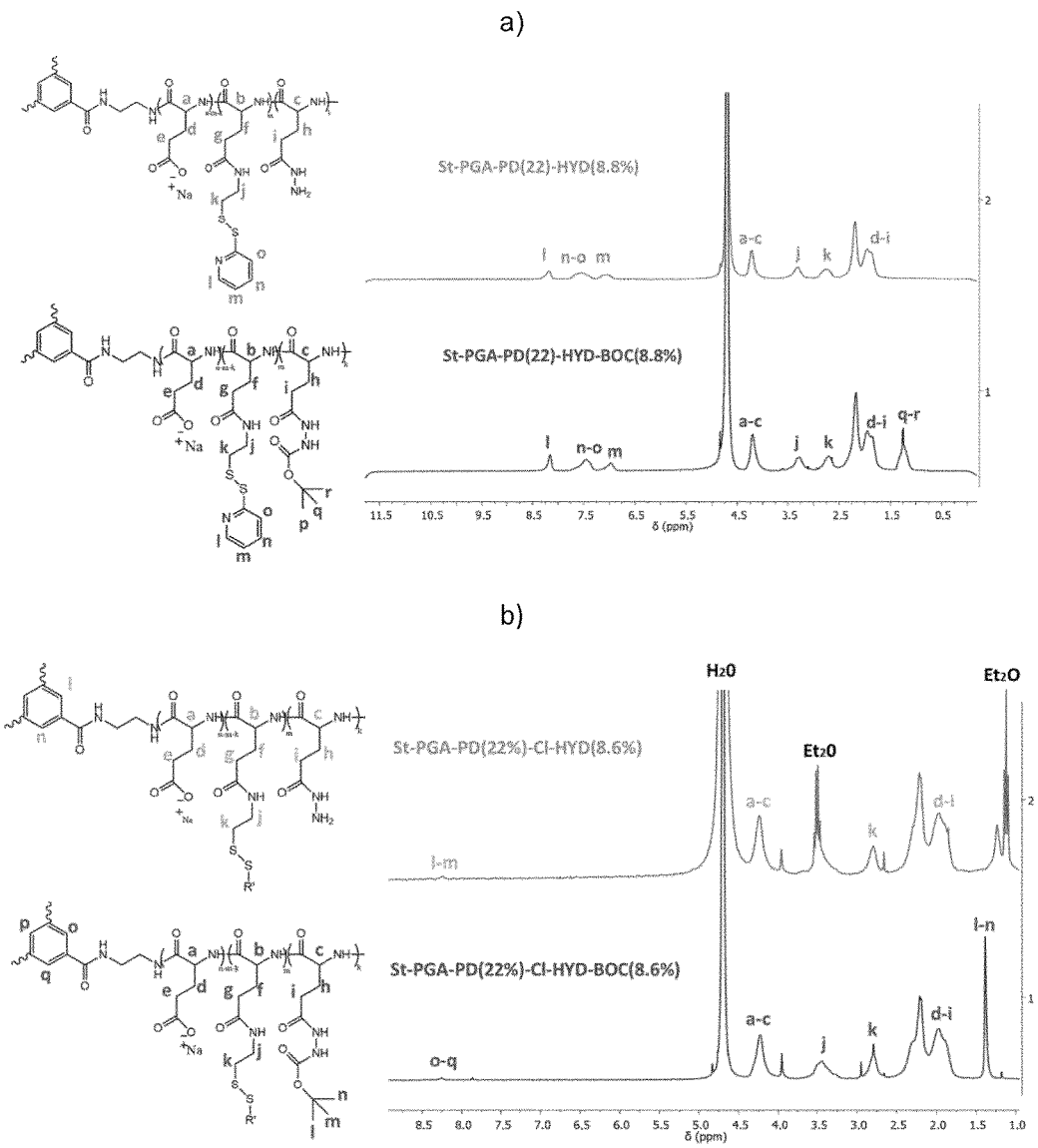
FIG. 48. $^1$H-NMR in $D_2O$ of a) St-PGA-PD(22%)-Hyd (8.8%) and St-PGA-PD(22%)-Hyd-Boc(8.8%) with assignations, and b) St-PGA-PD(22%)-Cl-Hyd(8.6%) and St-PGA-PD(22%)-Cl-Hyd-Boc(8.6%) with assignations. R' represents the binding point to the recurring formula (III).

We aimed to obtain conjugates for systemic administration looking for a new therapeutic strategy in cancer research. As a model drug, Doxorubicin (DOX) was conjugated via pH-labile bonds (hydrazone) to compounds of formula I, II or III, cross-linked with 20% PD groups. The synthesis of compounds of based on compounds of formula (III) is described in detail herein. First of all, hydrazone linker was introduced into the polymer backbone of compounds of formula III. Briefly, in a one-necked round bottom flask with a stir bar and two septums, 1 eq. of compound of formula III (acid form) was dissolved in the required volume of anh. DMF (i.e. 40 mL for 400 mg). Afterwards the eq. for the desired modification of DMTMM·$BF_4$ were added, dissolved in anh. DMF (i.e. 0.9302 mmol, 0.3 eq. for 20% modification). The pH was checked to be 5. After 10 min, the corresponding amine (tert-butyl-carbazate) was added, dissolved in t anh DMF. The pH was adjusted to 7-8 with DIEA. The reaction was allowed to proceed for 48 hours, stirring at r.t. under $N_2$ atmosphere. The product was precipitated in diethyl ether, filtered-off and dried. The Boc protecting group was removed with TFA. The reaction was allowed to proceed for 45 minutes, stirring at room temperature. The product was then precipitated into cold diethyl ether, washed three times with diethyl ether, and twice with milli-Q® water pH3. A colourless amorphous solid was obtained after freeze-drying. FIG. 48 shows the proton NMRs of examples of compounds of formula (II and III) synthesized following this procedure. Next, % mol GAU of DOX was incorporated into the compound by reaction in DMSO, catalyzed with four drops of acetic acid, the reaction was allowed to proceed for 48 hours, stirring at r.t., under $N_2$ atmosphere. After evaporation of half of the volume, the polymers were precipitated in cold diethyl ether by first adding THF in order to improve the miscibility of DMSO in ether. The precipitate was dissolved in 6 mL of DMF and purified by size-exclusion chromatography on a Sephadex® LH-20 column. The first fraction was isolated and the solvent was evaporated using a vacuum pump. The dried product was suspended in milli-Q® water and converted into the sodium salt form by adding $NaCO_3$. The excess of salts was removed by size-exclusion chromatography on a Sephadex® G-25 column. A colourless amorphous solid was obtained after freeze-drying. The total drug loading was measured by UV/VIS spectroscopy at 480 nm resulting in 2.5 mol % Glutamic Acid Units (GAU) DOX (7.85 wt %). Yields: 56-85%

10.2. Cell Viability.

Mouse 4T1 breast cancer cells were cultured in RPMI 1640 (with L-Glutamine and 25 mM Hepes) medium and incubated at 37° C. with an atmosphere of 5% carbon dioxide. MTS cell viability assay was performed with quantification after 72 hours.

In each well of a sterile 96-well microtiter plate, 2000 cells were seeded and incubated for 24 hours under the same conditions mentioned before. A stock solution of 1 mg/mL (DOX eq.) of the compound of the invention was prepared in PBS and diluted with medium to reach a final concentration of 0.1-50 μg/mL. The medium from six wells was removed and replaced by 100 μL of each dilution. After 72 hours of incubation, 10 μL of MTS/PMS (20:1) was added to each well. The cells were then incubated for 3 more hours.

The absorbance at 570 nm was measured spectrophotometrically using $Victor^2Wallace$™ plate reader. For calculations, the absorbance of treated cells was compared with the absorbance of untreated control cells, representing 100% cell viability.

Figure 49:
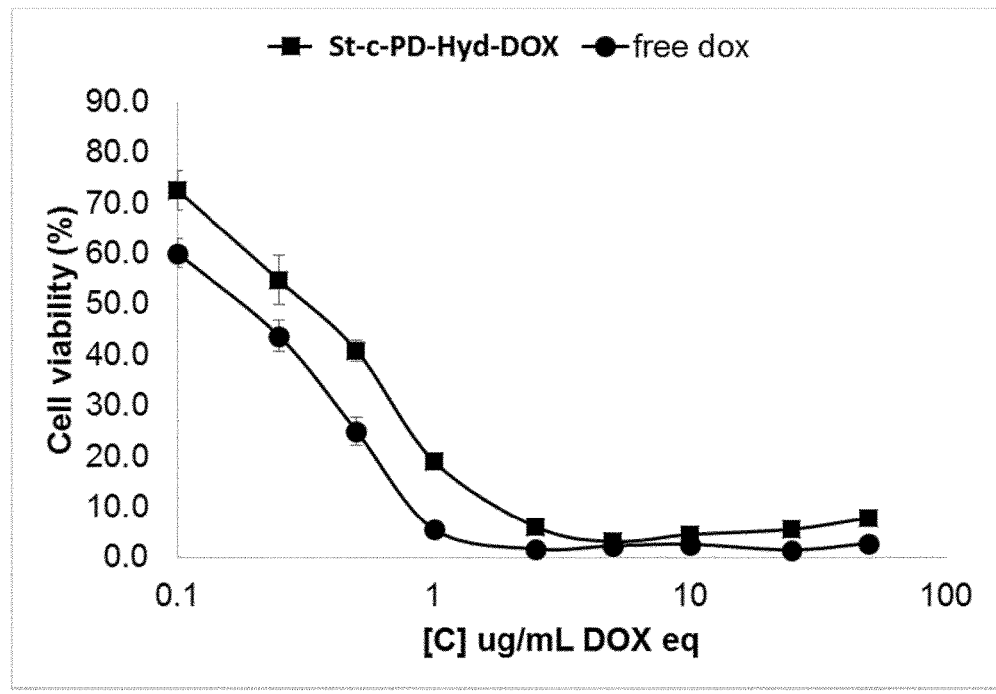
FIG. 49. Cell viability against 4T1 breast cancer cells incubated with free DOX and St-PGA-PD(22%)-Cl-Hyd (8.4%)-Dox(2.5%), compound of formula (III).

As is represented in FIG. 49, the compound exerted a toxicity similar of that of free DOX, and therefore, it represents a promising candidate.

10.3. Drug Release.

Figure 50:
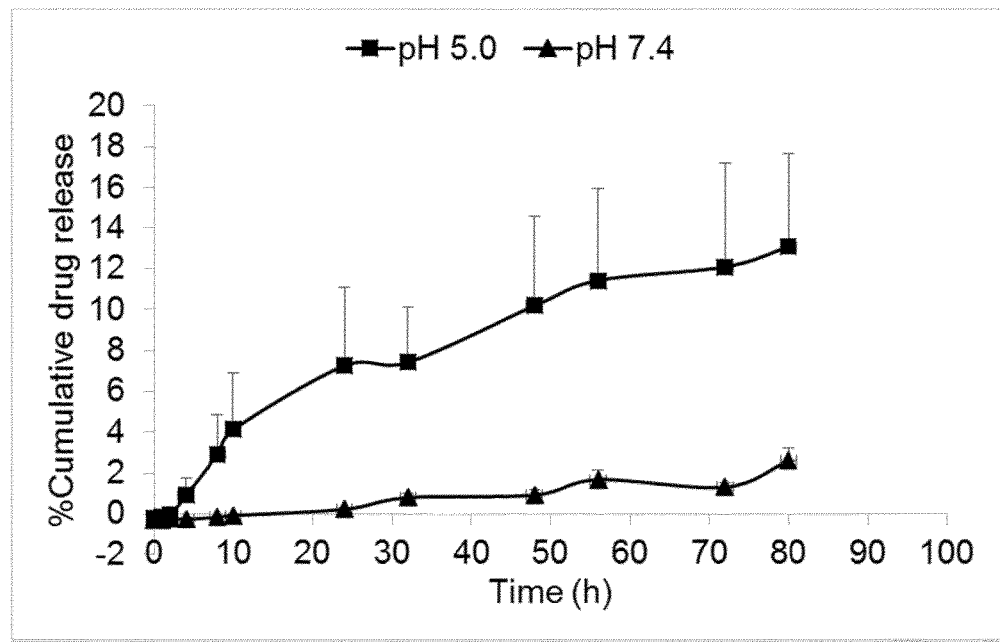
FIG. 50. Drug release studies at pH5 and pH7.4 of St-PGA-PD(22%)-Cl-Hyd(8.4%)-Dox(2.5%), compound of formula (III).

DOX release profile under different pH conditions was explored. The compound of the invention was dissolved in different pH PBS solutions (pH 5 and 7.4) at a concentration of 3 mg/mL. Then, 2 mL of this solution was added in a Float-A-lyzer G2 device (MWCO 1000 Da). The device floated under stirring in 100 mL of the corresponding buffer solution. All samples were incubated in an oven at 37° C. during the experiment. Aliquots of 1000 μL PBS solution wherein the device floated were taken at different timepoints (0 min, 15 min, 30 min, 45 min, 1 h, 2 h, 4 h, 8 h, 12 h, 24 h, 32 h, 48 h, 56 h, 72 h, 80 h, 96 h, 168 h) and replaced with, 1000 μL of fresh PBS solution was added to maintain the volume of 100 mL. After freeze-drying, each aliquot was dissolved in 120 μL DMSO 10% and 100 μL of this was added on a 96-well dark plate. The concentration of DOX on the plates was measured by fluorescence spectroscopy by triplicate. A calibration curve of DOX in DMSO 10% was prepared from dilutions by following the same procedure. The fluorescence (excit 450/emi 595) nm was measured using Victor²Wallace™ plate reader.

pH-dependence drug release was obtained since there was almost no release at pH 7.4 and about 18% drug release at pH 5.0 at 80 hours. FIG. 50.

The invention claimed is:

1. A compound of formula (I) below, comprising homopolypeptides or random or block co-polypeptides:

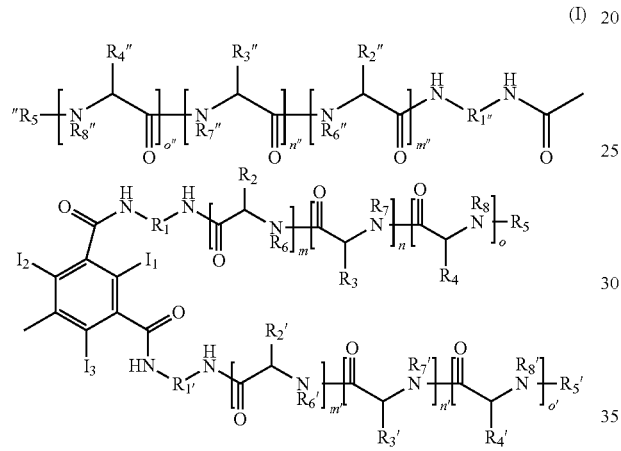

(I)

or its salts, solvates or isomers, wherein:
m, m', m", n, n', n", o, o' and o" are integers independently selected from 0 to 500, wherein at least one of them is ≥1;
$R_6$ to $R_8$, $R_{6'}$ to $R_{8'}$ and $R_{6''}$ to $R_{8''}$ are independently selected from H and methyl;
$I_1$ to $I_3$ are independently selected from the group consisting of H; halogen; Deuterium; and ($C_1$-$C_{20}$)-alkyl;
$R_2$ to $R_4$, $R_{2'}$ to $R_{4'}$ and $R_{2''}$ to $R_{4''}$ are independently selected from the group consisting of:

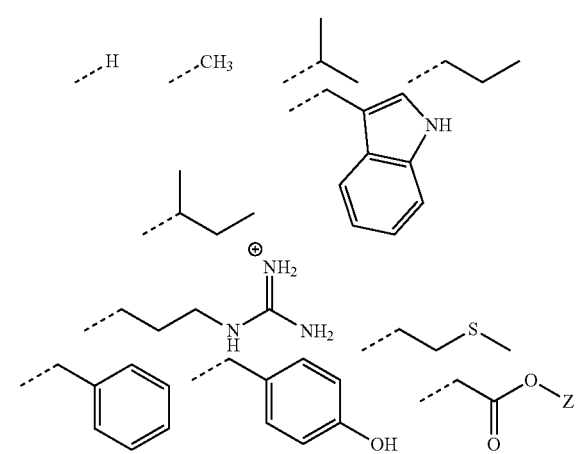

-continued

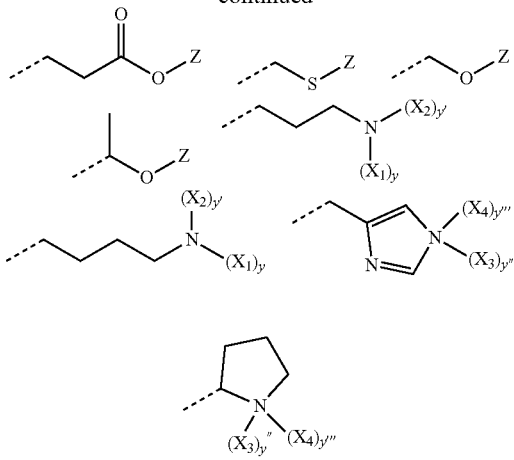

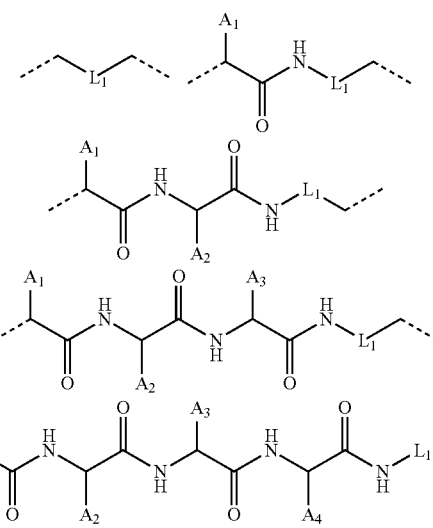

$X_1$ and $X_2$ are independently selected from the group consisting of H; N; $NH_2$; and Z;
$X_3$ and $X_4$ are independently selected from the group consisting of H; and Z;
y and y' are integers between 0 and 3; and y+y'=2 or 3;
y" and y'" are integers between 0 and 2; and y"+y'"=1 or 2
Z is selected from the group consisting of H; metallic counterion; inorganic counterion; and an amino acid protecting group;
$R_1$, $R_{1'}$ and $R_{1''}$ are radicals independently selected from the group consisting of:

$A_1$, $A_2$, $A_3$ and $A_4$ are radicals independently selected from the group as defined for $R_2$ to $R_4$, $R_{2'}$ to $R_{4'}$, and $R_{2''}$ to $R_{4''}$;
$L_1$ is a radical independently selected from the group consisting of a ($C_1$-$C_{500}$)-alkyl, wherein one or more H is optionally substituted by: (1) ($C_3$-$C_{30}$)-cycloalkyl, (2) a C-radical derived from a ring system with 1-6 rings, each ring being independently saturated, partially unsaturated or aromatic, the rings being isolated or fused and having 3-20 members each member independently selected from the group consisting of C, CH, $CH_2$, CO, N and NH, (3) OH, (4) $NR_aR_b$, (5) $ONR_cR_d$, (6) CN, (7) halide, (8) $SH_2$, (9) $SR_eR_f$, (10) $N(H)NH_2$,

(11) $R_gCOR_h$, (12) $COOR_i$, (13) $CON(R_j)(R_k)$, (14) $R_lN(R_m)CON(R_n)_2$, (15) $(C_1-C_{30})$-alkene, (16) $(C_1-C_{30})$-alkyne, (17) $N_3$, (18) $R_oCH(OR_p)(OR_q)$, (19) $R_rCH(SR_s)(SR_t)$, (20) $R_nBoron(OR_v)(OR_w)$, (21) $COR_x$; and wherein one of more C are independently replaced by $(C_3-C_{30})$-cycloalkyl, aryl, aryl-$(C_1-C_{30})$-alkyl, $NR_yR_z$, CO, O, S, Boron, halide, P and $(O-CH_2-CH_2)_B$;

B is an integer between 1 and 500;

$R_a$, $R_b$, $R_c$, $R_d$, $R_e$, $R_f$, $R_h$, $R_i$, $R_j$, $R_k$, $R_m$, $R_n$, $R_p$, $R_q$, $R_s$, $R_t$, $R_v$, $R_w$, $R_x$, $R_y$ and $R_z$ are radicals independently selected from the group consisting of H; $(C_1-C_{30})$-alkyl; $(C_1-C_{30})$-alkylphenyl; phenyl $(C_1-C_{30})$-alkyl; and $(C_3-C_8)$-cycloalkyl, wherein one or more carbons are optionally substituted by an heteroatom selected from the group consisting of O; S; F; N; NH; P; and CO;

$R_g$, $R_l$, $R_o$, $R_r$ and $R_u$ are radicals independently selected from the group consisting of $(C_1-C_{30})$-alkyl; $(C_1-C_{30})$-alkylphenyl; phenyl; $(C_1-C_{30})$-alkyl; and $(C_3-C_8)$-cycloalkyl, wherein one or more carbons are optionally substituted by an heteroatom selected from the group consisting of O; S; F; N; NH; P; and CO;

$R_5$, $R_{5'}$ and $R_{5''}$ are radicals independently selected from the group consisting of H; and $(C_1-C_{500})$-alkyl, optionally substituted by: (1) $(C_3-C_{30})$-cycloalkyl, (2) a C-radical derived from a ring system with 1-6 rings, each ring being independently saturated, partially unsaturated or aromatic, the rings being isolated or fused and having 3-20 members each member independently selected from the group consisting of C, CH, $CH_2$, CO, N and NH, (3) OH, (4) $NR_aR_b$, (5) $ONR_cR_d$, (6) CN, (7) halide, (8) $SH_2$, (9) $SR_eR_f$, (10) $N(H)NH_2$, (11) $R_gCOR_h$, (12) $COOR_i$, (13) $CON(R_j)(R_k)$, (14) $R_lN(R_m)CON(R_n)_2$, (15) $(C_1-C_{30})$-alkene, (16) $(C_1-C_{30})$-alkyne, (17) $N_3$, (18) $R_oCH(OR_p)(OR_q)$, (19) $R_rCH(SR_s)(SR_t)$, (20) $R_nBoron(OR_v)(OR_w)$, (21) $COR_x$; and wherein one of more C are independently replaced by $(C_3-C_{30})$-cycloalkyl, aryl, aryl-$(C_1-C_{30})$-alkyl, $NR_yR_z$, CO, O, S, Boron, halide, P and $(O-CH_2-CH_2)_B$;

B is an integer between 1 and 500;

$R_a$, $R_b$, $R_c$, $R_d$, $R_e$, $R_f$, $R_h$, $R_i$, $R_j$, $R_k$, $R_m$, $R_n$, $R_p$, $R_q$, $R_s$, $R_t$, $R_v$, $R_w$, $R_x$, $R_y$ and $R_z$ are radicals independently selected from the group consisting of H; $(C_1-C_{30})$-alkyl; $(C_1-C_{30})$-alkylphenyl; phenyl $(C_1-C_{30})$-alkyl; and $(C_3-C_8)$-cycloalkyl, wherein one or more carbons are optionally substituted by an heteroatom selected from the group consisting of O; S; F; N; NH; P; and CO;

$R_g$, $R_l$, $R_o$, $R_r$ and $R_u$ are radicals independently selected from the group consisting of $(C_1-C_{30})$-alkyl; $(C_1-C_{30})$-alkylphenyl; phenyl; $(C_1-C_{30})$-alkyl; and $(C_3-C_8)$-cycloalkyl, wherein one or more carbons are optionally substituted by an heteroatom selected from the group consisting of O; S; F; N; NH; P; and CO.

2. The compound according to claim 1, wherein:

$I_1$, $I_2$ and $I_3$, are radicals independently selected from the group consisting of H; Deuterium; and F;

$R_5$, $R_{5'}$ and $R_{5''}$ are identical between them and selected from the group consisting of H; CO—$(C_1-C_{20})$-alkyl; CONH—$(C_1-C_{20})$-alkyl; and pyroglutamate.

3. The compound according to claim 1, wherein:

$R_2=R_{2'}=R_{2''}$, $R_3=R_{3'}=R_{3''}$, and $R_4=R_{4'}=R_{4''}$, and each of them is independently selected from the group consisting of:

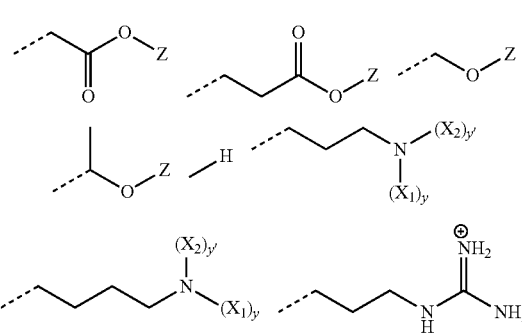

$X_1$ and $X_2$ are independently selected from the group consisting of H; N; —$NH_2$; and Z;

y and y' are integers between 0 and 3; and y+y'=2 or 3;

$R_1=R_{1'}=R_{1''}$ and $R_1$ is selected from:

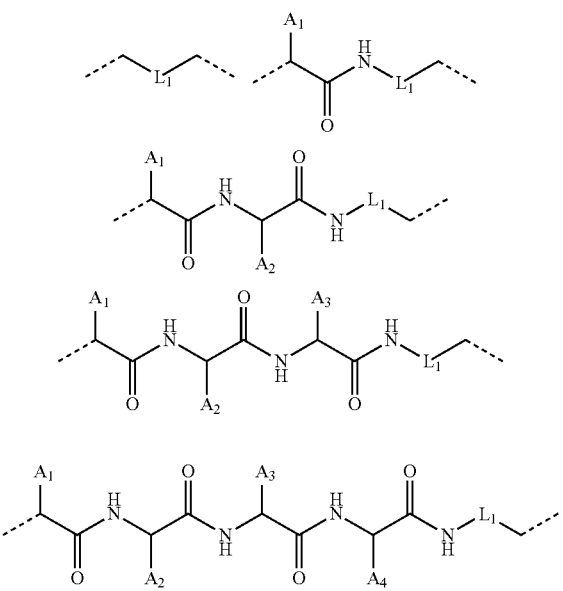

$A_1$, $A_2$, $A_3$ and $A_4$ denote the side residues of hydrophobic amino acids and they are selected from the group consisting of:

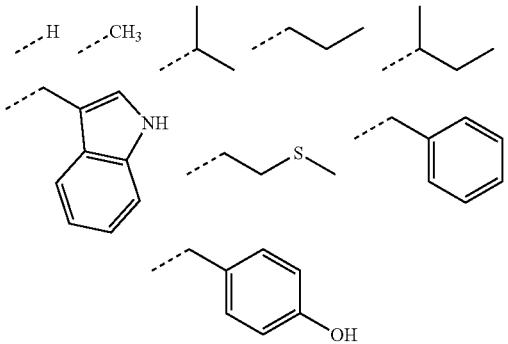

and combinations thereof.

4. A compound of formula (II):

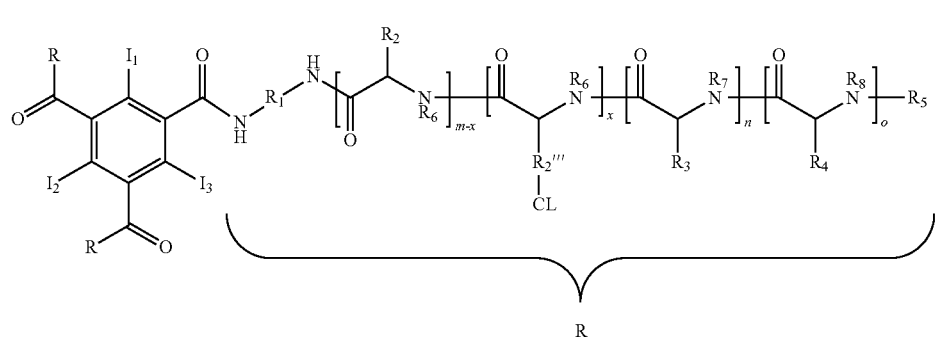

(II)

or its salts, solvates or isomers wherein:
$R_1$ to $R_8$, $I_1$ to $I_3$, n, and o, are defined as in claim 1;
m is an integer between 2-500;
x is a number from 0.01*m to 0.5*m;
$R_{2'''}$ is a radical selected from the group consisting of:

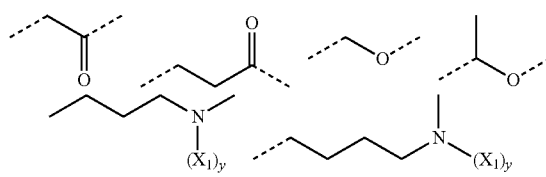

$X_1$ is H;
y is 0 or 1;
CL is a radical selected from the group consisting of a $(C_1-C_{500})$-alkyl, wherein one or more H is optionally substituted by: (1) $(C_3-C_{30})$-cycloalkyl, (2) a C-radical derived from a ring system with 1-6 rings, each ring being independently saturated, partially unsaturated or aromatic, the rings being isolated or fused and having 3-20 members each member independently selected from the group consisting of C, CH, $CH_2$, CO, N and NH, (3) OH, (4) $NR_aR_b$, (5) $ONR_cR_d$, (6) CN, (7) halide, (8) $SH_2$, (9) $SR_eR_f$, (10) $N(H)NH_2$, (11) $R_gCOR_h$, (12) $COOR_i$, (13) $CON(R_j)(R_k)$, (14) $R_lN(R_m)CON(R_n)_2$, (15) $(C_1-C_{30})$-alkene, (16) $(C_1-C_{30})$-alkyne, (17) $N_3$, (18) $R_oCH(OR_p)(OR_q)$, (19) $R_rCH(SR_s)(SR_t)$, (20) $R_uBoron(OR_v)(OR_w)$, (21) $COR_x$; and wherein one of more C are independently replaced by $(C_3-C_{30})$-cycloalkyl, aryl, aryl-$(C_1-C_{30})$-alkyl, $NR_yR_z$, CO, O, S, Boron, halide, P and $(O-CH_2-CH_2)_B$;
B is an integer between 1 and 500;
$R_a$, $R_b$, $R_c$, $R_d$, $R_e$, $R_f$, $R_h$, $R_i$, $R_j$, $R_k$, $R_m$, $R_n$, $R_p$, $R_q$, $R_s$, $R_t$, $R_v$, $R_w$, $R_x$, $R_y$ and $R_z$ are radicals independently selected from the group consisting of H; $(C_1-C_{30})$-alkyl; $(C_1-C_{30})$-alkylphenyl; phenyl $(C_1-C_{30})$-alkyl; and $(C_3-C_8)$-cycloalkyl, wherein one or more carbons are optionally substituted by an heteroatom selected from the group consisting of O; S; F; N; NH; P; and CO;
$R_g$, $R_l$, $R_o$, $R_r$ and $R_u$ are radicals independently selected from the group consisting of $(C_1-C_{30})$-alkyl; $(C_1-C_{30})$-alkylphenyl; phenyl; $(C_1-C_{30})$-alkyl; and $(C_3-C_8)$-cycloalkyl, wherein one or more carbons are optionally substituted by an heteroatom selected from the group consisting of O; S; F; N; NH; P; and CO.

5. The compound according to claim 4, wherein:
$I_1$, $I_2$ and $I_3$, are radicals independently selected from the group consisting of H; Deuterium; and F;
$R_5$ is selected from the group consisting of H; CO—$(C_1-C_{20})$-alkyl; CONH—$(C_1-C_{20})$-alkyl; and pyroglutamate.

6. The compound according to claim 4, wherein:
each $R_2$, $R_3$, and $R_4$ is independently selected from the group consisting of:

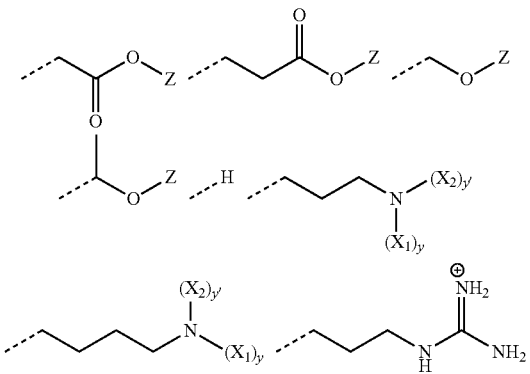

$X_1$ and $X_2$ are defined as in claim 1;
y and y' are defined as in claim 1;
$R_1$ is selected from the following groups:

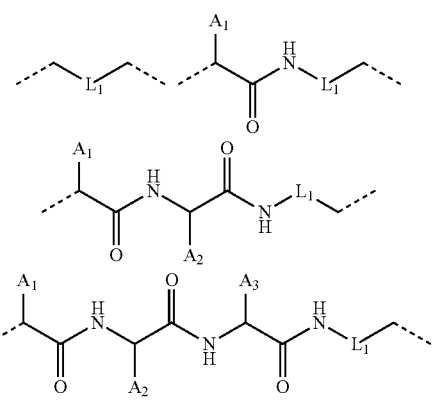

-continued

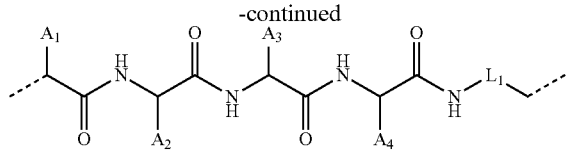

$A_1, A_2, A_3$ and $A_4$ denote the side residues of hydrophobic amino acids and they are selected from the following groups or combinations thereof:

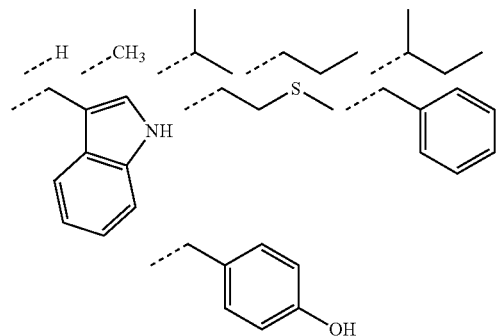

$L_1$ is as defined in claim 1.

7. The compound according to claim 4, wherein:
$R_{2'''}$ is selected from the group consisting of:

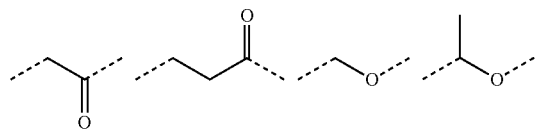

-continued

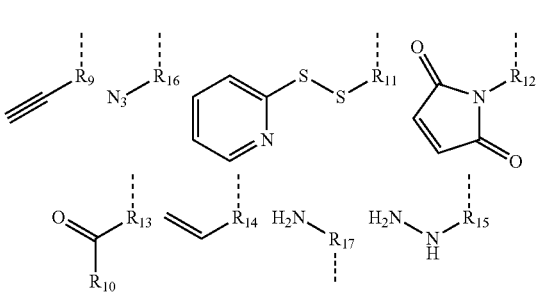

$X_1$ is H;
y is 0 or 1;
CL is selected from the group consisting of:

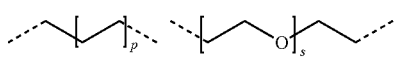

$R_9$ and $R_{11}$ to $R_{17}$ are independently selected from the group consisting of:

p and s are integers independently selected from 0 to 500;
$R_{10}$ is selected from H and $(C_1-C_4)$-alkyl.

8. A cross-linked self-assembled star polymer comprising a recurring unit of formula (III):

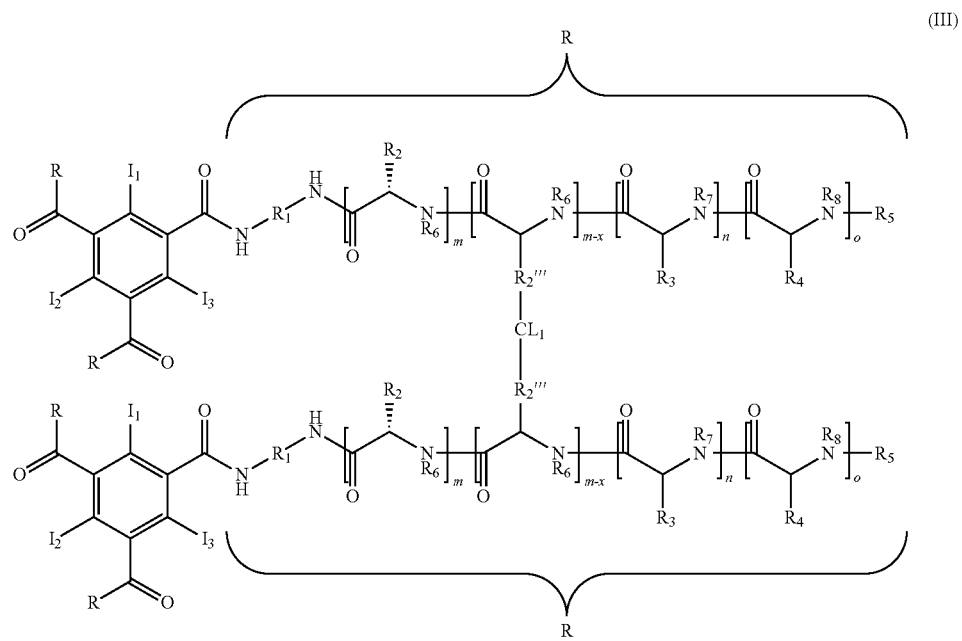

or its salts, solvates or isomers wherein:

$R_1$ to $R_8$, $I_1$ to $I_3$, m, n and o are defined as in claim 1;
x is a, number from 0.01*m to 0.5*m;
$R_{2'''}$ is selected from the group consisting of:

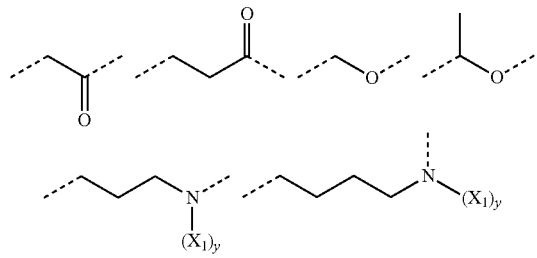

$X_1$ and y are defined as in claim 4;
$CL_1$ is defined as CL in claim 4.

9. The cross-linked self-assembled star polymer according to claim 8, wherein:
$I_1$, $I_2$, and $I_3$, are radicals independently selected from the group consisting of H; Deuterium; and F;
$R_5$ is selected from the group consisting of H; CO—($C_1$-$C_{20}$)-alkyl; CON(H)—($C_1$-$C_{20}$)-alkyl; and pyroglutamate.

10. The cross-linked self-assembled star polymer according to claim 9, wherein:
each $R_2$, $R_3$, and $R_4$ is independently selected from the group consisting of:

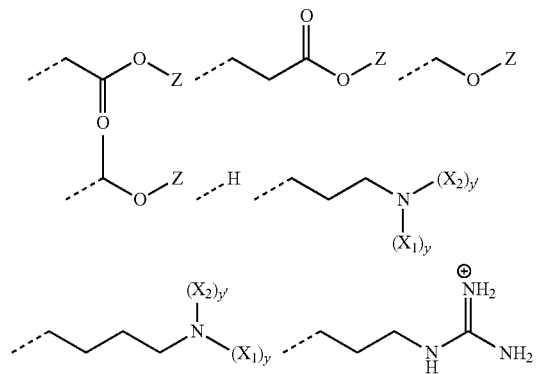

$X_1$ and $X_2$ are defined as in claim 1;
y and y' are defined as in claim 1;
$R_1$ is selected from the following groups:

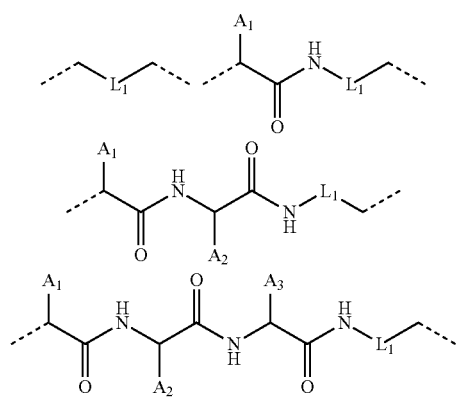

-continued

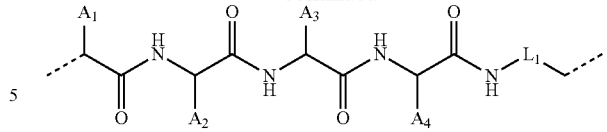

$A_1$, $A_2$, $A_3$ and $A_4$ denote the side residues of hydrophobic amino acids and they are selected from the following groups or combinations thereof:

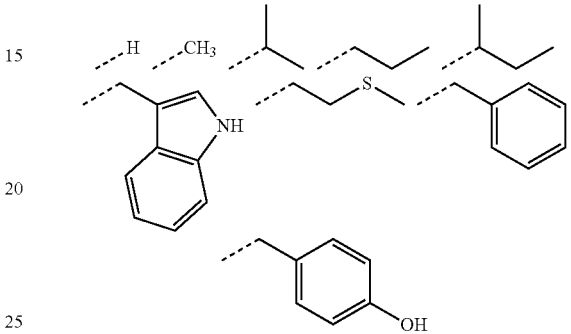

$L_1$ is as defined in claim 1.

11. The cross-linked self-assembled star polymer according to claim 8, wherein:
$R_{2'''}$ is selected from the group consisting of:

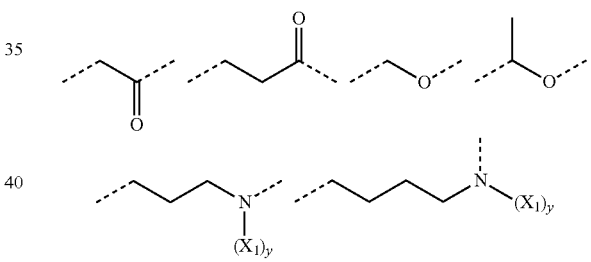

$X_1$ and y are defined as in claim 4;
$CL_1$ is selected from the group consisting of:

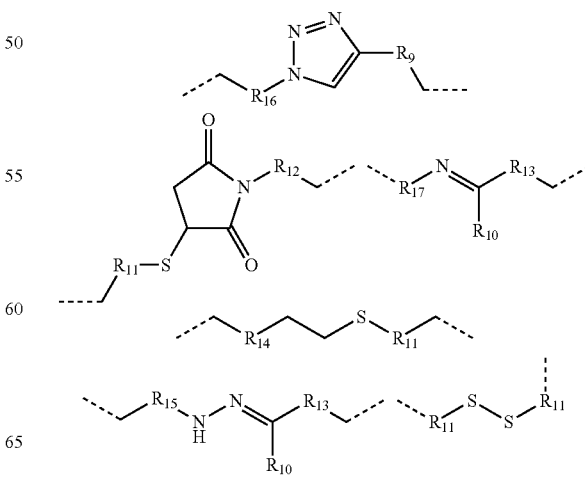

$R_9$ and $R_{11}$ to $R_{17}$ are selected from the group consisting of:

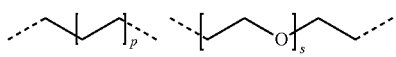

p and s are integers independently selected from 0 to 500;
$R_{10}$ is selected from H and $(C_1-C_4)$-alkyl.

12. A conjugate comprising the compound of formula (I) as defined in claim 1, the compound of formula (II) as defined in claim 4, or the cross-linked self-assembled star polymer of formula (III) as defined in claim 8, and at least an active agent which is linked to the compound or the self-assembled star polymer.

13. The conjugate according to claim 12 wherein the at least active agent is selected from the group consisting of an active ingredient and an imaging agent, or combinations thereof.

14. The conjugate according to claim 13, wherein the at least active ingredient is selected from the group consisting of anticancer agent, antimetastatic agent, anti-inflammatory agent, antioxidant, antiapoptotic, proapoptotic, neuroprotective agent, immunostimulant agent, antioxidants, agent capable to trigger tissue repair and/or regeneration, anti-amyloidotic agent, and plaque/protein aggregates disrupting agents.

15. The conjugate according to claim 14, wherein the at least active ingredient is selected from the group consisting of: vincristine, vinblastine, amiloride, chloroquine, blafiomycyn, fasudil, bisphosphonate, primaquine, meclofenamate, tonabersat, disulfiram, cyclophosphamide, paclitaxel, dendrotoxin, doxorubicine, methotrexate, epirubicine, dinaciclib, buparlisib, palbociclib, veliparib, megestrol, examestane, goserelin, tamoxifen, fulvestrant, trastuzumab, lapatinib, pertuzumab, selegiline, rasagiline, ladostigilM30, demethoxycurcumin, curcumin, and bisdemethoxycurcumin.

16. The conjugate according to claim 12, wherein the conjugate comprises an amount of the at least an active agent in the range between 1 to 70% w/w based on the mass ratio of the at least active agent to the conjugate.

17. A pharmaceutical, diagnostic or theranostic composition comprising at least one conjugate as defined in claim 12 together with one or more appropriate pharmaceutical or diagnostically acceptable excipients.

18. A method for treatment of a neurodegenerative disorder, neurological disease, cancer, infectious disease, disorder related to aging, neuro-inflammation, demyelinating disorder, multiple sclerosis, ischemic disorder, ischemia-reperfusion induced damage, amyloydotic disease, cardiomyopathy, spinal cord injury, immune disorder, inflammatory disorders, rare disease, wound healing and lysosomal storage disease comprising administering the conjugate according to claim 12.

19. A carrier comprising a compound of formula (I) as defined in claim 1, the compound of formula (II) as defined in claim 4, or the cross-linked self-assembled star polymer of formula (III) as defined in claim 8.

20. A process for the synthesis of the compound of formula (I) as defined in claim 1, the process comprising:
(1) reacting an amine or TFA/BF4 salt initiator of formula (IV) below

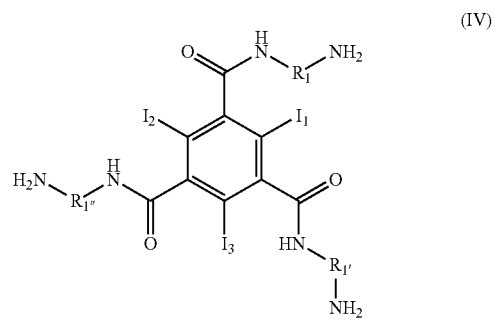

wherein $I_1$ to $I_3$, $R_1$, $R_{1'}$ and $R_{1''}$ are as defined in any of the claims 1-3, with an appropriate N-carboxyanhydride (NCA);
alternatively, reacting the amine or tetrafluoroborate or trifluoroacetate ammonium salt form of initiator of step (1) with the appropriate N-carboxyanhydrides in a sequential manner to obtain a block co-polymer;
alternatively, reacting the amine or tetrafluoroborate or trifluoroacetate ammonium salt form of initiator of step (1) with an appropriate NCA in a statistical manner to obtain random co-polymers;
(2) optionally, reacting the amine group at the N-terminal position with an amine reactive group to introduce $R_5$, $R_{5'}$ and/or $R_{5''}$;
(3) optionally, orthogonally removing amino acid side chains;
(4) purifying the product obtained in step (1), (2) or (3), optionally by fractionation, precipitation, ultrafiltration, dialysis, size exclusion chromatography or tangential flow filtration.

21. A process as defined in claim 20, for the synthesis of the compound of formula (II) as defined in claim 4, the process further comprising:
(5) introducing the CL groups at reactive amino acid side chain, at the appropriate molar ratio;
(6) purifying the product obtained in step (5) optionally by fractionation, precipitation, ultrafiltration, dialysis, size exclusion chromatography or tangential flow filtration.

22. A process as defined in claim 21, for the synthesis of the cross-linked self-assembled star polymer of formula (III) as defined in claim 8, the process further comprising:
(7) reacting the CL groups of the self-assembled compounds of formula (II) forming nanometric assemblies, to covalently cross-link the self-assembled star polymers;
(8) purifying the product obtained in step (7) optionally by fractionation, precipitation, ultrafiltration, dialysis, size exclusion chromatography or tangential flow filtration.

* * * * *